US011351205B2

(12) United States Patent
Lobacki et al.

(10) Patent No.: US 11,351,205 B2
(45) Date of Patent: *Jun. 7, 2022

(54) MICROBIOME RELATED IMMUNOTHERAPIES

(71) Applicant: Finch Therapeutics Holdings LLC, Somerville, MA (US)

(72) Inventors: Joseph Lobacki, Somerville, MA (US); Ulrich Thienel, Somerville, MA (US); Zain Kassam, Somerville, MA (US); Marina Santiago, Somerville, MA (US)

(73) Assignee: Finch Therapeutics Holdings LLC, Somerville, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/541,431

(22) Filed: Dec. 3, 2021

(65) Prior Publication Data
US 2022/0088090 A1    Mar. 24, 2022

Related U.S. Application Data

(63) Continuation of application No. 16/970,532, filed as application No. PCT/US2019/019260 on Feb. 22, 2019.

(60) Provisional application No. 62/743,792, filed on Oct. 10, 2018, provisional application No. 62/743,794, filed on Oct. 10, 2018, provisional application No. 62/634,503, filed on Feb. 23, 2018.

(51) Int. Cl.
A01N 63/00     (2020.01)
A61K 35/741    (2015.01)
A61P 35/00     (2006.01)
A61K 35/37     (2015.01)

(52) U.S. Cl.
CPC .......... A61K 35/741 (2013.01); A61K 35/37 (2013.01); A61P 35/00 (2018.01)

(58) Field of Classification Search
CPC .................................................. A61K 35/741
See application file for complete search history.

(56) References Cited

U.S. PATENT DOCUMENTS

2013/0195804 A1*  8/2013  Borody ............. A61K 35/74
                                                    424/93.4
2014/0255351 A1   9/2014  Berstad et al.
2020/0405778 A1* 12/2020  Lobacki ............ A61K 9/5047

FOREIGN PATENT DOCUMENTS

WO    WO 2016/063263 A2    4/2016
WO    WO 2017/103550 A1    6/2017
WO    WO 2017/211753 A1   12/2017
WO    WO 2018/022327 A1    2/2018
WO    WO 2018/064165 A2    4/2018

OTHER PUBLICATIONS

Vetizou et al (Science vol. 350, Issue 6264, pp. 1079-1084) (Year: 2015).*
International Search Report & Written Opinion, PCT Application No. PCT/US19/19260, dated May 9, 2019, 16 pages.

* cited by examiner

Primary Examiner — Albert M Navarro
(74) Attorney, Agent, or Firm — Morgan, Lewis & Bockius LLP

(57) ABSTRACT

The present invention generally relates to therapeutic compositions and methods for treating cancer patients. The compositions and methods can increase efficacy of an anti-cancer therapy, or treat, prevent, or inhibit an oncology-treatment induced condition (OTIC) induced by an anti-cancer therapy. The therapeutic compositions comprise microbial compositions and, optionally, an anti-cancer therapeutic agent. The methods comprise administering a therapeutic composition comprising a microbial composition and administering an anti-cancer therapy.

20 Claims, No Drawings

MICROBIOME RELATED IMMUNOTHERAPIES

PRIORITY

This application is a continuation of U.S. application Ser. No. 16/970,532, filed Aug. 17, 2020. U.S. application Ser. No. 16/970,532 is U.S. National Stage Application under 37 U.S.C. § 371 of International Application No. PCT/US2019/019260, filed Feb. 22, 2019, and which claims the benefit of, and claims priority to, U.S. Provisional Application No. 62/634,503, filed Feb. 23, 2018; U.S. Provisional Application No. 62/743,792, filed Oct. 10, 2018; and U.S. Provisional Application No. 62/743,794, filed Oct. 10, 2018. The contents of the aforementioned applications are hereby incorporated by reference in their entirety.

FIELD OF THE INVENTION

The present invention generally relates to therapeutic compositions and methods for increasing efficacy of an anti-cancer therapy. The present invention further relates to treating, preventing, or inhibiting an oncology-treatment induced condition (OTIC) induced by an anti-cancer therapy.

BACKGROUND

Cancer can be treated by surgery, chemotherapy (including hormonal therapy), radiation therapy, and/or targeted therapy (including immunotherapy). Many cancers either do not respond or respond poorly to such treatments, or recur following the termination of the treatment. Further, many anti-cancer therapies give rise to or are associated with deleterious health effects in the treated patient. For example, activation of the immune system associated with checkpoint inhibitor therapy is associated with onset or exacerbation of inflammation-associated conditions such as colitis. Therefore, there is an ongoing need for improved anti-cancer therapeutic compositions and treatments, as well as compositions and treatments that treat or inhibit the development or severity of conditions associated with anti-cancer treatments.

SUMMARY

In one aspect, the present disclosure provides a method for treating or preventing an oncology-treatment induced condition (OTIC) induced by an anti-cancer therapy, comprising administering to a subject a therapeutic composition comprising a microbial preparation; wherein the subject is treated with the anti-cancer therapy; and wherein the microbial composition comprises a fecal microbiota of a human donor.

In some cases, the subject is administered the therapeutic composition after treatment with the anti-cancer therapy. In some cases, the therapeutic composition is administered at least 1 day after treatment with the anti-cancer therapy. In some cases, the therapeutic composition is administered at least 3 days after treatment with the anti-cancer therapy. In some cases, the therapeutic composition is administered at least 5 days after treatment with the anti-cancer therapy. In some cases, the therapeutic composition is administered at least 1 week after treatment with the anti-cancer therapy. In some cases, the therapeutic composition is administered at least 4 weeks after treatment with the anti-cancer therapy. In some cases, the therapeutic composition is administered at least 8 weeks after treatment with the anti-cancer therapy.

In some cases, the subject is administered the therapeutic composition before treatment with the anti-cancer therapy. In some cases, the therapeutic composition is administered at least 1 day before treatment with the anti-cancer therapy. In some cases, the therapeutic composition is administered at least 3 days before treatment with the anti-cancer therapy. In some cases, the therapeutic composition is administered at least 5 days before treatment with the anti-cancer therapy. In some cases, the therapeutic composition is administered at least 1 week before treatment with the anti-cancer therapy. In some cases, the therapeutic composition is administered at least 4 weeks before treatment with the anti-cancer therapy. In some cases, the therapeutic composition is administered at least 8 weeks before treatment with the anti-cancer therapy.

In some cases, the therapeutic composition prevents or inhibits the OTIC. In some cases, the subject is administered the therapeutic composition concurrently with the anti-cancer therapy. In some cases, the anti-cancer therapy is chemotherapy, and the subject is administered the therapeutic composition between consecutive chemotherapeutic administrations. In some cases, the anti-cancer therapy is radiation therapy, and the subject is administered the therapeutic composition between consecutive radiation therapy administrations. In some cases, the therapeutic composition increases the efficacy of the anti-cancer therapy. In some cases, the anti-cancer therapy comprises surgery, radiation therapy, administration of a chemotherapeutic agent, stem-cell transplant therapy, or targeted therapy. In some cases, the anti-cancer therapy is radiation therapy. In some cases, the anti-cancer therapy is a surgery which excises a tumor or an organ/tissue comprising cancerous cells. In some cases, the anti-cancer therapy comprises administration of a chemotherapeutic agent. In some cases, the chemotherapeutic agent is selected from the group consisting of: alkylating agents, alkyl sulfonates, aziridines, an ethylenimine, a methylamelamine, an acetogenin, a camptothecin bryostatin, cally statin, CC-1065, a cryptophycin, dolastatin, duocarmycin, eleutherobin, pancratistatin, a sarcodictyin, spongistatin, a nitrogen mustard, a nitrosurea, an antibiotic, a dynemicin; a bisphosphonate, an esperamicin, neocarzinostatin chromophore and related chromoprotein enediyne antibiotic chromophores, an aclacinomysin, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin, epirubicin, esorubicin, idarubicin, marcellomycin, a mitomycin, mycophenolic acid, nogalamycin, an olivomycin, peplomycin, potfiromycin, puromycin, quelamycin, rodorubicin, streptonigrin, streptozocin, tubercidin, ubenimex, zinostatin, zorubicin an anti-metabolite, a folic acid analogue, a purine analog, a pyrimidine analog, an androgen, an anti-adrenal, a folic acid replenisher, aceglatone, aldophosphamide glycoside, aminolevulinic acid, eniluracil, amsacrine, bestrabucil, bisantrene, edatrexate, demecolcine, diaziquone, elformithine, elliptinium acetate, an epothilone, etoglucid, gallium nitrate, hydroxyurea, lentinan, lonidainine, a maytansinoid, mitoguazone, mitoxantrone, mopidanmol, nitraerine, pentostatin, phenamet, pirarubicin, losoxantrone, podophyllinic acid, 2-ethylhydrazide, procarbazine, PSK polysaccharide complex, razoxane, rhizoxin, sizofuran, spirogermanium, tenuazonic acid, triaziquone, 2,2',2"-trichlorotriethylamine, a trichothecene, urethan, vindesine, dacarbazine, mannomustine, mitobronitol, mitolactol, pipobroman, gacytosine, arabinoside ("Ara-C"), cyclophosphamide, thiotepa, a taxoid, ABRAXANE Cremophor-free, an albumin-engineered nanoparticle formulation of paclitaxel and TAXOTERE doxetaxel, chlorambucil, GEMZAR gemcitabine, 6-thioguanine, mercaptopurine, methotrexate, a platinum analog, vinblastine, platinum, etoposide (VP-16), ifosfamide, mitoxantrone, vincristine, NAVELBINE, vinorelbine, novantrone, teniposide, edatrexate, daunomycin, aminopterin, xeloda, ibandronate, irinotecan (Camptosar, CPT-11), topoisomerase inhibitor RFS 2000; difluoromethylornithine (DMFO), a retinoid, capecitabine, combretastatin, leucovorin (LV), oxaliplatin, Binimetinib (Mektovi), Encorafenib (Braftovi), lapatinib (TYKERB), an inhibitor of PKC-α, an inhibitor of Raf, an inhibitor of H-Ras, an inhibitor of EGFR, an inhibitor of VEGF-A, pharmaceutically acceptable salt, acid or derivative thereof, and combinations thereof.

In some cases, the anti-cancer therapy is a stem-cell transplant therapy comprising a peripheral blood transplant, a bone marrow transplant, a cord blood transplant, or a skin-derived stem cell transplant. In some cases, the anti-cancer therapy is a targeted therapy. In some cases, the targeted therapy is an immuno-oncology therapy. In some cases, the immuno-oncology therapy comprises administration to the subject of at least one compound capable of recognizing a tumor-cell antigen and/or a cancer-cell antigen. In some cases, the at least one compound capable of recognizing a tumor-cell antigen and/or a cancer-cell antigen is an engineered protein, a fusion protein, an antibody, or a cytokine. In some cases, the tumor-cell antigen and/or a cancer-cell antigen is selected from the group consisting of: 2B4, 41BB, A2AR, ALK, a B-7 family ligand, BRAF, BTK, BTLA, CCR4, CD19, CD20, CD27, CD28, CD35, CD40, CD50, CD73, CD137, CD160/By55, CD172a/SIRPα, CD200, CD223, CD244, CEACAM, a CHK 1 kinase, a CHK2 kinase, cMET, CSF1R, CTLA-4, CXCR, DNMT, EGFr, GAL9, GITR, HDAC, HER-2, HVEM, ICOS, IDO, KIR, KRAS, LAG3, MEK, mTor, NKG2A, OX40, PARP, PD-1, PD-L1, PD-L2, STAT3, TGF-beta, TIGIT, TIM-3, TKI, a TLR (Toll like receptors), and combinations thereof. In some cases, the at least one compound is an antibody selected from the group consisting of: nivolumab, pembrolizumab, pidilizumab, RMP1-14, AGEN2034, cemiplimab, ipilimumab, 9D9, tremelimumab, AGEN1884, RG2077, and combinations thereof. In some cases, the immuno-oncology therapy is a cell-based immuno-oncology therapy.

In some cases, the cell-based immuno-oncology therapy comprises adoptive cell transfer (ACT) to the subject. In some cases, the ACT is autologous or allogenic. In some cases, a cell used in the cell-based immuno-oncology therapy comprises a Chimeric Antigen Receptor (CAR) or an engineered T Cell Receptor (TCR). In some cases, a cell used in the immuno-oncology therapy is an antigen-presenting cell (APC) or a tumor infiltrating lymphocyte (TIL). In some cases, recognizing a tumor-cell antigen and/or a cancer-cell antigen inhibits downstream signaling of the tumor-cell antigen and/or cancer-cell antigen. In some cases, recognizing a tumor-cell antigen and/or a cancer-cell antigen enhances downstream signaling of the tumor-cell antigen and/or cancer-cell antigen. In some cases, targeted therapy comprises administration of a STING agonist. In some cases, the targeted therapy comprises administration of an interleukin.

In some cases, the subject has a cancer. In some cases, the cancer is selected from the group consisting of: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer; glioblastoma; hepatic carcinoma; hepatoma; intra-epithelial neoplasm; kidney or renal cancer; larynx cancer; leukemia; liver cancer; lung cancer; melanoma; myeloma; neuroblastoma; oral cavity cancer; ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; urothelial cancer; uterine or endometrial cancer; cancer of the urinary system; vulval cancer; lymphoma; Hodgkin's lymphoma; non-Hodgkin's lymphoma (NHL); B-cell lymphoma; small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's Macroglobulinemia; chronic lymphocytic leukemia (CLL); acute lymphoblastic leukemia (ALL); Hairy cell leukemia; chronic myeloblastic leukemia; other carcinomas and sarcomas; and combinations thereof. In some cases, the cancer is bladder cancer, carcinoma of head and neck, colon and rectum cancer, kidney or renal cancer, melanoma, non-small cell lung cancer, triple-negative breast cancer, or urothelial cancer. In some cases, the cancer is classified as PDL-1$^+$ and/or CTLA4$^+$. In some cases, the subject is refractory and/or non-responsive to the anti-cancer therapy. In some cases, the anti-cancer therapy is directed to a checkpoint molecule. In some cases, the anti-cancer therapy comprises administration of at least one of pembrolizumab, nivolumab, or ipilimumab.

In some cases, the subject had not previously been diagnosed with the OTIC. In some cases, the OTIC is caused by the anti-cancer therapy. In some cases, the subject did not show symptoms of the OTIC immediately prior to administration of the anti-cancer therapy. In some cases, the subject showed symptoms of the OTIC immediately prior to administration of the anti-cancer therapy, and the OTIC is exacerbated by the anti-cancer therapy. In some cases, the subject is at risk of developing the OTIC. In some cases, the OTIC comprises bleeding in the subject. In some cases, the OTIC comprises gut dysmotility in the subject. In some cases, the subject experiences nausea, vomiting, bloating, and/or malnutrition. In some cases, the OTIC is a cancer-wasting/malnutrition syndrome. In some cases, the cancer-wasting/malnutrition syndrome is cachexia or sarcopenia. In some cases, the OTIC is a disorder related to the gut-brain axis. In some cases, the disorder related to the gut-brain axis is depression or anxiety.

In some cases, the OTIC is an infection. In some cases, the infection is a viral infection. In some cases, the viral infection is due to a cancer-related virus. In some cases, the method further comprises administering the subject an anti-viral compound. In some cases, the infection is a bacterial infection. In some cases, the bacterial infection is caused by an antibiotic-resistant bacteria selected from the group consisting of: Antibiotic-resistant Proteobacteria, Vancomycin Resistant *Enterococcus* (VRE), Carbapenem Resistant Enterobacteriaceae (CRE), fluoroquinolone-resistant Enterobacteriaceae, Extended Spectrum Beta-Lactamase producing Enterobacteriaceae (ESBL-E), and combinations thereof. In some cases, the OTIC is alopecia. In some cases, the anti-cancer therapy comprises administration of a chemotherapeutic agent.

In some cases, the OTIC is a graft-versus-host disease (GVHD). In some cases, the anti-cancer therapy comprises a stem-cell transplant therapy or a cell-based immuno-oncology therapy. In some cases, the OTIC is selected from the group consisting of: a cardiovascular disease, a dermatologic disease, an autoimmune thyroid disease, hypothyroidism, hyperthyroidism, hypophysitis, thyroiditis, thyrotoxicosis, adrenal insufficiency, type 1 diabetes mellitus, an exocrine pancreas-related disease, inflammatory bowel disease, colitis, diarrhea, hepatitis, acute pancreatitis, a hematologic disease, fever, rigor, pruritus, hypotension, dyspnea, chest discomfort, rash, urticaria, angioedema, wheezing, tachycardia, anaphylaxis, a neurologic disease, an ophthalmologic disease, a pulmonary disease, pneumonitis, a renal disease, rheumatologic disease, a musculoskeletal disease, and combinations thereof.

In some cases, the method further comprises administering to the subject a second dose of the anti-cancer therapy following the administering of the therapeutic composition. In some cases, the second dose of the anti-cancer therapy is at least as high as a first dose of the anti-cancer therapy administered prior to the administering of the therapeutic composition. In some cases, the second dose of the anti-cancer therapy is higher than a first dose of the anti-cancer therapy administered prior to the administering of the therapeutic composition. In some cases, an interval between administration of the first dose and second doses is reduced compared to an interval between consecutive doses of the anti-cancer therapy in a second subject not administered the therapeutic composition. In some cases, the therapeutic composition combines with the anti-cancer therapy to treat a cancer of the subject.

In another aspect, the present disclosure provides a method for increasing the efficacy of an anti-cancer therapy, comprising administering to a subject a therapeutic composition comprising a microbial composition; wherein the subject is treated with the anti-cancer therapy; and wherein the microbial composition comprises a fecal microbiota of a human donor.

In some cases, administering the therapeutic composition maintains or induces responsiveness of a tumor of the subject to the anti-cancer therapy. In some cases, administering the therapeutic composition increases the number or activity of a cell type of the immune system. In some cases, the cell type is selected from the group consisting of: T cells, B cells, dendritic cells, macrophages, neutrophils, NK cells, and combinations thereof. In some cases, administering the therapeutic composition shifts a ratio of immune cells in the subject in favor of a cell type capable of suppressing growth of a tumor. In some cases, the cell type capable of suppressing growth of a tumor is selected from the group consisting of: T cells, cytotoxic T lymphocytes, T helper cells, natural killer (NK) cells, natural killer T (NKT) cells, anti-tumor macrophages, B cells, dendritic cells, and combinations thereof. In some cases, administering the therapeutic composition shifts a ratio of immune cells in the subject against a cell type capable of protecting a tumor. In some cases, the cell type capable of protecting a tumor is selected from the group consisting of: myeloid-derived suppressor cells (MDSCs), regulatory T cells (Tregs), tumor associated neutrophils (TANs), M2 macrophages, tumor associated macrophages (TAMs), and a combination thereof.

In some cases, the anti-cancer therapy comprises an immuno-oncology therapy. In some cases, the immuno-oncology therapy comprises administration to the subject of at least one compound capable of recognizing a tumor-cell antigen and/or a cancer-cell antigen. In some cases, the at least one compound capable of recognizing a tumor-cell antigen and/or a cancer-cell antigen is an engineered protein, a fusion protein, an antibody, or a cytokine. In some cases, the tumor-cell antigen and/or a cancer-cell antigen is selected from the group consisting of: 2B4, 41BB, A2AR, ALK, a B-7 family ligand, BRAF, BTK, BTLA, CCR4, CD19, CD20, CD27, CD28, CD35, CD40, CD50, CD73, CD 137, CD160/By55, CD172a/SIRPα, CD200, CD223, CD244, CEACAM, a CHK 1 kinase, a CHK2 kinase, cMET, CSF1R, CTLA-4, CXCR, DNMT, EGFr, GAL9, GITR, HDAC, HER-2, HVEM, ICOS, IDO, KIR, KRAS, LAG3, MEK, mTor, NKG2A, OX40, PARP, PD-1, PD-L1, PD-L2, STAT3, TGF-beta, TIGIT, TIM-3, TKI, a TLR (Toll like receptors), and combinations thereof. In some cases, the at least one compound is an antibody selected from the group consisting of: nivolumab, pembrolizumab, pidilizumab, RMP1-14, AGEN2034, cemiplimab, ipilimumab, 9D9, tremelimumab, AGEN1884, RG2077, and combinations thereof. In some cases, the immuno-oncology therapy is a cell-based immuno-oncology therapy. In some cases, the cell-based immuno-oncology therapy comprises adoptive cell transfer (ACT) to the subject. In some cases, the ACT is autologous or allogenic. In some cases, a cell used in the cell-based immuno-oncology therapy comprises a Chimeric Antigen Receptor (CAR) or an engineered T Cell Receptor (TCR). In some cases, a cell used in the immuno-oncology therapy is an antigen-presenting cell (APC) or a tumor infiltrating lymphocyte (TIL). In some cases, recognizing a tumor-cell antigen and/or a cancer-cell antigen inhibits downstream signaling of the tumor-cell antigen and/or cancer-cell antigen. In some cases, recognizing a tumor-cell antigen and/or a cancer-cell antigen enhances downstream signaling of the tumor-cell antigen and/or cancer-cell antigen.

In some cases, treatment with the anti-cancer therapy comprises administration of multiple doses of the anti-cancer therapy to the subject. In some cases, the method further comprises administering to the subject a first and second dose of the anti-cancer therapy. In some cases, the first dose of the anti-cancer therapy is administered to the subject prior to administering the therapeutic composition. In some cases, the second dose of the anti-cancer therapy is administered to the subject after administering the therapeutic composition. In some cases, second dose is at least as high as the first dose. In some cases, the second dose is higher than the first dose. In some cases, an interval between administration of the first and second dose is reduced compared to an interval between consecutive doses of the anti-cancer therapy in a second subject not administered the therapeutic composition.

In some cases, the subject is administered the therapeutic composition after treatment with the anti-cancer therapy. In some cases, the therapeutic composition is administered at least 1 day after treatment with the anti-cancer therapy. In some cases, the therapeutic composition is administered at least 3 days after treatment with the anti-cancer therapy. In some cases, the therapeutic composition is administered at least 5 days after treatment with the anti-cancer therapy. In some cases, the therapeutic composition is administered at least 1 week after treatment with the anti-cancer therapy. In some cases, the therapeutic composition is administered at least 4 weeks after treatment with the anti-cancer therapy. In some cases, the therapeutic composition is administered at least 8 weeks after treatment with the anti-cancer therapy. In some cases, the subject is administered the therapeutic composition before treatment with the anti-cancer therapy. In some cases, the therapeutic composition is administered at least 1 day before treatment with the anti-cancer therapy. In some cases, the therapeutic composition is administered at least 3 days before treatment with the anti-cancer therapy. In some cases, the therapeutic composition is administered at least 5 days before treatment with the anti-cancer therapy. In some cases, the therapeutic composition is administered at least 1 week before treatment with the anti-cancer therapy. In some cases, the therapeutic composition is administered at least 4 weeks before treatment with the anti-cancer therapy. In some cases, the therapeutic composition is administered at least 8 weeks before treatment with the anti-cancer therapy. In some cases, the subject is administered the therapeutic composition concurrently with the anti-cancer therapy.

In some cases, the subject has a cancer. In some cases, the cancer is selected from the group consisting of: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer; glioblastoma; hepatic carcinoma; hepatoma; intra-epithelial neoplasm; kidney or renal cancer; larynx cancer; leukemia; liver cancer; lung cancer; melanoma; myeloma; neuroblastoma; oral cavity cancer; ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; urothelial cancer; uterine or endometrial cancer; cancer of the urinary system; vulval cancer; lymphoma; Hodgkin's lymphoma; non-Hodgkin's lymphoma (NHL); B-cell lymphoma; small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's Macroglobulinemia; chronic lymphocytic leukemia (CLL); acute lymphoblastic leukemia (ALL); Hairy cell leukemia; chronic myeloblastic leukemia; other carcinomas and sarcomas; and combinations thereof. In some cases, the cancer is bladder cancer, carcinoma of head and neck, colon and rectum cancer, kidney or renal cancer, melanoma, non-small cell lung cancer, triple-negative breast cancer, or urothelial cancer. In some cases, the cancer is classified as PDL-1+ and/or CTLA4'.

In some cases, the subject is refractory and/or non-responsive to the anti-cancer therapy. In some cases, administering the therapeutic composition results in treatment or inhibition of an oncology treatment-induced condition (OTIC).

In some cases, the fecal microbiota is obtained from a stool sample of the human donor. In some cases, the fecal microbiota is from a single human donor. In some cases, the microbial composition comprises fecal microbiota from multiple human donors. In some cases, the fecal microbiota is a substantially complete fecal microbiota. In some cases, the microbial composition is substantially devoid of fiber. In some cases, the microbial composition further comprises at least one cultured bacterial strain. In some cases, the human donor has recovered from a cancer, in remission from a cancer, and/or previously responded to an anti-cancer therapy. In some cases, the human donor is the subject, and the fecal microbiota is obtained from the subject prior to treatment with the anti-cancer therapy. In some cases, the subject does not show symptoms of a cancer when the fecal microbiota is obtained. In some cases, the human donor is a healthy human donor.

In some cases, the microbial composition comprises lyophilized bacteria. In some cases, the therapeutic composition further comprises a pharmaceutically-acceptable binder, disintegrant, filler, and/or preservative. In some cases, the therapeutic composition is formulated for enteric delivery of the microbial composition. In some cases, the therapeutic composition is administered orally. In some cases, the therapeutic composition comprises a capsule encapsulating the microbial composition. In some cases, the capsule comprises an exterior enteric coating that releases the microbial composition in the ileum or the colon of the subject. In some cases, the capsule releases the microbial composition in the ileum of the subject. In some cases, the exterior enteric coating comprises a compound selected from the group consisting of: methacrylic acid copolymer, cellulose acetate phthalate (CAP), hydroxypropylmethyl cellulose phthalate, polyvinyl acetate phthalate, carboxymethylethylcellulose, and EUDRAGIT®-type polymer (poly(methacrylic acid, methylmethacrylate), hydroxypropyl methylcellulose acetate succinate, cellulose acetate trimellitate, hypromellose (INN) hydroxypropyl methylcellulose (HPMC), shellac, and combinations thereof.

In some cases, the subject is administered an antibiotic and/or a prebiotic prior to administration of the therapeutic composition.

Additional aspects and advantages of the present disclosure will become readily apparent to those skilled in this art from the following detailed description, wherein only illustrative embodiments of the present disclosure are shown and described. As will be understood, the present disclosure is capable of other and different embodiments, and its several details are capable of modifications in various obvious respects, all without departing from the scope of the disclosure.

Accordingly, the description is to be regarded as illustrative in nature, and not as restrictive.

DETAILED DESCRIPTION

Described herein are pharmaceutical compositions containing a microbial composition that can be administered to a cancer patient to produce certain positive or therapeutic effects in the patient. Herein "microbial composition" refers to a prepared mixture of multiple strains of live microorganisms (e.g., bacteria) that can be administered to a patient to give rise to a therapeutic effect. Typically, the microbial compositions described herein contain live bacteria from a fecal microbiota.

In embodiments, administration of a therapeutic composition containing a microbial preparation described herein produces a therapeutic effect in a cancer patient by increasing the efficacy of an anti-cancer therapy. In other embodiments, administration of a therapeutic composition containing a microbial preparation described herein produces a therapeutic effect in a cancer patient by treating, inhibiting, preventing or reducing an oncology-treatment induced condition (OTIC) associated with or arising from an anti-cancer therapy.

Increasing the Efficacy of an Anti-Cancer Therapy

Described herein are compositions and methods for increasing efficacy of an anti-cancer therapy. In one example, a method includes administering a therapeutic composition comprising a microbial composition (with or without an anti-cancer therapeutic agent) and administering an anti-cancer therapy. For example, the anti-cancer therapy comprises surgery, radiation therapy, administration of a chemotherapeutic agent (including hormonal therapy), stem-cell transplant therapy, or targeted therapy (including an immunotherapy).

In embodiments, the microbial composition provides direct onco-therapeutic effects and/or synergistic effects between healthy microbiota and cancer treatments, e.g., occurring via the gut-brain axis. The role of the microbiota in the gut-brain axis is described, for example, in Carabotti, et al., "The gut-brain axis: interactions between enteric microbiota, central and enteric nervous systems" *Annals of Gastroenterology,* 28(2)202-209 (2015), the entire contents of which is incorporated herein by reference in its entirety.

In embodiments, the microbial composition maintains or induces tumor responsiveness to the anti-cancer therapy. For example, the effectiveness of an anti-cancer therapy may wane over time, thereby requiring an increased dose of the therapy (e.g., a chemotherapeutic) to achieve a desired level of therapeutic effect. In this embodiment, the methods disclosed herein maintain and induce, e.g., re-sensitize, the cancer/tumor to the anti-cancer therapy; this allows a reduction of dose or return to the previous dose needed to obtain the desired therapeutic effect. In embodiments, the therapeutic composition rescues an ineffective or deleterious anti-cancer therapy. Here, a cancer is multidrug resistant and the subject may have undergone one or more cycles of chemotherapy, without substantial response. Thus, the methods disclosed herein avoid or limit administration of unnecessary, and potentially harmful, anti-cancer therapies.

In embodiments, the microbial composition boosts the immune system. As an example, the methods disclosed herein increase an innate immune system response relative to a treatment with the anti-cancer therapy alone. Also, the methods increase an adaptive immune system response, such as one or both of humoral immunity and cell-mediated immunity, relative to a treatment with the anti-cancer therapy alone. Further, the methods can increase the number or activity of one or more of T cells, B cells, dendritic cells, macrophages, neutrophils, NK cells relative to a treatment with the anti-cancer therapy alone. The methods may shift the ratio of immune cells in favor of cells that can kill and/or suppress a tumor (e.g., T cells, cytotoxic T lymphocytes, T helper cells, natural killer (NK) cells, natural killer T (NKT) cells, anti-tumor macrophages (e.g., M1 macrophages), B cells, dendritic cells, or subsets thereof)) and in opposition to cells that protect tumors (e.g., myeloid-derived suppressor cells (MDSCs), regulatory T cells (Tregs), tumor associated neutrophils (TANs), M2 macrophages, tumor associated macrophages (TAMs), or subsets thereof) relative to treatments with the anti-cancer therapy alone; for example, the methods increase the ratio of effector T cells to regulatory T cells. The methods may increase secretion of pro-inflammatory cytokines (e.g., interleukin-1 (IL-1), IL-12, and IL-18, tumor necrosis factor (TNF), interferon gamma (IFN-gamma), and granulocyte-macrophage colony stimulating factor) and/or decrease secretion of anti-inflammatory cytokines (e.g., interleukin (IL)-1 receptor antagonist, IL-4, IL-6, IL-10, IL-11, IL-13, interferon alpha (IFN-alpha, and transforming growth factor-beta (TGF-beta)) relative to treatments with the anti-cancer therapy alone.

In embodiments, administration of a composition described herein for increasing the efficacy of an anti-cancer therapy can be carried out concurrently with the anti-cancer therapy. For example, a pharmaceutical composition containing a microbial preparation or composition as described herein may be administered to a patient while the patient is being treated with an anti-cancer therapy (e.g., during the period of a chemotherapeutic or radiation treatment regime, such as between consecutive chemotherapeutic or radiation therapy administrations). In other embodiments, a composition for enhancing the efficacy of an anti-cancer therapy can be administered after the anti-cancer therapy. For example, a pharmaceutical composition containing a microbial preparation or composition as described herein may be administered to a patient after the patient is finished being treated with an anti-cancer therapy (e.g., upon completion of a chemotherapeutic treatment regime). In other examples, a composition for enhancing the efficacy of an anti-cancer therapy can be administered prior to the anti-cancer therapy. For example, a pharmaceutical composition containing a microbial preparation or composition as described herein may be administered to a patient before the patient is treated with an anti-cancer therapy (e.g., before initiation of a chemotherapeutic treatment regime).

In embodiments, a pharmaceutical composition described herein is administered to a subject to enhance efficacy of an anti-cancer therapy on the same day as administration of an anti-cancer therapy. In embodiments, a pharmaceutical composition described herein is administered to a subject to enhance efficacy of an anti-cancer therapy on the day before administration of an anti-cancer therapy. In embodiments, a pharmaceutical composition described herein is administered to a subject to enhance efficacy of an anti-cancer therapy at least 2 days before administration of an anti-cancer therapy. In embodiments, a pharmaceutical composition described herein is administered to a subject to enhance efficacy of an anti-cancer therapy at least 3 days before after administration of an anti-cancer therapy. In embodiments, a pharmaceutical composition described herein is administered to a subject to enhance efficacy of an anti-cancer therapy at least 4 days before administration of an anti-cancer therapy. In embodiments, a pharmaceutical composition described herein is administered to a subject to enhance efficacy of an anti-cancer therapy at least 5 days before administration of an anti-cancer therapy. In embodiments, a pharmaceutical composition described herein is administered to a subject to enhance efficacy of an anti-cancer therapy at least 6 days before administration of an anti-cancer therapy. In embodiments, a pharmaceutical composition described herein is administered to a subject to enhance efficacy of an anti-cancer therapy at least 1 week before the anti-cancer therapy. In embodiments, a pharmaceutical composition described herein is administered to a subject to enhance efficacy of an anti-cancer therapy at least a week before administration of an anti-cancer therapy. In embodiments, a pharmaceutical composition described herein is administered to a subject to enhance efficacy of an anti-cancer therapy at least 2 weeks before administration of an anti-cancer therapy. In embodiments, a pharmaceutical composition described herein is administered to a subject to enhance efficacy of an anti-cancer therapy at least 3 weeks before administration of an anti-cancer therapy. In embodiments, a pharmaceutical composition described herein is administered to a subject to enhance efficacy of an anti-cancer therapy at least 4 weeks before administration of an anti-cancer therapy. In embodiments, a pharmaceutical composition described herein is administered to a subject to enhance efficacy of an anti-cancer therapy at least 5 weeks before administration of an anti-cancer therapy. In embodiments, a pharmaceutical composition described herein is administered to a subject to enhance efficacy of an anti-cancer therapy at least 6 weeks before administration of an anti-cancer therapy. In embodiments, a pharmaceutical composition described herein is administered to a subject to enhance efficacy of an anti-cancer therapy at least 7 weeks before administration of an anti-cancer therapy. In embodiments, a pharmaceutical composition described herein is administered to a subject to enhance efficacy of an anti-cancer therapy at least 8 weeks before administration of an anti-cancer therapy. In embodiments, a pharmaceutical composition described herein is administered to a subject to enhance efficacy of an anti-cancer therapy the day after administration of an anti-cancer therapy. In embodiments, a pharmaceutical composition described herein is administered to a subject to enhance efficacy of an anti-cancer therapy at least 2 days after administration of an anti-cancer therapy. In embodiments, a pharmaceutical composition described herein is administered to a subject to enhance efficacy of an anti-cancer therapy at least 3 days after administration of an anti-cancer therapy. In embodiments, a pharmaceutical composition described herein is administered to a subject to enhance efficacy of an anti-cancer therapy at least 4 days after administration of an anti-cancer therapy. In embodiments, a pharmaceutical composition described herein is administered to a subject to enhance efficacy of an anti-cancer therapy at least 5 days after administration of an anti-cancer therapy. In embodiments, a pharmaceutical composition described herein is administered to a subject to enhance efficacy of an anti-cancer therapy at least 6 days after administration of an anti-cancer therapy. In embodiments, a pharmaceutical composition described herein is administered to a subject to enhance efficacy of an anti-cancer therapy at least 1 week after administration of an anti-cancer therapy. In embodiments, a pharmaceutical composition described herein is administered to a subject to enhance efficacy of an anti-cancer therapy at least 2 weeks after administration of an anti-cancer therapy. In embodiments, a pharmaceutical composition described herein is administered to a subject to enhance efficacy of an anti-cancer therapy at least 3 weeks after administration of an anti-cancer therapy. In embodiments, a pharmaceutical composition described herein is administered to a subject to enhance efficacy of an anti-cancer therapy at least 4 weeks after administration of an anti-cancer therapy. In embodiments, a pharmaceutical composition described herein is administered to a subject to enhance efficacy of an anti-cancer therapy at least 5 weeks after administration of an anti-cancer therapy. In embodiments, a pharmaceutical composition described herein is administered to a subject to enhance efficacy of an anti-cancer therapy at least 6 weeks after administration of an anti-cancer therapy. In embodiments, a pharmaceutical composition described herein is administered to a subject to enhance efficacy of an anti-cancer therapy at least 7 weeks after administration of an anti-cancer therapy. In embodiments, a pharmaceutical composition described herein is administered to a subject to enhance efficacy of an anti-cancer therapy at least 8 weeks after administration of an anti-cancer therapy.

As used herein "increasing efficacy" of anti-cancer therapy is meant, at least, promotion of the desired therapeutic effect of the anti-cancer therapy and/or furtherance towards a desired therapeutic outcome of the anti-cancer therapy. As examples, increasing efficacy may include one or more of shrinking tumor size (including a partial response or complete response), reducing the number of a cancer cells (e.g., hematologic cancer cells in a blood sample), diminishing/eliminating metastases, halting proliferation of cancer cells, lessening the risk of relapse, lowering a cancer's clinical stage and/or grade, increasing the expression of one or more biomarkers associated with a reduction in the number or proliferation of cancer cells, and/or improving quality of life indicators (including disease-free survival) when compared to treatment with the anti-cancer therapy alone. In embodiments, the methods disclosed herein provide a greater reduction in tumor grade, e.g., according to a Tumor; Node involvement, and Metastatic spread (TNM) staging system, than is reduced by a method comprising the anti-cancer therapy alone. For example, over the course of a treatment, a stage IV tumor may be reduced to a stage II tumor, whereas a stage IV tumor may only be reduced to a stage III tumor over the course of a treatment only including the anti-cancer therapy. Similarly, the methods disclosed herein provide greater reduction in cancer stage (which relates to how abnormal the cancer cells appear, how rapidly they proliferate, and how likely they are to metastasize) than by a method comprising the anti-cancer therapy alone. Also, the methods disclosed herein may shrink a tumor's size faster and to a greater extent than would a treatment only including the anti-cancer therapy.

Oncology Treatment Induced Conditions (OTICs)

Described herein are compositions and methods for treating, preventing, inhibiting or reducing an OTIC associated with or caused by an anti-cancer therapy. In one example, a method includes administering a therapeutic composition comprising a microbial composition (with or without an anti-cancer therapeutic agent) and administering an anti-cancer therapy. For example, the anti-cancer therapy comprises surgery, radiation therapy, administration of a chemotherapeutic agent (including hormonal therapy), stem-cell transplant therapy, or targeted therapy (including an immunotherapy). In embodiments, an OTIC of the anti-cancer therapy is caused by gut dysbiosis.

In embodiments, the human subject has undergone and/or is undergoing the anti-cancer therapy and has an OTIC of the anti-cancer therapy. In embodiments, the human subject has undergone and/or is undergoing the anti-cancer therapy and is at risk for developing an OTIC of the anti-cancer therapy. In embodiments, the human subject will undergo the anti-cancer therapy and is at risk for developing an OTIC of the anti-cancer therapy.

In embodiments, the OTIC of the anti-cancer therapy is bleeding related to the cancer.

In embodiments, the OTIC of the anti-cancer therapy is gut dysmotility which causes impaired contraction of muscles in the digestive system, e.g., causing nausea, vomiting, bloating, and/or malnutrition.

In embodiments, the OTIC of the anti-cancer therapy is a cancer-wasting/malnutrition syndrome, e.g., cachexia or sarcopenia.

In embodiments, the OTIC of the anti-cancer therapy is a colitis, e.g., proctitis. In embodiments, the proctitis is radiation proctitis caused by radiation therapy.

In embodiments, the OTIC of the anti-cancer therapy is a disorder related to the gut-brain axis. In embodiments, the disorder related to the gut-brain axis is depression or anxiety. In embodiments, the disorder related to the gut-brain axis is fatigue. As known in the art, fatigue is among the most common OTIC of anti-cancer therapy, with an estimated overall frequency of 16 to 24 percent for the anti-programmed cell death receptor 1 (PD-1) and anti-programmed cell death ligand 1 (PD-L1) agents and approximately 40 percent of those treated with ipilimumab (e.g., YERVOY) experience fatigue.

In embodiments, the OTIC of the anti-cancer therapy is an infection and/or is related to gut dysbiosis. In embodiments, the infection is a viral infection, e.g., in which the virus is a cancer-related virus. In embodiments, the subject is further administered an antiviral compound.

In embodiments, the infection is a bacterial infection, e.g., caused by an antibiotic-resistant bacteria selected from Antibiotic-resistant Proteobacteria, Vancomycin Resistant *Enterococcus* (VRE), Carbapenem Resistant Enterobacteriaceae (CRE), fluoroquinolone-resistant Enterobacteriaceae, or Extended Spectrum Beta-Lactamase producing Enterobacteriaceae (ESBL-E).

In embodiments, the OTIC of the surgery is a surgical wound and/or bleeding related to the surgery.

In embodiments, the OTIC of the chemotherapeutic agent is alopecia.

In embodiments, the OTIC of a stem-cell transplant therapy is a graft-versus-host disease (GVHD).

In embodiments, the OTIC of an immuno-oncology therapy is selected from cardiovascular-related; dermatologic and mucosal-related; endocrinopathies, e.g., autoimmune thyroid disease, hypothyroidism, hyperthyroidism, hypophysitis, thyroiditis, thyrotoxicosis, adrenal insufficiency, and type 1 diabetes mellitus; exocrine pancreas-related; gastrointestinal, e.g., colitis, diarrhea, hepatitis, and acute pancreatitis; hematologic-related; hepatotoxicity; an infusion reaction, e.g., fever, rigor, pruritus, hypotension, dyspnea, chest discomfort, rash, urticaria, angioedema, wheezing or tachycardia, and anaphylaxis; neurologic-related; ophthalmologic-related; pulmonary-related, e.g., pneumonitis and sarcoidosis; pneumonitis; renal-related; and rheumatologic or musculoskeletal-related. In embodiments, the OTIC of the cell-based immuno-oncology therapy is a graft-versus-host disease (GVHD).

In embodiments, treatment or prevention of an OTIC associated with or caused by an anti-cancer therapy can be carried out concurrently with the anti-cancer therapy. For example, a pharmaceutical composition containing a microbial preparation or composition as described herein may be administered to a patient while the patient is being treated with an anti-cancer therapy (e.g., during the period of a chemotherapeutic or radiation treatment regime, such as between consecutive chemotherapeutic or radiation administrations). In other embodiments, treatment or prevention of an OTIC associated with or caused by an anti-cancer therapy can be carried out subsequent to the anti-cancer therapy. For example, a pharmaceutical composition containing a microbial preparation or composition as described herein may be administered to a patient after the patient is finished being treated with an anti-cancer therapy (e.g., upon completion of a chemotherapeutic treatment regime). In other examples, treatment or prevention of an OTIC associated with or caused by an anti-cancer therapy can be carried out prior to the anti-cancer therapy. For example, a pharmaceutical composition containing a microbial preparation or composition as described herein may be administered to a patient before the patient is treated with an anti-cancer therapy (e.g., before initiation of a chemotherapeutic treatment regime). In such instances, administration of a composition described herein can lower a patient's susceptibility to onset of an OTIC as a result of the anti-cancer therapy.

In embodiments, a pharmaceutical composition described herein is administered to a subject to treat or prevent an OTIC on the same day as administration of an anti-cancer therapy. In embodiments, a pharmaceutical composition described herein is administered to a subject to treat or prevent an OTIC on the day before administration of an anti-cancer therapy. In embodiments, a pharmaceutical composition described herein is administered to a subject to treat or prevent an OTIC at least 2 days before administration of an anti-cancer therapy. In embodiments, a pharmaceutical composition described herein is administered to a subject to treat or prevent an OTIC at least 3 days before after administration of an anti-cancer therapy. In embodiments, a pharmaceutical composition described herein is administered to a subject to treat or prevent an OTIC at least 4 days before administration of an anti-cancer therapy. In embodiments, a pharmaceutical composition described herein is administered to a subject to treat or prevent an OTIC at least 5 days before administration of an anti-cancer therapy. In embodiments, a pharmaceutical composition described herein is administered to a subject to treat or prevent an OTIC at least 6 days before administration of an anti-cancer therapy. In embodiments, a pharmaceutical composition described herein is administered to a subject to treat or prevent an OTIC at least 1 week before the anti-cancer therapy. In embodiments, a pharmaceutical composition described herein is administered to a subject to treat or prevent an OTIC at least a week before administration of an anti-cancer therapy. In embodiments, a pharmaceutical composition described herein is administered to a subject to treat or prevent an OTIC at least 2 weeks before administration of an anti-cancer therapy. In embodiments, a pharmaceutical composition described herein is administered to a subject to treat or prevent an OTIC at least 3 weeks before administration of an anti-cancer therapy. In embodiments, a pharmaceutical composition described herein is administered to a subject to treat or prevent an OTIC at least 4 weeks before administration of an anti-cancer therapy. In embodiments, a pharmaceutical composition described herein is administered to a subject to treat or prevent an OTIC at least 5 weeks before administration of an anti-cancer therapy. In embodiments, a pharmaceutical composition described herein is administered to a subject to treat or prevent an OTIC at least 6 weeks before administration of an anti-cancer therapy. In embodiments, a pharmaceutical composition described herein is administered to a subject to treat or prevent an OTIC at least 7 weeks before administration of an anti-cancer therapy. In embodiments, a pharmaceutical composition described herein is administered to a subject to treat or prevent an OTIC at least 8 weeks before administration of an anti-cancer therapy. In embodiments, a pharmaceutical composition described herein is administered to a subject to treat or prevent an OTIC the day after administration of an anti-cancer therapy. In embodiments, a pharmaceutical composition described herein is administered to a subject to treat or prevent an OTIC at least 2 days after administration of an anti-cancer therapy. In embodiments, a pharmaceutical composition described herein is administered to a subject to treat or prevent an OTIC at least 3 days after administration of an anti-cancer therapy. In embodiments, a pharmaceutical composition described herein is administered to a subject to treat or prevent an OTIC at least 4 days after administration of an anti-cancer therapy. In embodiments, a pharmaceutical composition described herein is administered to a subject to treat or prevent an OTIC at least 5 days after administration of an anti-cancer therapy. In embodiments, a pharmaceutical composition described herein is administered to a subject to treat or prevent an OTIC at least 6 days after administration of an anti-cancer therapy. In embodiments, a pharmaceutical composition described herein is administered to a subject to treat or prevent an OTIC at least 1 week after administration of an anti-cancer therapy. In embodiments, a pharmaceutical composition described herein is administered to a subject to treat or prevent an OTIC at least 2 weeks after administration of an anti-cancer therapy. In embodiments, a pharmaceutical composition described herein is administered to a subject to treat or prevent an OTIC at least 3 weeks after administration of an anti-cancer therapy. In embodiments, a pharmaceutical composition described herein is administered to a subject to treat or prevent an OTIC at least 4 weeks after administration of an anti-cancer therapy. In embodiments, a pharmaceutical composition described herein is administered to a subject to treat or prevent an OTIC at least 5 weeks after administration of an anti-cancer therapy. In embodiments, a pharmaceutical composition described herein is administered to a subject to treat or prevent an OTIC at least 6 weeks after administration of an anti-cancer therapy. In embodiments, a pharmaceutical composition described herein is administered to a subject to treat or prevent an OTIC at least 7 weeks after administration of an anti-cancer therapy. In embodiments, a pharmaceutical composition described herein is administered to a subject to treat or prevent an OTIC at least 8 weeks after administration of an anti-cancer therapy.

As used herein an "oncology-treatment induced condition (OTIC)" of anti-cancer therapy is meant, at least, an undesirable consequence and/or non-therapeutic effect caused by or related to the anti-cancer therapy. The OTIC places a subject in a less healthy condition than without s/he would be without the OTIC. This less heathy condition inhibits the furtherance towards a desired therapeutic outcome of the anti-cancer therapy since the subject's systems are not in an ideal state to fight the cancer and may lengthen the treatment time required until recovery and/or increased doses/treatment numbers of the anti-cancer therapy. In embodiments, an OTIC is synonymous with "side effect". Moreover, the OTIC may have long-term effects that last beyond when the cancer has been treated. Examples of such long-term effects include cardiovascular disorders (including Congestive heart failure (CHF), Coronary artery disease, and hypertension); lung disorders; endocrine (hormone) system disorders (including diabetes, hypothyroidism, menopause, and metabolic syndrome); bone, joint, and soft tissue disorders; digestive disorders; hair loss; kidney disorders; dental and oral problems; brain, spinal cord, and nerve disorders; and secondary cancers.

An OTIC as described herein refers to a condition that is induced in a subject by administration of an anti-cancer therapy to the subject. Herein the term "induced" when used with respect to the relation between an anti-cancer therapy and an OTIC encompasses both a condition caused by administration of an anti-cancer therapy or a pre-existing condition in a subject that is exacerbated by an anti-cancer therapy. In embodiments, a subject treated with an anti-cancer therapy did not show symptoms of an OTIC prior to administration of the anti-cancer therapy. In embodiments, a subject treated with an anti-cancer therapy had not previously been diagnosed with an OTIC. In embodiments, an OTIC described herein is caused by administration of an anti-cancer therapy to a subject. In other embodiments, a subject treated with an anti-cancer therapy showed symptoms of an OTIC prior to administration of the anti-cancer therapy, and administration of the anti-cancer therapy exacerbated or worsened one or more symptoms, or resulted in the appearance of additional symptoms not present prior to the anti-cancer therapy. In embodiments, a subject administered an anti-cancer therapy did not show symptoms of an OTIC immediately prior to treatment with the anti-cancer therapy, showed symptoms of the OTIC in the past. For example, in embodiments, a subject administered an anti-cancer therapy did not show symptoms of an OTIC immediately prior to treatment with the anti-cancer therapy, but showed symptoms of the OTIC in the past 6 months, 1 year, 1.5 years, 2 years, 3 years, or 5 years. In embodiments, an OTIC induced by treatment with an anti-cancer therapy results in the flaring up or reappearance of a latent condition in the subject.

In embodiments, administration of a composition described herein to treat an OTIC in a subject administered an anti-cancer therapy may enhance the efficacy of further administrations of the anti-cancer therapy. In embodiments, the therapeutic composition comprising a microbial composition permits, relative to a subject who has not or will not be administered a therapeutic composition comprising a microbial composition, (i) the same dose or an increased dose of the anti-cancer therapy per treatment; (ii) increased numbers of treatment doses of the anti-cancer therapy; and/or (iii) reduced intervals between doses of the anti-cancer therapy. By reducing dose-limiting toxicities of cancer treatments, a subject can tolerate more potent/aggressive anti-cancer therapeutics. In other embodiments, administration of a composition described herein to treat an OTIC in a subject administered a first anti-cancer therapy may permit the administration of a second anti-cancer therapy different from the first.

Anti-Cancer Therapies

In embodiments, the anti-cancer therapy can be surgery which excises a tumor or an organ/tissue comprising cancerous cells.

In embodiments, the anti-cancer therapy comprises administration of a chemotherapeutic agent. The chemotherapeutic agent may be selected from alkylating agents such as thiotepa and Cytoxan cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII); dynemicin, including dynemicin A; bisphosphonates, such as clodronate; an esperamicin; neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate;

purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("AraC"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chlorambucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-α, Raf, H-Ras, EGFR (e.g., erlotinib (Tarceva)) or VEGF-A that reduce cell proliferation, and pharmaceutically acceptable salts, acids or derivatives of any of the above.

In embodiments, the anti-cancer therapy is a stem-cell transplant therapy comprising a peripheral blood transplant, a bone marrow transplant, a cord blood transplant, or a skin-derived stem cell transplant.

In embodiments, the anti-cancer therapy is a targeted therapy. For example, the targeted therapy may be an immuno-oncology therapy that comprises at least one molecule capable of binding and/or recognizing a tumor-cell antigen and/or a cancer-cell antigen; the at least one molecule capable of binding and/or recognizing a tumor-cell antigen and/or a cancer-cell antigen may be an engineered protein, a fusion protein, an antibody, or a cytokine. In embodiments, the tumor-cell antigen and/or a cancer-cell antigen is 2B4, 41BB, A2AR, ALK, B-7 family ligands (including, but are not limited to, B7-1, B7-2, B7-DC, B7-H1, B7-H2, B7-H3, B7-H4, B7-H5, B7-H6 and B7-H7), BRAF, BTK, BTLA, CCR4, CD19, CD20, CD27, CD28, CD35, CD40, CD50, CD73, CD137, CD160/By55, CD172a/SIRPα, CD200, CD223, CD244, CEACAM, CHK 1 and CH K2 kinases, cMET, CSF1R, CTLA-4, CXCR, DNMT, EGFr, GAL9, GITR, HDAC, HER-2, HVEM, ICOS, IDO, KIR, KRAS, LAG3, MEK, mTor, NKG2A, OX40, PARP, PD-1, PD-L1, PD-L2, STAT3, TGF-beta, TIGIT, TIM-3, TKI, TLR (Toll like receptors, e.g., TLR9 & TLR8), TMIGD2, VEGF, VISTA/VSIG8, and its ligand or receptor thereof. In embodiments, the at least one molecule binds to and/or recognizes the tumor-cell antigen and/or a cancer-cell antigen selected from CTLA-4, PD-1, PD-L1, and PD-L2.

In embodiments, the immuno-oncology therapy comprises an antibody selected from the group consisting of nivolumab (ONO 4538, BMS 936558, MDX1106, OPDIVO (Bristol Myers Squibb)), pembrolizumab (KEYTRUDA/MK 3475, Merck), pidilizumab (CT 011, Cure Tech), RMP1-14, AGEN2034 (Agenus), and cemiplimab ((REGN-2810), ipilimumab (YERVOY), 9D9, tremelimumab (formerly ticilimumab, CP-675,206; MedImmune), AGEN1884, and RG2077. In embodiments, the antibody is KEYTRUDA (Pembrolizumab), OPDIVO (Nivolumab), or YERVOY (Ipilimumab).

In embodiments, the anti-cancer therapy comprises an immuno-oncology therapy, e.g., comprising binding and/or recognizing a checkpoint molecule, e.g., PD-1, PD-L1, PD-L2, ICOS, ICOSL, and CTLA-4. In embodiments, the immuno-oncology therapy comprises administration of KEYTRUDA (Pembrolizumab), OPDIVO (Nivolumab), or YERVOY (Ipilimumab).

In embodiments, the immuno-oncology therapy comprises a cell-based immuno-oncology therapy, e.g., relating to adoptive cell transfer (ACT). In embodiments, the ACT is autologous or allogenic. In embodiments, the cell-based immuno-oncology therapy is a Chimeric Antigen Receptor (CAR) T-cell therapy, is an antigen-presenting cell (APC)-related therapy, comprises use of engineered T Cell Receptors (TCR), or comprises use of tumor infiltrating lymphocytes (TIL).

In embodiments, the immuno-oncology therapy comprises binding and/or recognizing a tumor-cell antigen and/or a cancer-cell antigen which blocks and/or prevents downstream signaling of the tumor-cell antigen and/or cancer-cell antigen.

In embodiments, the immuno-oncology therapy comprises binding and/or recognizing a tumor-cell antigen and/or a cancer-cell antigen which activates and/or stimulates downstream signaling of the tumor-cell antigen and/or cancer-cell antigen.

In embodiments, the targeted therapy comprises a STING agonist, e.g., 5,6-dimethylxanthenone-4-acetic acid (DMXAA), MIW815(ADU-S100), or MK-1454.

In embodiments, the targeted therapy comprises an interleukin, e.g., IL-21 or IL-15.

In embodiments, the subject is refractory and/or non-responsive to an anti-cancer therapy, e.g., directed to a checkpoint molecule and, optionally, comprises administration of KEYTRUDA (Pembrolizumab), OPDIVO (Nivolumab), or YERVOY (Ipilimumab).

In embodiments, a targeted therapy involves administration of a small molecule that is not an antibody to inhibit tumor growth. Examples of small molecules include but are not limited to Axitinib (Inlyta), Batimastat (BB-94), Bortezomib (Velcade), Bosutinib (Bosulif), Cabozantinib (Cometriq), Carfilzomib (Kyprolis), Crizotinib (Xalkori), Erlotinib (Tarceva), Everolimus (afinitor), Ganetespib, Gefitinib (Iressa), Ibrutinib (Imbruvica), Imatinib (Gleevec), Lapatinib (Tykerb), Marimastat (BB-2516), Marizomib (NPI-0052), Navitoclax (ABT-263), Neovastat (AE-941), Nilotinib (Tasigna), NVP-AUY922, Obatoclax (GX15-070), Pazopanib (Votrient), Perifosine, Ponatinib (Iclusig), Prinomastat (AG-3340), Rebimastat (BMS-275291), Regorafenib (Stivagra), Ruxolitinib (jafaki), Seliciclib (roscovitine or CYC202), Sorafenib (Nexavar), Sunitinib (sutent), Temsirolimus (CCI-779), Trametinib (Mekinist), and Vandetenib (Caprelsa).

Donor Pre-Screening

In embodiments, the starting material for microbial compositions comprising fecal microbiota disclosed herein is donated feces from one screened human donor or more than one screened human donor (e.g., multiple human donors).

In embodiments, potential donors are screened via: (1) Initial Preliminary Screen. Prior to enrollment, potential donors (e.g., aged about 18 to about 50) undergo a preliminary screen comprising a subset of questions selected from a Donor Health Questionnaire (DHQ) to assess eligibility and/or (2) In-Person Donor Interview. If the potential donor passes the initial preliminary screen, he/she conducts in-person interview and clinical assessment with a healthcare professional. As part of this interview the potential donor completes informed consent and a donor affidavit attesting to provide true, accurate, and complete information. The DHQ, in-person interview, and clinical assessment determine the potential donor's eligibility as a donor.

The DHQ and clinical assessment identify relevant criteria which would preclude one from being a donor (e.g., temporarily and permanently). Three categories of criteria covered by a DHQ include: (1) Infectious risk factors, e.g., risk for factors for multi-drug resistance organisms (MDROs); antibiotic resistant bacteria (ARB); high-risk sexual behaviors; social history, including illicit drug use; high-risk travel history (including a 12-month exclusion if a potential donor has traveled to a high-risk or very high-risk area, as defined by current International SOS (ISOS) guidelines); (2) potential microbiome-mediated conditions and general health status, e.g., gastrointestinal comorbidities; metabolic comorbidities; neurological comorbidities; psychiatric comorbidities; chronic pain syndromes; infectious diseases; autoimmune diseases; atopy, asthma and allergies (food and other); malignancy; surgeries/other medical history; current symptoms (including stool habits); medications including antimicrobial therapy; diet; and family history; and (3) pregnancy and breastfeeding status, for potential female donors. In embodiments, the clinical assessment includes, as examples, determination of vital signs including temperature, blood pressure, heart rate, respiratory rate, waist circumference, and body mass index (BMI).

In embodiments, the DHQ is analogous to that used by the Red Cross for screening potential blood donors (with fewer or additional questions, if desired).

Potential donors who are eligible to be donors based upon their DHQ, in-person interview results, and clinical assessment then undergo a series of serological, stool, and nasal swab screens/tests. Serological, stool, and nasal swab testing/screening are performed in conjunction with a diagnostic laboratory, e.g., a Clinical Laboratory Improvement Amendments (CLIA)-certified diagnostic laboratory.

Table 1 provides an overview of illustrative serological, stool, and nasal swab screens/tests conducted as part of the donor screening process of embodiments. Screening/testing is performed under conditions well-known in the art, such as, by way of non-limiting example: Hepatitis C may be detected by an immunoassay (IA), Shiga may be detected by enzyme immunoassay (EIA), and *Clostridium difficile* may be detected by real-time polymerase chain reaction (RT-PCR).

TABLE 1

Illustrative Serological, Stool, and Nasal Swab Screens/Tests

| | Pathogen | |
|---|---|---|
| Serological Testing | HIV 1/2 | |
| | Hepatitis A | |
| | Hepatitis B | |
| | Hepatitis C | |
| | *Treponema pallidum* | |
| | *Strongyloides* | |
| Stool Testing | Multi-Drug | VRE |
| | Resistant | CRE |
| | Organisms | FRE |
| | | ESBL |
| | *Salmonella* spp | |
| | *Shigella* spp | |
| | *Campylobacter* spp | |
| | *Vibrio* spp | |
| | Rotavirus A | |
| | *Cryptosporidium* spp | |
| | Shiga | |
| | *Giardia lamblia* | |
| | Adenovirus | |
| | Norovirus | |
| | *Clostridium difficile* (e.g., a producer of Toxin B) | |
| | *Cryptosporidium* spp | |
| | *Helicobacter pylori* | |
| | Ova and parasites | |
| | *Cyclospora* and *Isospora* | |
| | Microsporidia | |
| | Bristol Stool Type assessment | |
| Nasal Swab | Multi-Drug | VRE |
| | Resistant | CRE |
| | Organisms | FRE |
| | | MRSA |
| | | ESBL |

VRE = Vancomycin-resistant enterococci; CRE = carbapenem-resistant Enterobacteriaceae; ESBL = Extended-spectrum beta-lactamases; FRE = fluoroquinolone-resistant Enterobacteriaceae.

In embodiments, a potential donor is excluded if he/she has a positive result in a test/screen for an infectious disease, e.g., caused by one of the pathogens listed in Table 1. In embodiments, a potential donor who tests positive for HIV-1/2, Hepatitis B, or Hepatitis C is indefinitely excluded from donating.

In embodiments, a potential donor who tests positive for Hepatitis A, *Treponema pallidum*, or *Strongyloides* is deferred from donating until eight weeks after a successful treatment has been completed, symptoms have resolved, and no recurrence of symptoms have occurred.

In embodiments, a potential donor who tests positive for Adenovirus, *Campylobacter* spp, *Clostridium difficile* toxin B, *Cryptosporidium* spp, *Cyclospora* and *Isospora*, *Giardia lamblia*, *Proteus*, *Morganella*, *Helicobacter* Microsporidia, *Norovirus*, *Ova and parasites*, *Salmonella* spp, Shiga, *Shigella* spp, or *Vibrio* spp, is immediately placed on hold and deferred for eight weeks from symptom resolution, completion of treatment, and no recurrence. Screened donors deferred for eight weeks from symptom resolution, completion of treatment, and no recurrence due to any of the above may undergo a full repeat screen to evaluate for inclusion.

In embodiments, a potential donor who tests positive for rotavirus is placed immediately on donation hold and undergoes repeat confirmatory testing. If confirmed positive, these donors are ineligible for donation for eight weeks. Screened donors deferred for eight weeks due to rotavirus may undergo a full repeat screen to evaluate for inclusion.

In embodiments, a potential donor who tests positive for a Multi-Drug Resistant Organism (MDROs) or an antibiotic resistant bacteria (ARB), e.g., Vancomycin-resistant *Enterococcus* (VRE), Carbapenem-resistant enterobacteriaceae (CRE), fluoroquinolone-resistant Enterobacteriaceae (FRE), and Extended-spectrum beta-lactamase (ESBL) is immediately placed on hold and deferred for eight weeks after successful treatment/decolonization with no symptoms or recurrence. Screened donors deferred for eight weeks after successful treatment/decolonization with no symptoms or recurrence due to any of the above may undergo a full repeat screen to evaluate for inclusion.

In embodiments, a potential donor who tests positive for Methicillin-resistant *Staphylococcus aureus* (MRSA) is immediately placed on hold and deferred for eight weeks after successful treatment/decolonization with no symptoms or recurrence. Screened donors deferred for eight weeks after successful treatment/decolonization with no symptoms or recurrence due to any of the above may undergo a full repeat screen to evaluate for inclusion.

In embodiments, potential donors may submit samples for additional screening which may include assays for Liver Function Panel, Alanine Aminotransferase (ALT), Aspartate Aminotransferase (AST), Alkaline Phosphatase (ALP), Albumin, Bilirubin (Total, direct, or indirect), and Complete Blood Count (CBC) with Differential. Donors whose results from these Additional Screening assays are outside the bounds of normal (see, e.g., Table 2) are likely ineligible to donate stool.

TABLE 2

Illustrative Low limit and High limit for Complete Blood Count (CBC) and Hepatic Function Panel (HFP)

| Test | Category | Low | High | Units |
|---|---|---|---|---|
| CBC | WBC | 3.8 | 10.8 | ×10³/µL |
| CBC | RBC | 4.20 | 5.80 | ×10⁶/µL |
| CBC | Hemoglobin | 13.2 | 17.1 | g/dL |
| CBC | Hematocrit | 38.5 | 50.0 | % |
| CBC | MCV | 80 | 100 | fL |
| CBC | MCH | 27.0 | 33.0 | pg |
| CBC | MCHC | 32.0 | 36.0 | g/dL |
| CBC | RDW | 11 | 15 | % |
| CBC | Platelets | 140 | 400 | ×10³/µL |
| CBC | MPV | 7.5 | 11.5 | fL |
| CBC | Absolute Neutrophils | 1500 | 7800 | cells/µL |
| CBC | Absolute Lymphocytes | 850 | 3900 | cells/µL |
| CBC | Absolute Monocytes | 200 | 950 | cells/µL |
| CBC | Absolute Eosinophils | 15 | 500 | cells/µL |
| CBC | Absolute Basophils | 0 | 200 | cells/µL |
| HFP | Protein, Total, Serum | 6.1 | 8.1 | g/dL |
| HFP | Albumin, Serum | 3.6 | 5.1 | g/dL |
| HFP | Bilirubin, Total | 0.2 | 1.2 | mg/dL |
| HFP | Bilirubin, Direct | 0.00 | 0.20 | mg/dL |
| HFP | Bilirubin, Indirect | 0.2 | 1.2 | mg/dL |
| HFP | Alkaline Phosphatase, | 40 | 115 | U/L |
| HFP | AST (SGOT) | 10 | 40 | U/L |
| HFP | ALT (SGPT) | 9 | 46 | U/L |

If the cause of abnormal assay results is found to be either infectious or may otherwise compromise the health of the donor or an FMT recipient, that donor may be excluded from donating stool for clinical use. If the cause of the abnormal reading is determined to be not clinically significant and to pose no threat to an FMT recipient, as examples, the result is an incidental artifact or due to Gilbert's syndrome, then the donor may be considered for enrollment/re-enrollment.

Other screens or tests may also be used to exclude or include potential donors.

In embodiments, a potential donor may be positive for one or both of Cytomegalovirus (CMV) and Epstein-Barr Virus (EBV). There have not been any reported cases of CMV or EBV infection among those who have received FMT from adult donors (Wang et al. 2016), including a large series of immunocompromised patients (Kelly et al. 2014) and solid organ transplant patients (Fischer et al. 2017).

In embodiments, a potential donor may be positive for *Listeria monocytogenes*. In embodiments, donated material and/or serological samples are not tested for *L. monocytogenes* unless the donor is symptomatic for a *L. monocytogenes* infection.

In embodiments, a potential donor is further screened by analyzing a fecal sample or a blood sample provided by the donor for the presence of specific microorganisms, metabolites, and/or biomarkers. Examples of metabolites and/or biomarkers include Short-Chain Fatty Acids (SCFAs), TNF, IL-10, IL-1, a neurotransmitter (e.g., serotonin and GABA), leptin, adiponectin, and proteins involved in glycan biosynthesis or bile acid biosynthesis.

In embodiments, a potential donor is further screened by analyzing a fecal sample provided by the donor for the presence of a specific bacterial strain that is relevant to the treatment of a cancer.

In embodiments, a potential human donor has recovered from a cancer or is in remission from a cancer. In embodiments, a potential human donor is in remission from a cancer and previously responded to an anti-cancer therapy.

In embodiments, a subject is administered a fecal microbiota collected from the subject prior to undergoing treatment with the anti-cancer therapy (i.e., the subject is the donor of the administered fecal microbiota). In this embodiment, a fecal microbiota of a subject is collected and "banked" before the subject undergoes an anti-cancer therapy, and the fecal microbiota is administered to the subject while undergoing or after undergoing the anti-cancer therapy. In other words, the administration is autologous using a fecal microbiota collected before treatment with the anti-cancer therapy. Here, the goal is to return the subject's microbiome to the diversity that existed prior to the anti-cancer therapy.

Donation Process

In some embodiments, before or after a stool donation event, the pre-screened donor completes a DHQ. A donor's eligibility will be further evaluated should he/she have any positive responses in this questionnaire. If the donor's responses indicate any changes in health status that involve an exclusion criterion, the donated material is discarded. When the donor's DHQ results do not indicate exclusion, the container and the stool material contained therein is processed.

In embodiments, feces used as a source for the fecal microbiota generally has satisfied one or more tests of appearance, potency, pH, water content, and absence of specific infectious agents.

In some embodiments, a donor may complete an in-person clinical health check around the time of a stool donation to ensure the donor's health. If the donor does not have good/optimal health, the donated material may be discarded.

In some embodiments, a donor is generally of good health and has microbiota consistent with such good health. Often, the donor has not been administered an antibiotic compound within a certain period prior to a stool donation.

In some embodiments, the donor does not have irritable bowel disease (e.g., Crohn's disease and ulcerative colitis), irritable bowel syndrome, celiac disease, colorectal cancer, or a family history of these diseases.

In some embodiments, a donor is selected for the presence of certain genera and/or species that provide increased efficacy of therapeutic compositions containing these genera or species. In some embodiments, a preferred donor donates stool material having a relatively high concentration of spores. In some embodiments, a preferred donor donates stool material comprising spores having increased efficacy.

In some embodiments, a donor is selected for the presence of certain genera and/or species that prevent or reduce an OTIC of an anti-cancer therapy. In some embodiments, a preferred donor donates stool material having a relatively high concentration of spores. In some embodiments, a preferred donor donates stool material comprising which prevent or reduce an OTIC of an anti-cancer therapy.

In some embodiments, a sample of a donated stool material or a donated stool may be used for Additional Screening. Additional Screening may include assays for Liver Function Panel, Alanine Aminotransferase (ALT), Aspartate Aminotransferase (AST), Alkaline Phosphatase (ALP), Albumin, Bilirubin (Total, direct, indirect), and Complete Blood Count (CBC) with Differential. Donors whose results from these Additional Screening assays are outside the bounds of normal (see, e.g., Table 2) the donated material may be discarded.

Other screens or tests may also be used to temporarily or permanently exclude donors.

In embodiments, donated material will be screened, using standard microbiological assays, for the presence of infectious agents. Donated material containing infectious agents may be discarded.

In some embodiments, a donor who tests positive for Hepatitis A, *Treponema pallidum*, or *Strongyloides* is deferred from donating until eight weeks after a successful treatment has been completed, symptoms have resolved, and no recurrence of symptoms have occurred. Impacted donated material will be destroyed. Screened donors deferred for eight weeks from symptom resolution, completion of treatment, and no recurrence due to any of the above may undergo a full repeat screen to evaluate his/her return as a donor.

In some embodiments, a donor who tests positive for Adenovirus, *Campylobacter* spp, *Clostridium difficile* toxin B, *Cryptosporidium* spp, *Cyclospora* and *Isospora*, *Giardia lamblia*, *Proteus*, *Morganella*, *Helicobacter pylori*, Microsporidia, Norovirus, Ova and parasites, *Salmonella* spp, Shiga, *Shigella* spp, or *Vibrio* spp, is immediately placed on hold and deferred for eight weeks from symptom resolution, completion of treatment, and no recurrence. Impacted donated material will be discarded. Screened donors deferred for eight weeks from symptom resolution, completion of treatment, and no recurrence due to any of the above may undergo a full repeat screen to evaluate his/her return as a donor.

In some embodiments, a donor who tests positive for rotavirus will be placed immediately on donation hold and have repeat confirmatory testing performed. If confirmed positive, these donors will have their donated material discarded and will be ineligible for donation for eight weeks. Screened donors deferred for eight weeks due to rotavirus may undergo a full repeat screen to evaluate his/her return as a donor.

A donor who tests positive for a Multi-Drug Resistant Organism (MDROs) or an antibiotic-resistant bacteria (ARB), e.g., Vancomycin-resistant *Enterococcus* (VRE), Carbapenem-resistant enterobacteriaceae (CRE), fluoroquinolone-resistant Enterobacteriaceae (FRE) and Extended-spectrum beta-lactamase (ESBL) is immediately placed on hold and deferred for eight weeks after successful treatment/decolonization with no symptoms or recurrence. Impacted donated material will be discarded. Screened donors deferred for eight weeks after successful treatment/decolonization with no symptoms or recurrence due to any of the above may undergo a full repeat screen to evaluate his/her return as a donor.

In some embodiments, a donor who tests positive for Methicillin-resistant *Staphylococcus aureus* (MRSA) is immediately placed on hold and deferred for eight weeks after successful treatment/decolonization with no symptoms or recurrence. Impacted donated material will be discarded. Screened donors deferred for eight weeks after successful treatment/decolonization with no symptoms or recurrence due to any of the above may undergo a full repeat screen to evaluate his/her return as a donor.

In some embodiments, a donor may be positive for one or both of Cytomegalovirus (CMV) and Epstein-Barr Virus (EBV). There have not been any reported cases of CMV or EBV infection among those who have received FMT from adult donors (Wang et al., 2016), including a large series of immunocompromised patients (Kelly et al., 2014) and solid organ transplant patients (Fischer et al., 2017).

In some embodiments, a donor undergoes a blood test about twenty-one days, e.g., two weeks to a month, or longer, after his/her last donation to account for HIV seroconversion.

In some embodiments, a donor may be positive for *Listeria monocytogenes*. In embodiments, donated material and/or serological samples are not tested for *L. monocytogenes* unless the donor is symptomatic for a *L. monocytogenes* infection.

The donor may pass the stool into a container, e.g., a commode specimen collector. In some embodiments, the container's lid is sealed and/or placed in a resealable plastic bag as secondary containment.

At donation delivery, a donor certifies that he/she passed the stool.

At donation delivery, a donor presents an identification card that includes the donor's identity code, which is correlated with all records related to donations by a donor.

Each container is identifiable by a collection of numbers, letter, symbols, or a combination thereof; mark; microchip; and/or barcode that will, at least, associate the container with the donor and the specific donation from the donor.

The date and time of donation is noted and/or the date and time of delivery to the suitable facility is noted.

In some embodiments, a container is secured into a secondary containment (e.g., bag) and/or a tertiary containment. In embodiments, the secondary and/or tertiary containment may be a tamper-evident transport bag.

The mass of the donated material may be measured, for example, by subtracting the mass of an empty container and any secondary or tertiary containment (e.g., bag or bags) from the container and containments comprising the donated material.

In embodiments, processing of a donated material begins within six hours of passage of stool material. Elapsed time prior to stool processing may be noted.

In embodiments, containers comprising donated material may be transferred to a biosafety cabinet, e.g., a sanitized biosafety cabinet that has been cleaned/sterilized with a broad-spectrum disinfectant (which may act as a sporicidal) and/or sterilized with UV. In embodiments, donated material will be visual inspected, within the biosafety cabinet, using the Bristol stool scale and/or for hematochezia, melena, mucus, and/or steatorrhea. Collection of samples from the donated material may occur within the biosafety cabinet.

In embodiments, donated material will be assessed, outside a biosafety cabinet, using the Bristol stool scale and/or for hematochezia, melena, mucus, and/or steatorrhea. Collection of samples from the donated material may occur outside a biosafety cabinet.

Stool below Bristol Type 3 and stool above Bristol Type 5 is discarded.

Stool exhibiting signs of hematochezia, melena, mucus, and/or steatorrhea can be discarded.

In some embodiments, donated material is quarantined (i.e., not included in a drug substance and/or not included in a drug product) for a "collection window" of about sixty days, e.g., thirty to ninety days, and until the donor has passed a second DHQ, a second in-person clinical assessment, and/or a second set of serological, stool, and/or nasal swab tests (as described above). See, Table 3.

TABLE 3

Donor Screening/Testing

| | | Testing Time Points | |
|---|---|---|---|
| Parameter | Acceptance Criteria | Start of collection window | End of collection window |
| Questionnaire & Interview | Pass | x | x |
| Serological | Negative for a panel of Infectious Diseases | x | x |
| Stool | Negative for a panel of Viruses, Enteric Pathogens, Parasites, etc. | x | x |
| MDRO or ARB | Negative for a panel of Multi-Drug Resistant Organisms | x | x |
| Additional Screening | "Normal" for a Liver Function panel and Complete Blood Count & Differential [b] | x | x |
| Donor Health Questionnaire (DHQ) completed at Delivery [a] | No issues noted that involve Exclusion Criteria | x | x |

[a] In addition to the DHQ, if a donor experiences any abnormal symptoms, including a change in bowel habits or change in other relevant clinical factors (e.g., medicines and medical history) donors should notify to the donation facility immediately. A full health assessment is conducted and if symptoms would lead to stool that may impact the health of an FMT recipient, donation is suspended until an examination of the underlying symptoms is initiated by clinical assessment and/or diagnostic tests on stool and/or blood. The impacted material may be discarded. In the event of transient, self-limiting, mild symptoms, donors may be eligible when symptoms resolve.
[b] See, Table 2

TABLE 4

Physical Testing Conducted on Donated Material

| Parameter | Acceptance Criteria | Justification |
|---|---|---|
| Bristol Stool Type | Bristol Stool Type must be Type 3, 4, or 5 | Bristol Stool Type of 2, 3, 4, and 5 are considered healthy. Types above that range (i.e. Type 6 and 7) indicate diarrhea; these Stool Types are not processed. Stool with a Bristol Stool Type 1 or 2, which indicates constipation, may be too rigid or dense for readily processing; these Stool Types are not processed. |
| Screening of Stool for Hematochezia | Hematochezia Visually Absent | The presence of fresh blood in stool indicates lower gastrointestinal pathology (e.g., diverticulosis and inflammatory bowel disease) or, less commonly, a brisk upper gastrointestinal bleed. Stool with hematochezia is not processed. |

TABLE 4-continued

Physical Testing Conducted on Donated Material

| Parameter | Acceptance Criteria | Justification |
|---|---|---|
| Screening of Stool for Melena | Melena Visually Absent | The presence of melena in stool indicates upper gastrointestinal bleeding (e.g., peptic ulcer disease, gastritis, and esophageal varices). Stool with melena is not processed. |
| Screening of Stool for Mucus | Mucus Visually Absent | Although small amounts of mucus are normal, the presence of mucus in stool potentially indicates gastrointestinal pathology (e.g., inflammatory bowel disease and malignancy). Stool with mucus is processed. |
| Screening of Stool for Steatorrhea | Steatorrhea Visually Absent | The presence of steatorrhea in stool indicates fat malabsorption (e.g., pancreatic insufficiency). Stool with steatorrhea is not processed. |

In some embodiments, the viability of the microbiota of the donated stool may be confirmed by culturing a sample of the donated stool, an otherwise purified form of the donated stool, a filtrate, a homogenized product, a thawed-frozen intermediate, a pooled material, and/or a drug substance. Methods for culturing microbiota from stool or from stool-derived products are well-known in the art. In some embodiments, a microbiota is cultured using the Center for Disease Control (CDC) plate, commonly referred to as "CDC Anaerobe 5% Sheep Blood Agar plate, which allows for the isolation and cultivation of fastidious and slow-growing obligatory anaerobic bacteria, the *Bacteroides* Bile Esculin Agar (BBE) plate, which is a specific indicator species media for *Bacteroides*, or GIFU Anaerobic Medium Agar (GAA). In some embodiments, the number of viable, culturable cells within the stool or stool-derived products may be confirmed by the presence of a colony forming unit (CFU) counts, e.g., by the Drop Plate CFU Assay. The diversity of the living microbes in the stool or from stool-derived products may be assayed. The mix of microbes present, or diversity of microbes, is a further measure of the quality of the donated stool and the drug substance.

In some embodiments, the viability of the microbiota of the donated stool may be confirmed by PMAseq; Chu et al., "Using Propodium Monoazide Sequencing (PMA-Seq) to Develop Data-Driven Best Practices in Fecal Microbiota Transplantations." Open Forum Infect Dis. Oxford University Press; 2015)]. Briefly, this approach provides a high-throughput, culture-independent measure of cell viability.

In some embodiments, the stool or stool-derived product comprises at least about $10^6$ viable cells/g, at least about $10^7$ viable cells/g, at least about $10^8$ viable cells/g, at least about $10^9$ viable cells/g, at least about $10^{10}$ viable cells/g, at least about $10^{11}$ viable cells/g, at least about $10^{12}$ viable cells/g, at least about $10^{13}$ viable cells/g, or at least about $10^{14}$ viable cells cells/g. In some embodiments, the stool or stool-derived product comprises at least about $10^6$ CFU/mL, at least about $10^7$ CFU/mL, at least about $10^8$ CFU/mL, at least about $10^9$ CFU/mL, at least about $10^{10}$ CFU/mL, at least about $10^{11}$ CFU/mL, at least about $10^{12}$ CFU/mL, at least about $10^{13}$ CFU/mL, or at least about $10^{14}$ CFU/mL. In some embodiments, the stool or stool-derived product comprises a spore count of at least about $10^2$ CFU/mL, of at least about $10^3$ CFU/mL, of at least about $10^4$ CFU/mL, of at least about $10^5$ CFU/mL, of at least about $10^6$ CFU/mL, of at least about $10^7$ CFU/mL, or of at least about $10^8$ CFU/mL.

In embodiments, an illustrative therapeutic composition comprises starting material from a donor. In embodiments, an illustrative therapeutic composition comprises material from one or more healthy donors. In embodiments, an illustrative therapeutic composition comprises starting material from a defined donor pool. In embodiments, a donor is an adult male. In embodiments, a donor is an adult female. In embodiments, a donor is an adolescent male. In embodiments, a donor is an adolescent female. In embodiments, a donor is a female toddler. In embodiments, a donor is a male toddler. In embodiments, a donor is healthy. In embodiments, a human donor is a child whose age is below about 18, 15, 12, 10, 8, 6, 4, 3, 2, or 1 year. In embodiments, a human donor is an elderly individual. In embodiments, a human donor is an individual above about 30, 35, 40, 45, 50, 55, 60, 65, 70, 75, 80, 85, 90, or 95 years old. In embodiments, a donor is about between 1 and 5, between 2 and 10, between 3 and 18, between 21 and 50, between 21 and 40, between 21 and 30, between 50 and 90, between 60 and 90, between 70 and 90, between 60 and 80, or between 65 and 75 years old. In embodiments, a donor is a young old individual (65-74 years). In embodiments, a donor is a middle old individual (75-84 years). In embodiments, a donor is an old individual (>85 years). In embodiments, a donor is a screened, healthy, and neurotypical human.

In embodiments, a screened donor undergoes a medical history and physical exam. Donors are excluded if they have a risk of infectious agents. Additional exclusion criteria comprise one or more of the following:

1. Known viral infection with Hepatitis B, C or HIV
2. Known exposure to HIV or viral hepatitis at any time
3. High risk behaviors including sex for drugs or money, men who have sex with men, more than one sexual partner in the preceding 12 months, any past use of intravenous drugs or intranasal cocaine, history of incarceration.
4. Tattoo or body piercing within 12 months.
5. Travel to areas of the world where risk of traveler's diarrhea is higher than the US.
6. Current communicable disease, e.g., upper respiratory viral infection.
7. History of irritable bowel syndrome. Specific symptoms may include frequent abdominal cramps, excessive gas, bloating, abdominal distension, fecal urgency, diarrhea, constipation.
8. History of inflammatory bowel disease such as Crohn's disease, ulcerative colitis, microscopic colitis.
9. Chronic diarrhea.
10. Chronic constipation or use of laxatives.
11. History of gastrointestinal malignancy or known colon polyposis.
12. History of any abdominal surgery, e.g., gastric bypass, intestinal resection, appendectomy, cholecystectomy, etc.
13. Use of Probiotics or any other over the counter aids used by the potential donor for purpose of regulating digestion. Yogurt and kefir products are allowed if taken merely as food rather than nutritional supplements.
14. Antibiotics for any indication within the preceding 6 months.
15. Any prescribed immunosuppressive or anti-neoplastic medications.
16. Metabolic Syndrome, established or emerging. Criteria used for definition here are stricter than any established criteria. These include history of increased blood pressure, history of diabetes or glucose intolerance.
17. Known systemic autoimmunity, e.g., connective tissue disease, multiple sclerosis.
18. Known atopic diseases including asthma or eczema.
19. Chronic pain syndromes including fibromyalgia, chronic fatigue syndrome.
20. Ongoing (even if intermittent) use of any prescribed medications, including inhalers or topical creams and ointments.
21. Neurologic, neurodevelopmental, and neurodegenerative disorders including autism, Parkinson's disease.
22. General. Body mass index >26 kg/m2, central obesity defined by waste:hip ratio >0.85 (male) and >0.80 (female).
23. Blood pressure >135 mmHg systolic and >85 mmHg diastolic.
24. Skin—presence of a rash, tattoos or body piercing placed within a year, or jaundice
25. Enlarged lymph nodes.
26. Wheezing on auscultation.
27. Hepatomegaly or stigmata of liver disease.
28. Swollen or tender joints. Muscle weakness.
29. Abnormal neurologic examination.
30. Positive stool *Clostridium difficile* toxin B tested by PCR.
31. Positive stool cultures for any of the routine pathogens including *Salmonella, Shigella, Yersinia, Campylobacter, E. coli* O157:H7.
32. Abnormal ova and parasites examination.
33. Positive *Giardia, Cryptosporidium*, or *Helicobacter pylori* antigens.
34. Positive screening for any viral illnesses, including HIV 1 and 2, Viral Hepatitis A IgM, Hepatitis surface antigen and core Ab.
35. Abnormal RPR (screen for syphilis).
36. Any abnormal liver function tests including alkaline phosphatase, aspartate aminotransaminase, alanine aminotransferase.
37. Raised serum triglycerides >150 mg/Dl
38. HDL cholesterol <40 mg/dL (males) and <50 mg/dL (females)
39. High sensitivity CRP >2.4 mg/L
40. Raised fasting plasma glucose (>100 mg/dL)

Microbial Compositions

In aspects, a microbial composition comprises a fecal microbiota, for example in the form of or derived from fresh, frozen, dried, processed, or reconstituted feces obtained from a stool sample or stool samples of one human donor or stool samples of more than one human donor (e.g., multiple human donors).

In embodiments, substantially each bacterial strain in the fecal microbiota is in the form of or derived from fresh, frozen, dried, processed, or reconstituted feces obtained from a stool sample or stool samples of one human donor. In embodiments, each bacterial strain in the fecal microbiota is in the form of or derived from the fresh, frozen, dried, processed, or reconstituted feces. In embodiments, the microbial composition comprises a substantially complete human fecal microbiota, e.g., as contained in a stool sample or stool samples of a donor. In embodiments, the microbial composition is further supplemented, spiked, or enhanced with at least one bacterial strain obtained from a laboratory stock or isolated/purified from its source material.

In embodiments, the one human donor is the subject prior to undergoing treatment with the anti-cancer therapy. In this embodiment, a subject "banks" his/her feces before undergoing an anti-cancer therapy and is administered his/her own fecal microbiota while undergoing or after undergoing the anti-cancer therapy. Here, the goal is to return the subject's microbiome to the diversity that existed prior to the anti-cancer therapy. In embodiments, the microbial composition comprises a substantially complete human fecal microbiota as contained in a stool sample or stool samples of the subject prior to undergoing treatment with the anti-cancer therapy. In embodiments, the microbial composition is further supplemented, spiked, or enhanced with at least one bacterial strain obtained from a laboratory stock or isolated/purified from its source material.

In embodiments, substantially each bacterial strain in the fecal microbiota is in the form of or derived from fresh, frozen, dried, processed, or reconstituted feces obtained from stool samples of more than one human donor. Generally, such a microbial composition in the form of or derived from fecal microbiota from more than one human donor has increased bacterial diversity when compared to a microbial composition in the form of or derived from fecal microbiota from a stool sample or stool samples of one healthy human donor. In embodiments, each bacterial strain in the fecal microbiota is in the form of or derived from the fresh, frozen, dried, processed, or reconstituted feces obtained from a stool sample or stool samples. In embodiments, the microbial composition comprises a substantially complete human fecal microbiota as contained in stool samples from each of the more than one human donor. In embodiments, the microbial composition is further supplemented, spiked, or enhanced with at least one bacterial strain obtained from a laboratory stock or isolated/purified from its source material.

In embodiments, the fresh, frozen, dried, processed, or reconstituted feces comprises spores and/or live, vegetative cells.

In embodiments, the bacterial strains, microbial composition, fecal microbiota, stool sample(s), and/or feces is dried via lyophilization, e.g., by treating fresh or frozen feces with ethanol and chloroform.

In embodiments, the microbial composition further comprises one or more pharmaceutically-acceptable aqueous solution, binder, disintegrant, filler, and/or preservative. The one or more pharmaceutically-acceptable aqueous solution, binder, disintegrant, filler, and/or preservative may be mixed into the microbial composition to promote desirable properties, e.g., dryness vs moisture and solidity vs softness.

Illustrative aqueous solutions include water, Krebs-Henseleit bicarbonate buffer, Hank's Bicarbonate Buffer, Phosphate Buffered Saline (PBS), Tris Buffered Saline (TBS), and TBST (Tris Buffered saline and TWEEN®-20).

Illustrative binders include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Illustrative fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be added to a microbial composition to promote its disintegration when exposed to an aqueous environment. Illustrative disintegrants include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

In embodiments, the microbial composition comprises minimally processed fecal material from one human donor or more than one human donor.

In embodiments, the microbial composition comprises a fecal microbiota comprising no greater than 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material. In embodiments, the microbial composition comprises a fecal microbiota comprising no greater than 20%, 25%, 30%, 35%, 40%, 45%, 50%, 55%, 60%, 65%, 70%, 75%, 80%, 85%, 90%, or 95% weight non-living material/weight biological material.

In embodiments, the microbial composition comprises, consists of, or consists essentially of, particles of non-living material and/or particles of biological material of a fecal sample that passes through a sieve, a column, or a similar filtering device having a sieve, exclusion, or particle filter size of 2.0 mm, 1.0 mm, 0.5 mm, 0.33 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm. "Non-living material" does not include an excipient, e.g., a pharmaceutically inactive substance, such as a cryoprotectant, added to a processed fecal material. "Biological material" refers to the living material in fecal material, and includes microbes including prokaryotic cells, such as bacteria and archaea (e.g., living prokaryotic cells and spores that can sporulate to become living prokaryotic cells), eukaryotic cells such as protozoa and fungi, and viruses. In embodiments, "biological material" refers to the living material, e.g., the microbes, eukaryotic cells, and viruses, which are present in the colon of a normal healthy human. In embodiments, a fecal microbiota can be further processed, e.g., to undergo microfiltration before, after, or before and after sieving. In embodiments, a highly purified fecal microbiota product is ultra-filtrated to remove large molecules yet retaining the therapeutic microflora, e.g., bacteria.

In embodiments, the microbial composition comprises an extract of human feces where the composition is substantially odorless.

In embodiments, the microbial composition comprises fecal material or a fecal floral preparation in a lyophilized, crude, semi-purified, or purified formulation.

In embodiments, the microbial composition comprises highly refined or purified fecal flora, e.g., substantially free of non-floral fecal material.

In embodiments, the microbial composition is further supplemented, spiked, or enhanced with at least one bacterial strain obtained from a laboratory stock or isolated/purified from its source material.

In embodiments, the at least one bacterial strain obtained from a laboratory stock or isolated/purified from its source material is present in the feces and/or in the fecal microbiota of a subject who has recovered from a cancer or is in remission from a cancer. In embodiments, the at least one bacterial strain obtained from a laboratory stock or isolated/purified from its source material is present in the feces and/or in the fecal microbiota of a subject who is in remission from a cancer and previously responded to an anti-cancer therapy.

In embodiments, the at least one bacterial strain obtained from a laboratory stock or isolated/purified from its source material is known to be relevant to the treatment of a cancer or a reduction of a symptom of cancer.

In embodiments, the at least one bacterial strain obtained from a laboratory stock or isolated/purified from its source material is known to be relevant to an increase in the efficacy of an anti-cancer therapy.

In embodiments, the at least one bacterial strain obtained from a laboratory stock or isolated/purified from its source material is known to be relevant to the reduction of side effects caused by an anti-cancer therapy, e.g., an oncology-treatment induced condition (OTIC) of the anti-cancer therapy.

In embodiments, the microbial composition comprises or consists essentially of a substantially entire microbiota in which at least about 90%, 91%, 92%, 93%, 94%, 95%, 96%, 97%, 98%, 99%, 99.5%, 99.6%, 99.7%, 99.8% or 99.9% of the bacterial strains in the fecal microbiota is in the form of or derived from feces of one human donor or more than one human donor. In embodiments, the microbial composition comprises no more than about 0.1%, 0.2%, 0.3%, 0.4%, 0.5%, 0.6%, 0.7%, 0.8%, 0.9% or 1.0% bacterial strains obtained from a laboratory stock or isolated/purified from its source material.

In embodiments, the microbial composition comprises or consists essentially of a substantially entire microbiota as described in Sadowsky et al., WO 2012/122478 or as described in Borody et al., WO 2012/016287, the entire contents of which are incorporated by reference.

In embodiments, the microbial composition comprises a donor's substantially entire or non-selected fecal microbiota, reconstituted fecal material, or synthetic fecal material. In embodiments, the microbial composition comprises no antibiotic resistant population. In embodiments, the microbial composition comprises a fecal microbiota and is largely free of extraneous matter (e.g., non-living matter including acellular matter such as residual fiber, DNA, RNA, viral coat material, and non-viable material; and living matter such as eukaryotic cells from the fecal matter's donor). In embodiments, the microbial composition is substantially devoid of fiber from the stool sample.

In embodiments, a microbial composition used in a treatment disclosed herein comprises a sterile fecal filtrate or a non-cellular fecal filtrate. In embodiments, a sterile fecal filtrate originates from a donor stool. In embodiments, a sterile fecal filtrate originates from cultured microorganisms. In embodiments, a sterile fecal filtrate comprises a non-cellular, non-particulate fecal component. In embodiments, a sterile fecal filtrate is made as described in WO 2014/078911. In embodiments, a sterile fecal filtrate is made as described in Ott et al., *Gastroenterology* 152:799-911 (2017).

In embodiments, a fecal filtrate comprises secreted, excreted or otherwise liquid components or a microbiota, e.g., biologically active molecules (BAMs), which can be antibiotics or anti-inflammatory drugs, are preserved, retained, or reconstituted in a flora extract.

In embodiments, bacterial strains included in a microbial composition are contained in a fecal microbiota and/or in feces from a healthy and suitable donor, and is combined, e.g., supplemented, spiked, or enhanced, with a plurality of isolated, purified, and/or cultured bacterial strains that are known to be present in a human fecal microbiota and/or in feces of a healthy and suitable donors.

In embodiments, bacterial strains included in a microbial composition are indirectly obtained from human feces. Here, bacterial strains from human feces are cultured and the bacteria are expanded and then isolated and/or purified. The isolated/purified bacteria can be introduced into a microbial composition comprising bacterial strains directly obtained from human feces. Alternately, a plurality of isolated/purified bacteria can be combined into a microbial composition comprising only bacterial strains indirectly obtained from human feces or obtained independent of human feces.

In embodiments, the bacterial strains included in a microbial composition comprise bacteria isolated or purified from one or more humans. In embodiments, the bacterial strains in a microbial composition is isolated or purified from one or more humans. For instance, the isolation or purification may be from feces of the one or more humans. Further, the isolation or purification may be from aspirates of the fluid in the GI tract or mucosal biopsies from a site in the GI tract.

In embodiments, the bacterial strains included in a microbial composition are isolated or purified from its source material, i.e., separated from at least some of the components with which they were associated when initially produced (e.g., nature (from feces) or in an experimental setting (a laboratory stock) and/or produced, prepared, purified, and/or manufactured by man. Bacterial strains may be separated from at least about 10%, or about 20%, or about 30%, or about 40%, or about 50%, or about 60%, or about 70%, or about 80%, or about 90%, or more of the other components with which they were initially associated. In embodiments, bacterial strains are more than about 80%, or about 85%, or about 90%, or about 91%, or about 92%, or about 93%, or about 94%, or about 95%, or about 96%, or about 97%, or about 98%, or about 99%, or more than about 99% pure.

In embodiments, source material is stool from a donor or donors. The stool is centrifuged, then filtered with very high-level filtration using e.g., either metal sieving or Millipore filters, or equivalent, to ultimately permit only cells of bacterial origin to remain, e.g., often less than about 5 micrometers diameter. After the initial centrifugation, the solid material is separated from the liquid, and the solid is then filtered in progressively reducing size filters and tangential filters, e.g., using a Millipore filtration, and optionally, also comprising use of nano-membrane filtering. The filtering can also be done by sieves as described in WO 2012/122478, but in contrast using sieves that are smaller than 0.0120 mm, down to about 0.0110 mm, which ultimately result in having only bacterial cells present.

The supernatant separated during centrifugation may be filtered progressively in a filtering, e.g., a Millipore filtering or equivalent systems, to end up with liquid which is finely filtered through an about 0.22 µM filter. This removes all particulate matter including all living matter, including bacteria and viruses. The product then is sterile, but the aim is to remove the bacteria but to keep their secretions, especially antimicrobial bacteriocins, bacteria-derived cytokine-like products and all accompanying Biologically Active Molecules (BAMs), including: thuricin (which is secreted by bacilli in donor stools), bacteriocins (including colicin, troudulixine or putaindicine, or microcin or subtilosin A), lanbiotics (including nisin, subtilin, epidermin, mutacin, mersacidin, actagardine, cinnamycin), lacticins and other antimicrobial or anti-inflammatory compounds and/or additional biologically active molecules (BAMs) produced by bacteria or other microorganisms of the microbiota, and/or which are found in the "liquid component" of a microbiota.

In embodiments, a microbial composition comprises a reconstituted fecal flora consisting essentially of a combination of a purified fecal microbiota and a non-cellular fecal filtrate. In embodiments, a microbial composition comprises a purified fecal microbiota supplemented with one or more non-cellular non-particulate fecal components. In embodiments, a microbial composition comprises one or more non-cellular non-particulate fecal components. In embodiments, one or more non-cellular non-particulate fecal components comprise synthetic molecules, biologically active molecules produced by a fecal microorganism, or both. In embodiments, one or more non-cellular non-particulate fecal components comprise biologically active proteins or peptides, micronutrients, fats, sugars, small carbohydrates, trace elements, mineral salts, ash, mucous, amino acids, nutrients, vitamins, minerals, or any combination thereof. In embodiments, one or more non-cellular non-particulate fecal components comprise one or more biologically active molecules selected from bacteriocin, lanbiotic, and lacticin. In embodiments, one or more non-cellular non-particulate fecal components comprise one or more bacteriocins selected from colicin, troudulixine, putaindicine, microcin, and subtilosin A. In embodiments, one or more non-cellular non-particulate fecal components comprise one or more lanbiotics selected from thuricin, nisin, subtilin, epidermin, mutacin, mersacidin, actagardine, and cinnamycin. In embodiments, one or more non-cellular non-particulate fecal components comprise an anti-spore compound, an antimicrobial compound, an anti-inflammatory compound, or any combination thereof. In embodiments, one or more non-cellular non-particulate fecal components comprise an interleukin, a cytokine, a leukotriene, an eicosanoid, or any combination thereof.

In embodiments, to purify bacterial spores from donated stool material, the donated stool material is subjected to one or more solvent treatments. The solvent may include water and/or an alcohol, e.g., methanol, ethanol, isopropanol, butanol, propanediol, and butanediol. The alcohols can be provided already combined with water; e.g., a solution containing 10%, 20%, 25%, 30%, 35%, 40%, 45%, 50%, 55%, 60%, 65%, 70%, 75%, 89%, 85%, 90%, 95% or greater than 95%. The solvent treatments reduce the viability of non-spore forming bacterial species by 10%, 20%, 30%, 40%, 50%, 60%, 70%, 80%, 85%, 90%, 95%, 99%, 99.9%, 99.99%, 99.999%, or 99.9999%, and it may optionally reduce the viability of contaminating protists, parasites and/or viruses.

In embodiments, a healthy and suitable donor does not possess an infectious risk factors of: risk for factors for multi-drug resistance organisms (MDROs); antibiotic resistant bacteria (ARB); high risk sexual behaviors; social history including illicit drug use; and/or recent high risk travel history. In embodiments, a healthy and suitable donor does not possess a potential microbiome mediated condition of: gastrointestinal comorbidities; metabolic comorbidities; neurological comorbidities; psychiatric comorbidities; chronic pain syndromes; infectious diseases; autoimmune diseases; atopy, asthma and allergies (food and other); malignancy; relevant surgeries/other medical history; current symptoms; medications including antimicrobial therapy; and/or relevant family history. In embodiments, a sample from a healthy and suitable donor does not test positive for one or more of Adenovirus, *Campylobacter* spp., Carbapenem-resistant enterobacteriaceae (CRE), *Clostridium difficile* toxin B, *Cryptosporidium* spp., *Cyclospora*, *E. coli* 0157, Extended-spectrum beta-lactamase (ESBL), *Giardia lamblia, Helicobacter pylori,* Hepatitis A, Hepatitis B, Hepatitis C, HIV-1/2, *Isospora,* Microsporidia, Multi-Drug Resistant Organisms (MDROs), antibiotic resistant bacteria (ARB), Norovirus, Rotavirus, *Salmonella* spp., Shiga toxin, *Shigella* spp., *Staphylococcus aureus* (MRSA), *Treponema pallidum*, Vancomycin-resistant *Enterococcus* (VRE), and/or *Vibrio* spp.

In other embodiments, the bacterial strains included in a microbial composition are obtained independent of human feces (e.g., from a bacterial cell bank or from a laboratory stock).

In other embodiments, the bacterial strains included in a microbial composition are commensal bacterial strains.

In embodiments, the microbial compositions comprise live, vegetative cells, and/or spores. In embodiments, the bacterial strains are in the form of spores; the microbial composition is substantially free of live, vegetative cells. In embodiments, the bacterial strains are in the form of live, vegetative cells; the microbial composition is substantially free of spores.

In embodiments, the microbial composition comprises one or more of live, vegetative cells; spores; and lyophilized cells.

In embodiments, the bacterial strains are in the form of lyophilized cells.

In embodiments, a bacterial strain is included in the microbial composition due to its ability to engraft in a patient's GI tract. The bacterial strain is considered to successfully engraft if the strain is abundant in a fecal microbiota transplant (FMT) donor and also increased in a FMT-recipient patient compared to his/her baseline pre-FMT. In embodiments, the selected bacterial strain exhibits enhanced ability to colonize the mucosa.

In embodiments, a bacterial strain is included in the microbial composition due to its ability to colonize a patient's mucosal barrier.

In embodiments, a bacterial strain is included in the microbial composition due to its ability to preserve and/or enhance mucosal barrier integrity and function in a patient. Accordingly, in embodiments, the microbial composition includes a bacterial strain that prevents and/or reduces the loss of mucus thickness associated with various GI disorders. For example, in embodiments, a bacterial strain may be selected based on its ability to enable mucosal healing, improve mucosal barrier function, and/or to reduce inflammation.

In embodiments, the microbial composition includes a bacterial strain that results in a reduction of bacterial penetration and/or bacterial load in the mucus. Without wishing to be bound by theory, it is believed that inclusion of such bacterial strains reinforces both the structural and chemical barrier functions of the mucosa by displacing pathogenic mucus-degrading microorganisms and support mucosal repair. In embodiments, the inclusion of such bacterial strain impacts numerous inflammatory pathways linked to inappropriate microbial exposure.

In embodiments, a bacterial strain is included in the microbial composition due to its ability to decolonize pathogenic infectious agents.

In embodiments, a bacterial strain is included in the microbial composition due to its ability to eradicate a pathogenic bacterium.

In embodiments, a bacterial strain is included in the microbial composition due to its ability to compete with pathogenic infectious agents for resources (e.g., niche and/or nutrients).

In embodiments, a bacterial strain is included in the microbial composition due to its ability to directly inhibit a pathogenic bacterium through production of a secreted product.

In embodiments, the microbial composition includes a bacterial strain that decolonizes and/or eradicates sulfate-reducing bacteria (SRB) in a subject.

In embodiments, a bacterial strain is included in the microbial composition due to its ability to help maintain and/or repair a deficient gut barrier.

In embodiments, a bacterial strain is included in the microbial composition due to its ability to enhance production of one or more of butyrate, acetate, and propionate.

In embodiments, a bacterial strain is included in the microbial composition due to its ability to produce Short-Chain Fatty Acid (SCFAs) which increase the thickness of the mucus layer, maintain the health of colonocytes, inhibits nitric oxide synthase activity, reduces the concentration of host-derived nitrate levels in the gut, and induces IgA production. In embodiments, the microbial composition includes one or more bacterial strains that supplement SOFA production. As used herein, SCFAs refer to fatty acids with an aliphatic tail of less than six carbon atoms. Illustrative SCFAs include, but are not limited to, formic acid, acetic acid, propionic acid, butyric acid, isobutyric acid, valeric acid, and isovaleric acid. Without wishing to be bound by theory, SCFAs are involved in mediation of GI inflammation, and SOFA-producing bacteria are associated with sustained clinical remission, for example, in ulcerative colitis (UC) patients. Accordingly, in embodiments, a bacterial strain is included based on its ability to produce increased levels of SCFAs. Additionally, in embodiments, a bacterial strain is included for its ability to complement the capacity of a functionally deficient microbial community (e.g., the microbial community of a patient infected and/or colonized by a pathogenic bacteria) to produce levels of SCFAs comparable to healthy individuals.

In embodiments, a bacterial strain is included in the microbial composition due to its ability to induce TNF, IL-10, IL-1, a neurotransmitter (e.g., serotonin and GABA), leptin, adiponectin, and proteins involved in glycan biosynthesis or bile acid biosynthesis.

In embodiments, a bacterial strain is included in the microbial composition due to its ability to induce proliferation and/or accumulation of Foxp3+ cells, e.g., regulatory T cells (Tregs).

In embodiments, a bacterial strain is included in the microbial composition due to its ability to activate Toll-Like Receptors (TLRs), which modulate the production of antimicrobial peptides, which target many human bacterial pathogens.

In embodiments, a bacterial strain is included in the microbial composition due to its ability to induce an increase in antimicrobial peptide production.

In embodiments, a bacterial strain is included in the microbial composition due to its ability to induce expression and/or accumulation of interleukin-10 (IL-10) TNF, IL-1, a neurotransmitter (e.g., serotonin and GABA), leptin, adiponectin, and proteins involved in glycan biosynthesis or bile acid biosynthesis.

In embodiments, a bacterial strain is included in the microbial composition due to its ability to reduce proliferation and/or accumulation of cells that express interleukin-12 (IL-12), interleukin-4 (IL-4), and/or and gamma interferon (IFN-γ).

In embodiments, a bacterial strain is included in the microbial composition due to its ability to induce improved tight junction integrity.

In embodiments, a bacterial strain is included in the microbial composition based on its abundance in donors whose stool was used for successful fecal microbiota transplants (FMTs).

In embodiments, a bacterial strain is included in the microbial composition based on its presence in the stool samples of donors whose stool was used for FMTs which provided a therapeutically-effective result in a patient suffering from a gut dysbiosis disorder, e.g., caused by a previous or current anti-cancer therapy.

In embodiments, a bacterial strain is included in the microbial composition based on its ability to reduce systemic inflammatory and immunoregulatory effects in a patient.

Additional criteria that may be utilized for selecting a bacterial strain for inclusion in the microbial composition include, but are not limited to, the ability of the bacterial strain to inhibit IgA-degrading bacteria, the ability of the bacterial strain to inhibit serotonin-producing and serotonin-inducing bacteria, the ability of the bacterial strain to enhance tryptophan availability, the ability of the bacterial strain to produce anti-inflammatory zwitterionic polysaccharides, the ability of the bacterial strain modify signaling molecules interacting with the Aryl Hydrocarbon Receptor, and/or the ability of the bacterial strain to block the vitamin D receptor (VCD) or vitamin D signaling.

In embodiments, the microbial composition augments growth of at least one type of bacteria not detectably present in a patient's GI tract prior to administration.

As used herein, a bacterial strain may be "included" in a microbial composition by selectively adding a specific, isolated/purified bacterial strain to the microbial composition. Additionally, or alternatively, a bacterial strain may be "included" in a microbial composition by selecting a donor who possesses the specific bacterial strain in his/her fecal microbiota and/or in his/her feces.

In embodiments, the bacterial strains included in a microbial composition are commensal bacterial strains.

In embodiments, the bacterial strains are non-pathogenic. In embodiments, the bacterial strains are substantially free of organisms or entities which are capable of causing or affecting a disease, disorder or condition of a host organism containing the organism or entity.

In embodiments, the microbial composition includes one or more isolated or purified bacterial strains that individually or when together in a mixture have a cytotoxic or cytostatic effect on a pathogenic bacterium. In embodiments, the microbial composition exerts an inhibitory effect on a pathogenic bacterium present in or entering into the GI tract of a patient. In embodiments, the microbial composition includes one or more isolated or purified bacterial strains that interact synergistically to have a cytotoxic or cytostatic effect on a pathogenic bacterium.

In embodiments, a fecal microbiota in a therapeutic composition used herein comprises or consists essentially of a substantially isolated or a purified fecal flora or entire (or substantially entire) microbiota that is (or comprises) an isolate of fecal flora that is at least about 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.6%, 0.7%, 0.8%, 0.9% or 1.0% or more non-fecal floral material; or, a substantially isolated, purified, or substantially entire microbiota as described in Sadowsky et al., WO 2012/122478 A1, or as described in Borody et al., WO 2012/016287, the entire contents of which are incorporated by reference.

In embodiments, a therapeutic composition described herein is further supplemented, spiked, or enhanced with purified, isolated, or cultured viable non-pathogenic *Clostridium* and/or a plurality of purified, isolated, or cultured viable non-pathogenic microorganisms from one or more genera selected from the group consisting of *Collinsella, Coprococcus, Dorea, Eubacterium*, and *Ruminococcus*. In embodiments, a therapeutic composition comprises a plurality of purified, isolated, or cultured viable non-pathogenic microorganisms from one or more genera selected from the group consisting of *Clostridium, Collinsella, Coprococcus, Dorea, Eubacterium*, and *Ruminococcus*.

In embodiments, a therapeutic composition (e.g., comprising a fecal microbiota) comprises two or more genera selected from the group consisting of *Collinsella, Coprococcus, Dorea, Eubacterium*, and *Ruminococcus*. In embodiments, a therapeutic composition comprises two or more genera selected from the group consisting of *Coprococcus, Dorea, Eubacterium*, and *Ruminococcus*. In embodiments, a therapeutic composition comprises one or more, two or more, three or more, four or more, or five or more species selected from the group consisting of *Coprococcus catus, Coprococcus comes, Dorea longicatena, Eubacterium eligens, Eubacterium hadrum, Eubacterium hallii, Eubacterium rectale*, and *Ruminococcus torques*.

In embodiments, a therapeutic composition (e.g., comprising a fecal microbiota) administered herein comprises at least one, at least two, at least three, at least four, at least five, at least six, or at least seven fecal microorganisms selected from the group consisting of a *Bacteroides fragilis* ssp. *vulgatus, Collinsella aerofaciens, Bacteroides fragilis* ssp. *thetaiotaomicron, Peptostreptococcus productus* II, *Parabacteroides distasonis, Fusobacterium prausnitzii, Coprococcus eutactus, Collinsella aerofaciens* III, *Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ssp. A, *Eubacterium biforme, Bifidobacterium infantis, Eubacterium rectale Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus femientans, Eubacterium ventriosum, Bacteroides fragilis* ssp. *fragilis, Bacteroides* AR, *Coprococcus catus, Aerostipes hadrus, Eubacterium cylindroides, Eubacterium ruminantium, Eubacterium* CH-1, *Staphylococcus epidermidis, Peptostreptococcus* BL, *Eubacterium limosum, Tissirella praeacuta, Bacteroides* L, *Fusobacterium mortiferum* I, *Fusobacterium navifomie, Clostridium innocuum, Clostridium ramosum, Propionibacterium acnes, Ruminococcus* flavefaciens, *Ruminococcus* AT, *Peptococcus* AU-1, *Bacteroides fragilis* ssp. *ovatus, -ssp. d, -ssp. f; Bacteroides* L-1, L-5; *Fusobacterium nucleatum, Fusobacterium mortiferum, Escherichia coli, Gemella morbillorum, Finegoldia magnus, Peptococcus* G, -AU-2; *Streptococcus intermedius, Ruminococcus lactaris, Ruminococcus* CO *Gemmiger* X, *Coprococcus* BH, -CC; *Eubacterium tenue, Eubacterium ramulus, Bacteroides clostridfiformis* ssp. *clostridliformis, Bacteroides coagulans, Prevotella oralis, Prevotella ruminicola, Odoribacter splanchnicus, Desuifomonas pigra, Lactobacillus* G, *Succinivibrio* A, and a combination thereof.

In embodiments, a therapeutic composition (e.g., comprising a fecal microbiota) comprises non-pathogenic spores of one or more, two or more, three or more, or four or more *Clostridium* species selected from the group consisting of *Clostridium absonum, Clostridium argentinense, Clostridium baratii, Clostridium botulinum, Clostridium cadaveris, Clostridium camis, Clostridium celatum, Clostridium chauvoei, Clostridium clostridioforme, Clostridium cochlearium, Clostridium fallax, Clostridium felsineum, Clostridium ghonii, Clostridium glycolicum, Clostridium haemolyticum, Clostridium hastifomie, Clostridium histolyticum, Clostridium indolis, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tertium, Clostridium tetani, Clostridium welchii*, and *Clostridium villosum*.

In embodiments, a therapeutic composition comprises fecal bacteria from at least 1, 2, 3, 4, 5, 6, 7, 8, 9, or 10 different families. In embodiments, a therapeutic composition comprises fecal bacteria from at least 11, 12, 13, 14, 15, 16, 17, 18, 19, or 20 different families. In embodiments, a therapeutic composition comprises fecal bacteria from at least 21, 22, 23, 24, 25, 26, 27, 28, 29, or 30 different families. In embodiments, a therapeutic composition comprises fecal bacteria from at least 31, 32, 33, 34, 35, 36, 37, 38, 39, or 40 different families. In embodiments, a therapeutic composition comprises fecal bacteria from at least 41, 42, 43, 44, 45, 46, 47, 48, 49, or 50 different families. In embodiments, a therapeutic composition comprises fecal bacteria from between 1 and 10, between 10 and 20, between 20 and 30, between 30 and 40, between 40 and 50 different families. In embodiments, a therapeutic composition provided or administered herein comprises a fecal microbiota comprising no greater than 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material. In embodiments, a therapeutic composition provided or administered herein comprises a fecal microbiota comprising no greater than 20%, 25%, 30%, 35%, 40%, 45%, 50%, 55%, 60%, 65%, 70%, 75%, 80%, 85%, 90%, or 95% A weight non-living material/weight biological material. In embodiments, a therapeutic composition provided or administered herein comprises, consists of, or consists essentially of, particles of non-living material and/or particles of biological material of a fecal sample that passes through a sieve, a column, or a similar filtering device having a sieve, exclusion, or particle filter size of 2.0 mm, 1.0 mm, 0.5 mm, 0.33 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.002 mm. "Non-living material" does not include an excipient, e.g., a pharmaceutically inactive substance, such as a cryoprotectant, added to a processed fecal material. "Biological material" refers to the living material in fecal material, and includes microbes including prokaryotic cells, such as bacteria and archaea (e.g., living prokaryotic cells and spores that can sporulate to become living prokaryotic cells), eukaryotic cells such as protozoa and fungi, and viruses. In one embodiment, "biological material" refers to the living material, e.g., the microbes, eukaryotic cells, and viruses, which are present in the colon of a normal healthy human. In embodiments, a therapeutic composition provided or administered herein comprises an extract of human feces where the composition is substantially odorless. In embodiments, a therapeutic composition provided or administered herein comprises fecal material or a fecal floral preparation in a lyophilized, crude, semi-purified or purified formulation.

In embodiments, a fecal microbiota in a therapeutic composition comprises highly refined or purified fecal flora, e.g., substantially free of non-floral fecal material. In embodiments, a fecal microbiota can be further processed, e.g., to undergo microfiltration before, after, or before and after sieving. In embodiments, a highly purified fecal microbiota product is ultra-filtrated to remove large molecules but retain the therapeutic microflora, e.g., bacteria.

In embodiments, a therapeutic composition administered herein comprises no viable *Bacteroides, Fusobacterium, Propionibacterium, Lactobacillus, Ruminococcus, Escherichia coli, Gemmiger, Desulfomonas, Peptostreptococcus, Bifidobacterium, Monilia*, or any combination thereof. In embodiments, a therapeutic composition administered herein comprises no viable *Bacteroides fragilis* ssp. *vulgatus, Collinsella aerofaciens, Bacteroides fragilis* ssp. *thetaiotaomicron, Peptostreptococcus productus* II, *Parabacteroides distasonis, Fusobacterium prausnitzii, Coprococcus eutactus, Collinsella aerofaciens* III, *Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ssp. A, *Eubacterium biforme, Bifidobacterium infantis, Eubacterium rectale, Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ssp. *fragilis, Bacteroides* AR, *Coprococcus catus, Aerostipes hadrus, Eubacterium cylindroides, Eubacterium ruminantium, Eubacterium* CH-1, *Staphylococcus epidermidis, Peptostreptococcus* BL, *Eubacterium limosum, Tissirella praeacuta, Bacteroides* L, *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Bacteroides fragilis* ssp. *ovatus*, -ssp. d, -ssp. f; *Bacteroides* L-1, L-5; *Fusobacterium nucleatum, Fusobacterium mortiferum, Escherichia coli, Gemella morbillorum, Finegoldia magnus, Peptococcus* G, -AU-2; *Streptococcus intermedius, Ruminococcus lactaris, Ruminococcus* CO *Gemmiger* X, *Coprococcus* BH, -CC; *Eubacterium tenue, Eubacterium ramulus, Bacteroides clostridiiformis* ssp. *clostridliformis, Bacteroides coagulans, Prevotella oralis, Prevotella ruminicola, Odoribacter splanchnicus, Desuifomonas pigra, Lactobacillus* G, *Succinivibrio* A, or a combination thereof.

In embodiments, a fecal microbiota in a therapeutic composition used herein is derived from disease-screened fresh homologous feces or equivalent freeze-dried and reconstituted feces. In embodiments, fresh, homologous feces does not include an antibiotic resistant population. In embodiments, a fecal microbiota in a therapeutic composition is derived from a synthetic fecal composition. In embodiments, a synthetic fecal composition comprises a preparation of viable flora which preferably in proportional content, resembles normal healthy human fecal flora which does not include antibiotic resistant populations. Suitable microorganisms may be selected from the following: *Bacteroides, Eubacterium, Fusobacterium, Propionibacterium, Lactobacillus, Ruminococcus, Escherichia coli, Gemmiger, Clostridium, Desulfomonas, Peptostreptococcus, Bifidobacterium, Collinsella, Coprococcus, Dorea*, and *Ruminococcus*.

In embodiments, a therapeutic composition administered herein comprises a fecal microbiota. In embodiments, the preparation of a fecal microbiota used herein involves a treatment selected from the group consisting of ethanol treatment, detergent treatment, heat treatment, irradiation, and sonication. In embodiments, the preparation of a fecal microbiota used herein involves no treatment selected from the group consisting of ethanol treatment, detergent treatment, heat treatment, irradiation, and sonication. In embodiments, the preparation of a fecal microbiota used herein involves a separation step selected from the group consisting of density gradients, filtration (e.g., sieves, nylon mesh), and chromatography. In embodiments, the preparation of a fecal microbiota used herein involves no separation step selected from the group consisting of density gradients, filtration (e.g., sieves, nylon mesh), and chromatography. In embodiments, a fecal microbiota used herein comprises a donor's entire fecal microbiota. In embodiments, a therapeutic composition administered herein comprises a fecal microbiota substantially free of eukaryotic cells from the fecal microbiota's donor.

In embodiments, a treatment method provided here comprises the use of both fecal bacterial cells, e.g., a partial or a complete representation of the human GI microbiota, and an isolated, processed, filtered, concentrated, reconstituted and/or artificial liquid component (e.g., fecal filtrate) of the flora (the microbiota) which comprises, among others ingredients, bacterial secretory products such as e.g., bacteriocins (proteinaceous toxins produced by bacteria, including colicin, troudulixine or putaindicine, or microcin or subtilosin A), lanbiotics (a class of peptide antibiotics that contain a characteristic polycyclic thioether amino acid lanthionine or methyllanthionine, and unsaturated amino acids dehydroalanine and 2-aminoisobutyric acid; which include thuricin (which is secreted by bacilli in donor stools), nisin, subtilin, epidermin, mutacin, mersacidin, actagardine, cinnamycin), a lacticin (a family of pore-forming peptidic toxins) and other antimicrobial or anti-inflammatory compounds and/or additional biologically active molecules (BAMs) produced by bacteria or other microorganisms of the microbiota, and/or which are found in the "liquid component" of a microbiota.

In embodiments, a fecal bacteria-based therapeutic composition is used concurrently with a fecal non-cellular filtrate-based therapeutic composition. In embodiments, a patient is treated with a first fecal non-cellular filtrate-based therapeutic composition before being given a second fecal bacteria-based therapeutic composition, or vice versa. In embodiments, a treatment method comprises three steps: first, antibiotic pretreatment to non-selectively remove infectious pathogen(s); second, a fecal non-cellular filtrate-based treatment step to further suppress selected infectious pathogen(s); and third, giving the patient a fecal bacteria-based therapeutic composition to re-establish a functional intestinal microbiome.

In embodiments, a therapeutic composition administered herein comprises fecal bacteria. In embodiments, a therapeutic composition administered herein comprises one or more, two or more, three or more, four or more, or five or more isolated, purified, or cultured microorganisms selected from the group consisting of *Clostridium, Bacillus, Collinsella, Bacteroides, Eubacterium, Fusobacterium, Propionibacterium, Lactobacillus, Ruminococcus, Escherichia coli,*

*Gemmiger, Desulfomonas, Peptostreptococcus, Bifidobacterium, Coprococcus, Dorea*, and *Monilia*.

In embodiments, a therapeutic composition administered herein comprises a fecal microbiota further supplemented, spiked, or enhanced with a fecal microorganism. In embodiments, a fecal microbiota is supplemented with a non-pathogenic (or with attenuated pathogenicity) bacterium of *Clostridium, Collinsella, Dorea, Ruminococcus, Coprococcus, Prevotella, Veillonella, Bacteroides, Baccillus*, or a combination thereof. In embodiments, a therapeutic composition administered herein comprises a fecal microbiota further supplemented, spiked, or enhanced with a species of Veillonellaceae, Firmicutes, Gammaproteobacteria, Bacteroidetes, or a combination thereof. In embodiments, a therapeutic composition administered herein comprises a fecal microbiota further supplemented with fecal bacterial spores. In embodiments, fecal bacterial spores are *Clostridium* spores, *Bacillus* spores, or both.

Illustrative pathogenic bacteria include *C. difficile, Salmonella* spp., enteropathogenic *E. coli*, multi-drug resistant bacteria such as *Klebsiella*, and *E. coli*, Carbapenem-resistant Enterobacteriaceae (CRE), extended spectrum beta-lactam resistant Enterococci (ESBL), and vancomycin-resistant Enterococci (VRE). Further illustrative bacteria include *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, extended spectrum beta-lactam resistant Enterococci (ESBL), Carbapenem-resistant Enterobacteriaceae (CRE), and vancomycin-resistant Enterococci (VRE). Illustrative pathogenic bacteria include *Aeromonas hydrophila, Campylobacter fetus, Plesiomonas shigelloides, Bacillus cereus, Campylobacter jejuni, Clostridium botulinum, Clostridium difficile, Clostridium perfringens*, enteroaggregative *Escherichia coli*, enterohemorrhagic *Escherichia coli*, enteroinvasive *Escherichia coli*, enterotoxigenic *Escherichia coli* (such as, but not limited to, LT and/or ST), *Escherichia coli* O157:H7, *Helicobacter pylori, Klebsiellia pneumonia, Lysteria monocytogenes, Plesiomonas shigelloides, Salmonella* spp., *Salmonella typhi, Salmonella paratyphi, Shigella* spp., *Staphylococcus* spp., *Staphylococcus aureus*, vancomycin-resistant *enterococcus* spp., *Vibrio* spp., *Vibrio cholerae, Vibrio parahaemolyticus, Vibrio vulnificus*, and *Yersinia enterocolitica*. Specifically-relevant pathogenic bacteria include Antibiotic-resistant Proteobacteria, Vancomycin Resistant *Enterococcus* (VRE), Carbapenem Resistant Enterobacteriaceae (CRE), and Extended Spectrum Beta-Lactamase producing Enterobacteriaceae (ESBL-E).

In embodiments, a microbial composition described herein comprises a fecal microbiota comprising a Shannon Diversity Index of greater than or equal to 0.3, greater than or equal to 0.4, greater than or equal to 0.5, greater than or equal to 0.6, greater than or equal to 0.7, greater than or equal to 0.8, greater than or equal to 0.9, greater than or equal to 1.0, greater than or equal to 1.1, greater than or equal to 1.2, greater than or equal to 1.3, greater than or equal to 1.4, greater than or equal to 1.5, greater than or equal to 1.6, greater than or equal to 1.7, greater than or equal to 1.8, greater than or equal to 1.9, greater than or equal to 2.0, greater than or equal to 2.1, greater than or equal to 2.2, greater than or equal to 2.3, greater than or equal to 2.4, greater than or equal to 2.5, greater than or equal to 3.0, greater than or equal to 3.1, greater than or equal to 3.2, greater than or equal to 3.3, greater than or equal to 3.4, greater than or equal to 3.5, greater than or equal to 3.6, greater than or equal to 3.7, greater than or equal to 3.8, greater than or equal to 3.9, greater than or equal to 4.0, greater than or equal to 4.1, greater than or equal to 4.2, greater than or equal to 4.3, greater than or equal to 4.4, greater than or equal to 4.5, or greater than or equal to 5.0. In embodiments, a microbial composition comprises fecal microbiota comprising a Shannon Diversity Index of between 0.1 and 3.0, between 0.1 and 2.5, between 0.1 and 2.4, between 0.1 and 2.3, between 0.1 and 2.2, between 0.1 and 2.1, between 0.1 and 2.0, between 0.4 and 2.5, between 0.4 and 3.0, between 0.5 and 5.0, between 0.7 and 5.0, between 0.9 and 5.0, between 1.1 and 5.0, between 1.3 and 5.0, between 1.5 and 5.0, between 1.7 and 5.0, between 1.9 and 5.0, between 2.1 and 5.0, between 2.3 and 5.0, between 2.5 and 5.0, between 2.7 and 5.0, between 2.9 and 5.0, between 3.1 and 5.0, between 3.3 and 5.0, between 3.5 and 5.0, between 3.7 and 5.0, between 31.9 and 5.0, or between 4.1 and 5.0. In embodiments, a Shannon Diversity Index is calculated at the phylum level. In embodiments, a Shannon Diversity Index is calculated at the family level. In embodiments, a Shannon Diversity Index is calculated at the genus level. In embodiments, a Shannon Diversity Index is calculated at the species level. In embodiments, a microbial composition comprises a preparation of flora in proportional content that resembles a normal healthy human fecal flora.

As used herein, "Shannon Diversity Index" refers to a diversity index that accounts for abundance and evenness of species present in a given community using the formula:

$$H = -\sum_{i=1}^{R} p_i \ln p_i$$

where H is Shannon Diversity Index, R is the total number of species in the community, and pi is the proportion of R made up of the ith species. Higher values indicate diverse and equally distributed communities, and a value of 0 indicates only one species is present in a given community. For further reference, see Shannon and Weaver, (1949) *The mathematical theory of communication*. The University of Illinois Press, Urbana. 117 pp.

Therapeutic Compositions, Administration, and Dosage

Disclosed herein are methods for increasing efficacy of an anti-cancer therapy. For example, the method comprises administering to a subject a therapeutic composition comprising a microbial composition. The microbial composition comprises a human fecal microbiota obtained from a stool sample or stool samples of one human donor or stool samples of more than one human donor (e.g., multiple human donors). In embodiments, the fecal microbiota may be in the form of or derived from fresh, frozen, dried, processed, or reconstituted feces. The subject may have undergone, is undergoing, or will undergo treatment with the anti-cancer therapy.

Disclosed herein are methods for treating, preventing, reducing or inhibiting an OTIC induced by an anti-cancer therapy. For example, the method comprises administering to a subject a therapeutic composition comprising a microbial composition where the subject has undergone, is undergoing, or will undergo treatment with the anti-cancer therapy. The microbial composition comprises a human fecal microbiota obtained from a stool sample or stool samples of one human donor or stool samples of more than one human donor (e.g., multiple human donors). In embodiments, the fecal microbiota may be in the form of or derived from fresh, frozen, dried, processed, or reconstituted feces.

Another aspect is a method of treating cancer. For example, the method comprises orally administering to a subject a therapeutic composition comprising a microbial composition which comprises a fecal microbiota, e.g., in the form of or derived from fresh, frozen, dried, processed, or reconstituted from feces obtained from a stool sample or stool samples of one human donor or stool samples of more than one human donor. When formulated for oral administration, the therapeutic composition may be encapsulated in a capsule that is coated with an enteric coating such that the microbial composition is released from the capsule in the subject's intestine, e.g., colon.

Further disclosed herein are therapeutic compositions for treating, preventing, or reducing an OTIC induced by an anti-cancer therapy. The therapeutic composition comprises a microbial composition comprising a fecal microbiota, e.g., in the form of or derived from fresh, frozen, dried, processed, or reconstituted from feces obtained from a stool sample or stool samples of one human donor or stool samples of more than one human donor. When formulated for oral administration, the therapeutic composition may be encapsulated in a capsule that is coated with an enteric coating such that the microbial composition is released from the capsule in the subject's intestine, e.g., colon.

It will be appreciated that the actual dose of the therapeutic composition to be administered according to the present disclosure will vary according to, for example, the particular dosage form. Many factors that may modify the action of the therapeutic composition (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

In embodiments, the therapeutic composition is formulated for enteral (e.g., oral and aboral) administration.

In embodiments, the enteral administration is an oral administration or an aboral administration.

In embodiments, the enteral administration is an oral administration, which is via a capsule encapsulating the therapeutic composition or via an endoscopic delivery system (e.g., via nasogastric tube). In embodiments, the oral administration is via a capsule encapsulating the therapeutic composition and via an endoscopic delivery system. When administered via an endoscopic delivery system, the therapeutic composition will be in a non-solid format, e.g., semi-solid, suspension, and liquid form.

In embodiments, the enteral administration is an aboral administration, which is via suppository or via a colonoscopic delivery system (e.g., via a sigmoidoscopic device). When administered via a colonoscopic delivery system, the therapeutic composition will be in a non-solid format, e.g., semi-solid, suspension, and liquid form.

In embodiments, the enteral administration is an oral administration and an aboral administration. In embodiments, the oral administration is via an endoscopic delivery system and the aboral administration is via a colonoscopic delivery system. In embodiments, the oral administration is via a capsule encapsulating the therapeutic composition and the aboral administration is via a colonoscopic delivery system. In embodiments, the oral administration is via a capsule encapsulating the therapeutic composition and via an endoscopic delivery system and the aboral administration is via a colonoscopic delivery system.

In embodiments, a subject is orally administered an initial therapeutic composition comprising the microbial composition and orally administered a subsequent therapeutic composition comprising the microbial composition. In embodiments, the dose of the subsequent therapeutic composition is greater than, equal to, or less than the dose of the initial therapeutic composition.

In embodiments, a therapeutic composition formulated for enteral (e.g., oral and aboral) administration comprises a microbial composition and an additional therapeutic agent, e.g., anti-cancer therapeutic agent.

In embodiments, a therapeutic composition comprising a microbial composition is formulated for enteral (e.g., oral and aboral) administration and an anti-cancer therapeutic agent is administered for parenteral administration. Examples of parenteral administration include intramuscular, subdermal, subcutaneous, intravenous, and intradermal injection.

In embodiments, the dose of the microbial composition is effective to increase efficacy of an anti-cancer therapy.

In embodiments, the dose of the microbial composition is effective to prevent or reduce an OTIC induced by an anti-cancer therapy.

In embodiments, a pharmaceutically active or therapeutic effective dose of a microbial composition comprises at least about $10^4$, $10^5$, $10^6$, $10^7$, $10^8$, $10^9$, $10^{10}$, $10^{11}$, $10^{12}$, $10^{13}$, $10^{14}$, or $10^{15}$ colony forming units (CFUs) or bacteria (e.g., germinable bacterial spores). In embodiments, a pharmaceutically active therapeutic effective dose of a therapeutic composition comprises at most about $10^4$, $10^5$, $10^6$, $10^7$, $10^8$, $10^9$, $10^{10}$, $10^{11}$, $10^{12}$, $10^{13}$, $10^{14}$, or $10^{15}$ cfu. In embodiments, a pharmacologically active therapeutic effective dose of a therapeutic composition is selected from $10^8$ cfu to $10^{14}$ cfu, from $10^9$ cfu to $10^{13}$ cfu, from $10^{10}$ cfu to $10^{12}$ cfu, from $10^9$ cfu to $10^{14}$ cfu, from $10^9$ cfu to $10^{12}$ cfu, from $10^9$ cfu to $10^{11}$ cfu, from $10^9$ cfu to $10^{10}$ cfu, from $10^{10}$ cfu to $10^{14}$ cfu, from $10^{10}$ cfu to $10^{13}$ cfu, from $10^{11}$ cfu to $10^{14}$ cfu, from $10^{11}$ cfu to $10^{13}$ cfu, from $10^{12}$ cfu to $10^{14}$ cfu, and from $10^{13}$ cfu to $10^{14}$ cfu. In embodiments, a therapeutic composition comprises the foregoing pharmaceutically active or therapeutic effective dose in a unit weight of about 0.2, 0.4, 0.6, 0.8 or 1.0 gram, or a unit volume of about 0.2, 0.4, 0.6, 0.8 or 1.0 milliliter.

In embodiments, a pharmaceutically active or therapeutic effective dose of a therapeutic composition comprises at least about $10^5$, $10^6$, $10^7$, $10^8$, $10^9$, $10^{10}$, $10^{11}$, $10^{12}$, $10^{13}$, $10^{14}$, or $10^{15}$ cells or spores. In embodiments, a pharmaceutically active or therapeutic effective dose of a therapeutic composition comprises at most about $10^5$, $10^6$, $10^7$, $10^8$, $10^9$, $10^{10}$, $10^{11}$, $10^{12}$, $10^{13}$, $10^{14}$, or $10^{15}$ total cells or spores. In embodiments, a pharmacologically active or therapeutic effective dose of a therapeutic composition is selected from $10^8$ to $10^{14}$, from $10^9$ to $10^{13}$, from $10^{10}$ to $10^{12}$, from $10^9$ to $10^{14}$, from $10^9$ to $10^{12}$, from $10^9$ to $10^{11}$, from $10^9$ to $10^{10}$, from $10^{10}$ to $10^{14}$, from $10^{10}$ to $10^{13}$, from $10^{11}$ to $10^{14}$, from $10^{11}$ to $10^{13}$, from $10^{12}$ to $10^{14}$, and from $10^{13}$ to $10^{14}$ cells or spores. In embodiments, the cell count is directed to live cells. In embodiments, a therapeutic composition comprises the foregoing pharmaceutically active or therapeutic effective dose of a therapeutic composition in a unit weight of about 0.2, 0.4, 0.6, 0.8 or 1.0 gram, or a unit volume of about 0.2, 0.4, 0.6, 0.8 or 1.0 milliliter. In embodiments, a pharmaceutically active or therapeutic effective dose of a therapeutic composition comprises between $10^{10}$ and $10^{12}$ cells. In embodiments, a pharmaceutically active or therapeutic effective dose of a therapeutic composition comprises between $10^{10}$ and $10^{12}$ cells per capsule. In embodiments, a pharmaceutically active or therapeutic effective dose of a therapeutic composition comprises between $10^9$ and $10^{12}$ cells. In embodiments, a pharmaceutically active or therapeutic effective dose of a therapeutic composition comprises between $10^9$ and $10^{12}$ cells per capsule.

In embodiments, every about 200 mg of a therapeutic composition comprises a pharmacologically active dose. In embodiments, every about 75, 100, 125, 150, 175, 200, 250, 300, 350, 400, 450, 500, 750, 1000, 1500, or 2000 mg of a therapeutic composition comprises a pharmacologically active dose.

Individual doses of the therapeutic composition can be administered in unit dosage forms (e.g., capsules) containing, for example, from about 0.01 mg of a microbial composition to about 5,000 mg, from about 0.01 mg to about 4,000 mg, from about 0.01 mg to about 3,000 mg, from about 0.01 mg to about 2,000 mg, from about 0.01 mg to about 1,000 mg, from about 0.01 mg to about 950 mg, from about 0.01 mg to about 900 mg, from about 0.01 mg to about 850 mg, from about 0.01 mg to about 800 mg, from about 0.01 mg to about 750 mg, from about 0.01 mg to about 700 mg, from about 0.01 mg to about 650 mg, from about 0.01 mg to about 600 mg, from about 0.01 mg to about 550 mg, from about 0.01 mg to about 500 mg, from about 0.01 mg to about 450 mg, from about 0.01 mg to about 400 mg, from about 0.01 mg to about 350 mg, from about 0.01 mg to about 300 mg, from about 0.01 mg to about 250 mg, from about 0.01 mg to about 200 mg, from about 0.01 mg to about 150 mg, from about 0.01 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg of the active ingredient per unit dosage form, or from about 5 mg to about 80 mg per unit dosage form. For example, a unit dosage form can include about 0.01 mg of a microbial composition, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 2,000 mg, about 3,000 mg, about 4,000 mg, or about 5,000 mg of the active ingredient, inclusive of all values and ranges therebetween.

In embodiments, the therapeutic composition is administered at an amount of from about 0.01 mg of a microbial composition to about 100 mg daily, an amount of from about 0.01 mg to about 5,000 mg daily, about 0.01 mg to about 4,000 mg daily, about 0.01 mg to about 3,000 mg daily, about 0.01 mg to about 2,000 mg daily, about 0.01 mg to about 1,000 mg daily, from about 0.01 mg to about 950 mg daily, from about 0.01 mg to about 900 mg daily, from about 0.01 mg to about 850 mg daily, from about 0.01 mg to about 800 mg daily, from about 0.01 mg to about 750 mg daily, from about 0.01 mg to about 700 mg daily, from about 0.01 mg to about 650 mg daily, from about 0.01 mg to about 600 mg daily, from about 0.01 mg to about 550 mg daily, from about 0.01 mg to about 500 mg daily, from about 0.01 mg to about 450 mg daily, from about 0.01 mg to about 400 mg daily, from about 0.01 mg to about 350 mg daily, from about 0.01 mg to about 300 mg daily, from about 0.01 mg to about 250 mg daily, from about 0.01 mg to about 200 mg daily, from about 0.01 mg to about 150 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In embodiments, the therapeutic composition is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 2,000 mg, about 3,000 mg, about 4,000 mg, or about 5,000 mg inclusive of all values and ranges therebetween.

In embodiments, a suitable dosage of the therapeutic composition is in a range of about 0.01 mg/kg of a microbial composition to about 100 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 20 mg/kg body weight, about 30 mg/kg body weight, about 40 mg/kg body weight, about 50 mg/kg body weight, about 60 mg/kg body weight, about 70 mg/kg body weight, about 80 mg/kg body weight, about 90 mg/kg body weight, or about 100 mg/kg body weight, inclusive of all values and ranges therebetween.

In embodiments, a suitable dosage of the therapeutic composition in a range of about 0.01 mg/kg of a microbial composition to about 100 mg/kg of body weight, in a range of about 0.01 mg/kg to about 90 mg/kg of body weight, in a range of about 0.01 mg/kg to about 80 mg/kg of body weight, in a range of about 0.01 mg/kg to about 70 mg/kg of body weight, in a range of about 0.01 mg/kg to about 60 mg/kg of body weight, in a range of about 0.01 mg/kg to about 50 mg/kg of body weight, in a range of about 0.01 mg/kg to about 40 mg/kg of body weight, in a range of about 0.01 mg/kg to about 30 mg/kg of body weight, in a range of about 0.01 mg/kg to about 20 mg/kg of body weight, in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In embodiments, the present disclosure provides a method for increasing efficacy of an anti-cancer therapy, or treating, preventing, or reducing an OTIC induced by an anti-cancer therapy, in a subject in need thereof, where the method comprises administering to the subject a therapeutically effective amount/dose of a therapeutic composition comprising live non-pathogenic bacteria. In embodiments, the present disclosure provides a method for increasing efficacy of an anti-cancer therapy, or treating, preventing, or reducing an OTIC induced by an anti-cancer therapy, in a subject in need thereof, where the method comprises administering daily to the subject a therapeutically effective amount/dose of a therapeutic composition comprising live non-pathogenic fecal bacteria. In embodiments, a therapeutic composition is administered to a patient in need of increased efficacy of an anti-cancer therapy, or prevention or reduction of an OTIC induced by an anti-cancer therapy, at least once daily or weekly for at least two consecutive days or weeks. In embodiments, a therapeutic composition is administered at least once daily or weekly for at least 3, 4, 5, 6, 7, 8, 9, 10, 11, 12, 13, 14, or 15 consecutive days or weeks. In embodiments, a therapeutic composition is administered at least once daily or weekly for at least 1, 2, 3, 4, 5, 6, 7, 8, 9, 10, 11, or 12 consecutive days or weeks. In embodiments, a therapeutic composition is administered at least once daily or weekly for at most 4, 5, 6, 7, 8, 9, 10, 11, 12, 13, 14, 15, 16, 17, 18, 19, or 20 consecutive days or weeks. In embodiments, a therapeutic composition is administered at least once daily or weekly for at most 1, 2, 3, 4, 5, 6, 7, 8, 9, 10, 11, or 12 consecutive weeks or months. In embodiments, a therapeutic composition is administered at least once for at least 1, 2, 3, 4, 5, 6, 7, 8, 9, 10, 11, or 12 consecutive months or years, chronically for a subject's entire life span, or an indefinite period of time.

In embodiments, a therapeutic composition is administered to a patient in need of increased efficacy of an anti-cancer therapy, or prevention or reduction of an OTIC induced by an anti-cancer therapy, at least twice daily or weekly for at least two consecutive days or weeks. In embodiments, a therapeutic composition is administered at least twice daily or weekly for at least 3, 4, 5, 6, 7, 8, 9, 10, 11, 12, 13, 14, or 15 consecutive days or weeks. In embodiments, a therapeutic composition is administered at least twice daily or weekly for at least 1, 2, 3, 4, 5, 6, 7, 8, 9, 10, 11, or 12 consecutive days or weeks. In embodiments, a therapeutic composition is administered at least twice daily or weekly for at most 4, 5, 6, 7, 8, 9, 10, 11, 12, 13, 14, 15, 16, 17, 18, 19, or 20 consecutive days or week. In embodiments, a therapeutic composition is administered at least twice daily or weekly for at most 1, 2, 3, 4, 5, 6, 7, 8, 9, 10, 11, or 12 consecutive weeks or months. In embodiments, a therapeutic composition is administered at least twice for at least 1, 2, 3, 4, 5, 6, 7, 8, 9, 10, 11, or 12 consecutive months or years, chronically for a subject's entire life span, or an indefinite period of time.

In embodiments, a therapeutic composition is administered to a patient in need of increased efficacy of an anti-cancer therapy, or prevention or reduction of an OTIC induced by an anti-cancer therapy, at least three times daily or weekly for at least two consecutive days or weeks. In embodiments, a therapeutic composition is administered at least three times daily or weekly for at least 3, 4, 5, 6, 7, 8, 9, 10, 11, 12, 13, 14, or 15 consecutive days or weeks. In embodiments, a therapeutic composition is administered at least three times daily or weekly for at least 1, 2, 3, 4, 5, 6, 7, 8, 9, 10, 11, or 12 consecutive days or weeks. In embodiments, a therapeutic composition is administered at least three times daily for at most 4, 5, 6, 7, 8, 9, 10, 11, 12, 13, 14, 15, 16, 17, 18, 19, or 20 consecutive days or weeks. In embodiments, a therapeutic composition is administered at least three times daily for at most 1, 2, 3, 4, 5, 6, 7, 8, 9, 10, 11, or 12 consecutive weeks or months. In embodiments, a therapeutic composition is administered at least three times for at least 1, 2, 3, 4, 5, 6, 7, 8, 9, 10, 11, or 12 consecutive months or years, chronically for a subject's entire life span, or an indefinite period of time.

In embodiments, the present disclosure provides a method for increasing efficacy of an anti-cancer therapy, or treating, preventing, or reducing an OTIC induced by an anti-cancer therapy, in a subject in need thereof, where the method comprises administering orally to the subject a therapeutically effective amount/dose of a therapeutic composition comprising live, non-pathogenic, synthetic bacterial mixture or live, non-pathogenic, purified or extracted, fecal microbiota, where the dose is administered at a dosing schedule of at least once or twice daily or weekly for at least three consecutive days or weeks. In embodiments, a dose is administered at least once, twice, or three times daily or weekly for a period between 1 and 12 weeks, between 2 and 12 weeks, between 3 and 12 weeks, between 4 and 12 weeks, between 5 and 12 weeks, between 6 and 12 weeks, between 7 and 12 weeks, between 8 and 12 weeks, between 9 and 12 weeks, between 10 and 12 weeks, between 1 and 2 weeks, between 2 and 3 weeks, between 3 and 4 weeks, between 4 and 5 weeks, between 5 and 6 weeks, between 6 and 7 weeks, between 7 and 8 weeks, between 8 and 9 weeks, between 9 and 10 weeks, or between 10 and 11 weeks.

In embodiments, the present disclosure provides a method for increasing efficacy of an anti-cancer therapy, or treating, preventing, or reducing an OTIC induced by an anti-cancer therapy, in a subject in need thereof, where the method comprises a first dosing schedule followed by a second dosing schedule. In embodiments, a first dosing schedule comprises a treatment or induction dose. In embodiments, a first dosing schedule comprises a continuous dosing schedule. In embodiments, a second dosing schedule comprises a maintenance dose lower than or equal to a therapeutically effective amount/dose of a first dosing schedule. In embodiments, a second dosing schedule lasts for at least about 2, 4, 6, 8, 10, 12, 18, 24, 36, 48, 72, or 96 months. In embodiments, a second dosing schedule lasts permanently, for a treated subject's entire life span, or an indefinite period of time. In embodiments, a second dosing schedule is a continuous dosing schedule. In embodiments, a second dosing schedule is an intermittent dosing schedule. In embodiments, a second dosing schedule is an intermittent dosing schedule comprising a treatment period of at least 1, 2, 3, 4, 5, 6, 7, 8, 9, 10, 11, 12, 13, or 14 days followed by a resting period of at least 1, 2, 3, 4, 5, 6, 7, 8, 9, 10, 11, 12, 13, or 14 days. In embodiments, a second dosing schedule comprises administering a second dose (e.g., a maintenance dose) every other day, every two days, or every 3, 4, 5, 6, 7, 8 days. In embodiments, a maintenance dose is administered for an extended period of time with or without titration (or otherwise changing the dosage or dosing schedule). In embodiments, the interval between a first and a second dosing schedule is at least about 1, 2, 3, 4, 5, 6, 7, 8, 9, 10, 11, or 12 weeks. In embodiments, a second dosing schedule (e.g., a maintenance dose) comprises a dosage about 2, 5, 10, 50, 100, 200, 400, 800, 1000, 5000 or more folds lower than the dosage used in a first dosing schedule (e.g., an initial treatment dose). In embodiments, a second dosing schedule (e.g., a maintenance dosing schedule) has an equal or lower dosing frequency than a first dosing schedule (e.g., an initial treatment dosing schedule). In embodiments, a second dosing schedule (e.g., a maintenance dosing schedule) has a higher dosing interval than a first dosing schedule (e.g., an initial treatment dosing schedule).

In embodiments, a first or second dosing schedule used in a method can be once-a-week, twice-a-week, or thrice-a-week. The term "once-a-week" means that a dose is administered once in a week, preferably on the same day of each week. "Twice-a-week" means that a dose is administered two times in a week, preferably on the same two days of each weekly period. "Thrice-a-week" means that a dose is administered three times in a week, preferably on the same three days of each weekly period.

In embodiments, the microbial composition may be administered, for example, more than once daily, about once per day, about every other day, about every third day, about once a week, about once every two weeks, about once every month, about once every two months, about once every three months, about once every six months, or about once every year.

In embodiments, a treatment method effects an increase in the efficacy of an anti-cancer therapy, or a prevention or reduction in the efficacy of an OTIC induced by an anti-cancer therapy. The change of flora is preferably as "near-complete" as possible and the flora is replaced by viable organisms which will crowd out any remaining, original flora. Typically, the change in enteric flora comprises introduction of an array of predetermined flora into the gastrointestinal system, and thus in a preferred form the method of treatment comprises substantially or completely displacing pathogenic enteric flora in patients requiring such treatment.

In embodiments, a subject in need thereof is administered a therapeutic composition comprising fecal microbiota of multiple screened, healthy donors. In embodiments, a subject is administered a therapeutic composition over a dosing period wherein a first dose comprises at least one therapeutic composition comprises fecal microbiota of a single donor, and a second dose of a therapeutic composition comprises fecal microbiota of a single donor different from the donor of the first dose. In embodiments, a first dose comprises a therapeutic composition comprising fecal microbiota of a single donor and a second dose comprises fecal microbiota of a donor pool. The first and second dose do not indicate the order of administration to a subject, but rather that fecal microbiota from separate donors may be used in a non-blended form.

In embodiments, the present disclosure provides for methods for treating a subject in need thereof with capsules containing a therapeutic composition comprising fecal microbiota from a single donor. In embodiments, a capsule comprises a therapeutic composition comprising fecal microbiota from multiple donors. In embodiments a subject is administered two or more pills comprising fecal microbiota from a single but different donor.

In embodiments, the present disclosure provides for methods for treating a subject in need thereof comprising administering a therapeutic composition orally or by infusions through a colonoscope, an enema or via a nasojejunal tube. In embodiments, each administration comprises a therapeutic composition comprising fecal microbiota of a single donor similar to or different from a prior administration in a treatment period. In embodiments, a treatment period includes administration of a first dost comprising a therapeutic composition comprising fecal microbiota of a single donor and administration of a second dose comprising a therapeutic composition comprising fecal microbiota of multiple donors.

In embodiments, a therapeutic composition can be provided together with a pharmaceutically acceptable carrier. As used herein, a "pharmaceutically acceptable carrier" refers to a non-toxic solvent, dispersant, excipient, adjuvant, or other material which is mixed with a live bacterium in order to permit the formation of a therapeutic composition, e.g., a dosage form capable of administration to the patient. A pharmaceutically acceptable carrier can be liquid (e.g., saline), gel or solid form of diluents, adjuvant, excipients or an acid resistant encapsulated ingredient. Suitable diluents and excipients include pharmaceutical grades of physiological saline, dextrose, glycerol, mannitol, lactose, starch, magnesium stearate, sodium saccharin, cellulose, magnesium carbonate, and the like, and combinations thereof. In embodiments, a therapeutic composition may contain auxiliary substances such as wetting or emulsifying agents, stabilizing or pH buffering agents. In embodiments, a therapeutic composition contains about 1%-5%, 5%-10%, 10%-15%, 15-20%, 20%-25%, 25-30%, 30-35%, 40-45%, 50%-55%, 1%-95%, 2%-95%, 5%-95%, 10%-95%, 15%-95%, 20%-95%, 25%-95%, 30%-95%, 35%-95%, 40%-95%, 45%-95%, 50%-95%, 55%-95%, 60%-95%, 65%-95%, 70%-95%, 45%-95%, 80%-95%, or 85%-95% of active ingredient. In embodiments, a therapeutic composition contains about 2%-70%, 5%-60%, 10%-50%, 15%-40%, 20%-30%, 25%-60%, 30%-60%, or 35%-60% of active ingredient.

In embodiments, a method comprises administering a therapeutic composition orally, by enema, or via rectal suppository. In embodiments, a therapeutic composition administered herein is formulated as an enteric coated (and/or acid-resistant) capsule or microcapsule, or formulated as part of or administered together with a food, a food additive, a dairy-based product, a soy-based product or a derivative thereof, a jelly, flavored liquid, ice block, ice cream, or a yogurt. In embodiments, a therapeutic composition administered herein is formulated as an acid-resistant enteric coated capsule. A therapeutic composition can be provided as a powder for sale in combination with a food or drink. A food or drink can be a dairy-based product or a soy-based product. In embodiments, a food or food supplement contains enteric-coated and/or acid-resistant microcapsules containing a therapeutic composition.

In embodiments, a therapeutic composition is in the form of: an enema composition which can be reconstituted with an appropriate diluent; enteric-coated capsules; enteric-coated microcapsules; acid-resistant tablet; acid-resistant capsules; acid-resistant microcapsules; powder for reconstitution with an appropriate diluent for naso-enteric infusion or colonoscopic infusion; powder for reconstitution with appropriate diluent, flavoring and gastric acid suppression agent for oral ingestion; powder for reconstitution with food or drink; or food or food supplement comprising enteric-coated and/or acid-resistant microcapsules of the composition, powder, jelly, or liquid.

In embodiments, a therapeutic composition comprises a liquid culture. In embodiments, a therapeutic composition is homogenized, lyophilized, pulverized and powdered. It may then be infused, dissolved such as in saline, as an enema. Alternatively, the powder may be encapsulated as enteric-coated and/or acid-resistant delayed release capsules for oral administration. In embodiments, the powder may be double encapsulated with acid-resistant/delayed release capsules for oral administration. These capsules may take the form of enteric-coated and/or acid-resistant delayed release microcapsules. A powder can preferably be provided in a palatable form for reconstitution for drinking or for reconstitution as a food additive. In embodiments, a food is yogurt. In embodiments, a powder may be reconstituted to be infused via naso-duodenal infusion.

In embodiments, a therapeutic composition administered herein is in a liquid, frozen, freeze-dried, spray-dried, foam-dried, lyophilized, or powder form. In embodiments, a therapeutic composition administered herein is formulated as a delayed or gradual enteric release form. In embodiments, a therapeutic composition administered herein comprises an excipient, a saline, a buffer, a buffering agent, or a fluid-glucose-cellobiose agar (RGCA) media. In embodiments, a therapeutic composition administered herein comprises a cryoprotectant. In embodiments, a cryoprotectant comprises polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof.

In embodiments, a therapeutic composition comprises a lyophilized formulation further comprising a reducing agent. In certain embodiments, the reducing agent comprises cysteine selected from the group consisting of D-cysteine and L-cysteine. In embodiments, cysteine is at a concentration of at least about 0.025%. In embodiments, cysteine is at a concentration of about 0.025%. In embodiments, cysteine is at a concentration of 0.025%. In embodiments, another reducing agent other than cysteine is used in lieu of, or in combination with cysteine. In embodiments, another reducing agent is selected from the group comprising ascorbic acid, sodium ascorbate, thioglycolic acid, sodium sulfite, sodium bisulfite, sodium metabisulfite, potassium metabisulfite, Glutathione, Methionine, thioglycerol, and alpha tocopherol.

In embodiments, cysteine is at a concentration of at least about 0.005%, at least about 0.01%, at least about 0.015%, at least about 0.02%, at least about 0.025%, at least about 0.03%, at least about 0.035%, at least about 0.04%, at least about 0.045%, at least about 0.05%, at least about 0.055%, at least about 0.06%, at least about 0.065%, at least about 0.07%, at least about 0.075%, at least about 0.08%, at least about 0.085%, at least about 0.09%, at least about 0.095%, at least about 0.1%, at least about 0.12%, at least about 0.14%, at least about 0.16%, at least about 0.18%, at least about 0.2%, at least about 0.25%, at least about 0.3%, at least about 0.4%, at least about 0.5%, at least about 0.6%, at least about 0.7%, at least about 0.8%, at least about 0.9%, at least about 1%, at least about 2%, at least about 4%, at least about 6%, at least about 8%, at least about 10%, at least about 12%, at least about 14%, at least about 16%, at least about 18%, at least about 20%, at least about 22%, at least about 24%, or at least about 26%.

In embodiments, a therapeutic composition comprises a cryoprotectant. As used herein, a "cryoprotectant" refers to a substance that is added to a formulation in order to protect an active ingredient during freezing. In embodiments, a cryoprotectant comprises, consists essentially of, or consists of polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof. In embodiments of the present disclosure, a cryoprotectant can be selected from the group comprising 5% Sucrose; 10% Sucrose; 10% Skim milk; 10% Trehalose with 2.5% sucrose; 5% Trehalose with 2.5% sucrose; 5% Mannitol; 5% Mannitol with 0.1% Polysorbate 80; 10% Mannitol; 10% Mannitol with 0.1% Polysorbate 80; 5% Trehalose; 5% Trehalose with 0.1% Polysorbate 80; 10% Trehalose; and 10% Trehalose with 0.1% Polysorbate 80.

In embodiments, a therapeutic composition comprises a lyoprotectant. As used herein, a "lyoprotectant" refers to a substance that is added to a formulation in order to protect an active ingredient during the drying stage of a lyophilization (also known as freeze-drying) process. In embodiments, the same substance or the same substance combination is used as both a cryoprotectant and a lyoprotectant. Illustrative lyoprotectants include sugars such as sucrose or trehalose; an amino acid such as monosodium glutamate or histidine; a methylamine such as betaine; a lyotropic salt such as magnesium sulfate; a polyol such as trihydric or higher sugar alcohols, e.g., glycerin, erythritol, glycerol, arabitol, xylitol, sorbitol, and mannitol; propylene glycol; polyethylene glycol; Pluronics; and combinations thereof. In embodiments, a lyoprotectant is a non-reducing sugar, such as trehalose or sucrose. In embodiments, a cryoprotectant or a lyoprotectant consists essentially of, or consists of, one or more substances mentioned in this paragraph and the paragraph above.

In embodiments, a cryoprotectant or a lyoprotectant comprise an intracellular agent, e.g., DMSO, Glycerol, or PEG, which penetrates inside the cell preventing the formation of ice crystals that could result in membrane rupture. In embodiments, a cryoprotectant or a lyoprotectant comprise an extracellular agent, e.g., sucrose, trehalose, or dextrose, which does not penetrate into the cell membrane but acts to improve the osmotic imbalance that occurs during freezing.

In embodiments, the present disclosure provides a therapeutic composition comprising a lyophilized fecal microbe preparation comprising a lyophilization formulation comprising at least about 12.5% trehalose.

In embodiments, a lyophilization formulation comprises at least about 5%, at least about 7.5%, at least about 10%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20%, at least about 22.5%, at least about 25%, at least about 27.5%, at least about 30%, at least about 32.5%, at least about 35%, at least about 37.5%, at least about 40%, at least about 42.5%, at least about 45%, at least about 47.5%, at least about 50%, at least about 52.5%, at least about 55%, at least about 57.5%, or at least about 60% of trehalose.

In embodiments, a subject being treated is a human patient. In embodiments, a patient is a male patient. In embodiments, a patient is a female patient. In embodiments, a patient is a premature newborn. In embodiments, a patient is a term newborn. In embodiments, a patient is a neonate. In embodiments, a patient is an infant. In embodiments, a patient is a toddler. In embodiments, a patient is a young child. In embodiments, a patient is a child. In embodiments, a patient is an adolescent. In embodiments, a patient is a pediatric patient. In embodiments, a patient is a geriatric patient. In embodiments, a human patient is a child patient whose age is below about 18, 15, 12, 10, 8, 6, 4, 3, 2, or 1 year. In embodiments, a human patient is an adult patient. In embodiments, a human patient is an elderly patient. In embodiments, a human patient is a patient above about 30, 35, 40, 45, 50, 55, 60, 65, 70, 75, 80, 85, 90, or 95 years old. In embodiments, a patient is about between 1 and 5, between 2 and 10, between 3 and 18, between 21 and 50, between 21 and 40, between 21 and 30, between 50 and 90, between 60 and 90, between 70 and 90, between 60 and 80, or between 65 and 75 years old. In embodiments, a patient is a young old patient (65-74 years). In embodiments, a patient is a middle old patient (75-84 years). In embodiments, a patient is an old patient (>85 years).

Prebiotics

In embodiments, a subject is administered a prebiotic before, contemporaneously with, and/or after an administration of a therapeutic composition comprising a microbial composition described herein, either in a therapeutic composition comprising the microbial composition or in a therapeutic composition lacking a microbial composition.

A prebiotic is a substrate that is selectively used by a host microorganism to produce a health benefit in a subject/patient. Without wishing to be bound by theory, prebiotics are added to nutritionally supplement bacteria in the microbiome and/or in a microbial composition, e.g., to stimulate the growth or activity of one or more strains of beneficial bacteria. Additionally, the prebiotics may be added to prevent "shock" to bacterial strains subsequent to their isolation or purification, freezing, freeze-drying, spray-drying, reconstitution in solution and the like.

Examples of prebiotics include amino acids, ammonium nitrate, amylose, barley mulch, biotin, carbonate, cellulose, chitin, choline, fructooligosaccharides (FOSs), fructose, galactooligosaccharides (GOSs), glucose, glycerol, heteropolysaccharide, histidine, homopolysaccharide, hydroxyapatite, inulin, isomaltulose, lactose, lactulose, maltodextrins, maltose, mannooligosaccharides, monosaccharides, tagatose, nitrogen, oligodextrose, oligofructoses, oligofructose-enriched inulin, oligosaccharides, pectin, phosphate salts, phosphorus, polydextroses, polyols, potash, potassium, sodium nitrate, starch, sucrose, sulfur, sun fiber, tagatose, thiamine, trans-galactooligosaccharides, trehalose, vitamins, a water-soluble carbohydrate, and/or xylooligosaccharides (XOSs).

In embodiments, a prebiotic can be added (e.g., in dry or liquid forms) to a microbial composition described herein.

A prebiotic may be provided in a single dose or in multiple doses. When provided as a single composition, the single composition may comprise a single prebiotic or a mixture of prebiotics. When provided in multiple compositions, each composition may comprise a single prebiotic or a mixture of prebiotics.

As examples, when multiple doses are provided, a first composition comprising a prebiotic may include one specific prebiotic, e.g., inulin, and a second composition may include a second specific prebiotic, e.g., pectin. Alternately, a first composition may include a mixture of prebiotics, e.g., inulin and pectin and a second composition may include different mixture of prebiotics, e.g., inulin and a FOS. A first composition may include a mixture of prebiotics and a second composition may include one specific prebiotic.

Alternately, or additionally, a prebiotic can be included (e.g., in dry or liquid forms) in a distinct therapeutic composition which lacks a microbial composition. Such a distinct composition can be administered to a subject before, concurrently with, or after administration of therapeutic compositions described herein containing a microbial composition.

The amount of prebiotic provided to a subject/patient and/or included in a composition depends on the specific prebiotic, the specific bacterial strain of beneficial bacteria, and/or the disease state of the subject/patient.

A prebiotic may be provided to a subject before, contemporaneously with, and/or after a therapeutic composition comprising a microbial composition, either in a therapeutic composition comprising the microbial composition or in a therapeutic composition lacking a microbial composition.

A prebiotic may be provided in a single dose or in multiple doses. When provided as a single composition, the single composition may comprise a single prebiotic or a mixture of prebiotics. When provided in multiple compositions, each composition may comprise a single prebiotic or a mixture of prebiotics.

As examples, when multiple doses are provided, a first composition comprising a prebiotic may include one specific prebiotic, e.g., inulin, and a second composition may include a second specific prebiotic, e.g., pectin. Alternately, a first composition may include a mixture of prebiotics, e.g., inulin and pectin and a second composition may include different mixture of prebiotics, e.g., inulin and a FOS. A first composition may include a mixture of prebiotics and a second composition may include one specific prebiotic.

The amount of prebiotic provided to a subject/patient and/or included in a composition depends on the specific prebiotic, the specific bacterial strain of beneficial bacteria, and/or the disease state of the subject In embodiments, a subject is not pretreated with a prebiotic nutrient prior to treatment with a therapeutic composition. In embodiments, the therapeutic composition is not supplemented with a prebiotic nutrient.

In embodiments, a subject is administered an antibiotic or antibiotic composition prior to being administered the therapeutic composition comprising the microbial composition. In embodiments, a subject is administered an antibiotic or an antibiotic composition while being administered the therapeutic composition comprising the microbial composition. In embodiments, an antibiotic composition administered herein comprises an antibiotic selected from the group consisting of rifabutin, clarithromycin, clofazimine, vancomycin, rifampicin, nitroimidazole, chloramphenicol, and a combination thereof. In embodiments, an antibiotic composition administered herein comprises an antibiotic selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof. In embodiments, a subject is not pretreated with an antibiotic composition prior to administering a therapeutic bacterial or microbiota composition. In embodiments, the therapeutic composition is not supplemented with an antibiotic composition. In embodiments, a method further comprises pretreating a subject with an anti-inflammatory drug prior to administration of a therapeutic bacterial or microbiota composition. In embodiments, a subject is not pretreated with an anti-inflammatory drug prior to administering a therapeutic bacterial or microbiota composition. In embodiments, a therapeutic bacterial or microbiota composition is not supplemented with an anti-inflammatory.

In embodiments, a subject is administered a non-antibiotic antimicrobial drug prior to being administered the therapeutic composition comprising the microbial composition. In embodiments, a subject is administered a non-antibiotic antimicrobial drug or a non-antibiotic antimicrobial composition while being administered the therapeutic composition comprising the microbial composition. In embodiments, the non-antibiotic antimicrobial drug is an antifungal drug, an antiviral drug, or an antiparasitic drug. In embodiments, the antifungal drug is selected from Abafungin, Albaconazole, amorolfin, Amphotericin B, Anidulafungin, Bifonazole, butenafine, Butoconazole, Candicidin, Caspofungin, Clotrimazole, Econazole, Efinaconazole, Epoxiconazole, Fenticonazole, Filipin, Fluconazole, Hamycin, Isavuconazole, Isoconazole, Itraconazole, Ketoconazole, Luliconazole, Micafungin, Miconazole, naftifine, Natamycin, Nystatin, Omoconazole, Oxiconazole, Posaconazole, Propiconazole, Ravuconazole, Rimocidin, Sertaconazole, Sulconazole, terbinafine, Terconazole, Tioconazole, and Voriconazole. In embodiments, the antiviral drug is selected from Abacavir, Acyclovir (Aciclovir), Adefovir, Amantadine, Amprenavir (Agenerase), Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fixed dose combination (antiretroviral), Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nitazoxanide, Nucleoside analogues, Norvir, Oseltamivir (Tamiflu), Peginterferon alfa-2a, Penciclovir, Peramivir, Pleconaril, Podophyllotoxin, Protease inhibitor (pharmacology), Raltegravir, Reverse transcriptase inhibitor, Ribavirin, Rimantadine, Ritonavir, Pyramidine, Saquinavir, Sofosbuvir, Stavudine, Synergistic enhancer (antiretroviral), Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), and Zidovudine. In embodiments, the antiparasitic drug is selected from Albendazole, Amphotericin B, Antihelminthic, Diethylcarbamazine, Eflornithine, Ivermectin, Mebendazole, Melarsoprol, Metronidazole, Miltefosine, Niclosamide, Nitazoxanide, Praziquantel, Praziquantel, Pyrantel pamoate, Rifampin, Thiabendazole, and Tinidazole. In embodiments, a subject is not pretreated with a non-antibiotic antimicrobial drug prior to administering a therapeutic bacterial or microbiota composition.

In embodiments, a subject's bowels are prepared prior to being administered the therapeutic composition comprising the microbial composition. In embodiments, the bowels are prepared by fasting, e.g., for about one to about three days. In embodiments, the bowels are prepared by orally administering an agent, e.g., excess dietary fiber, herbs, juices, teas, enzymes, magnesium, dietary supplements, prebiotics, and/or laxatives, and/or by aborally administering an aboral colon cleanse, e.g., via colon hydrotherapy, a colonic, or colonic irrigation. In embodiments, a subjects' bowels may be prepared by combinations of fasting, oral agents, and/or aboral colon cleanses. In embodiments, the subject does not have his/her bowels prepared prior to being administered the therapeutic composition comprising the microbial composition.

Therapeutic Compositions Comprising Additional Therapeutic Agents

Described herein are therapeutic compositions comprising a microbial composition and one or more additional therapeutic agents.

A therapeutic composition comprising a microbial composition may further comprise one or more additional therapeutic agents. The one or more additional therapeutic agents and the microbial composition may be combined and encapsulated together in a capsule. Alternately, the one or more additional therapeutic agents may be included in a layer coating a capsule which encapsulates the microbial composition.

In embodiments, an additional therapeutic agent is an anti-inflammatory agent such as steroidal anti-inflammatory agents or non-steroidal anti-inflammatory agents (NSAIDS). Steroids, particularly the adrenal corticosteroids and their synthetic analogues, are well known in the art. Examples of corticosteroids that may be useful include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. Additional anti-inflammatory agents are described, for example, in U.S. Pat. No. 4,537,776, the entire contents of which are incorporated by reference herein.

In embodiments, an additional therapeutic agent is an acid suppressant, an antacid, an H2 antagonist, a proton pump inhibitor or a combination thereof. In embodiments, a therapeutic composition is combined with other adjuvants such as antacids to dampen bacterial inactivation in the stomach. (e.g., Mylanta, Mucaine, and Gastrogel). In embodiments, acid secretion in the stomach could also be pharmacologically suppressed using H2-antagonists or proton pump inhibitors. An example H2-antagonist is ranitidine. An example proton pump inhibitor is omeprazole. In embodiments, an acid suppressant is administered prior to administering, or in co-administration with, a therapeutic composition.

In embodiments, a therapeutic composition administered does not comprise an acid suppressant, an antacid, an H2 antagonist, a proton pump inhibitor or a combination thereof. In embodiments, a therapeutic composition administered does not comprise an acid suppressant. In embodiments, a therapeutic composition administered does not comprise an antacid. In embodiments, a therapeutic composition administered does not comprise an H2 antagonist. In embodiments, a therapeutic composition administered does not comprise a proton pump inhibitor. In embodiments, a therapeutic composition administered does not comprise metoclopramide.

In embodiments, an additional therapeutic agent is a probiotic. Probiotics suitable for use include, but are not limited to, a *Parabacteroides* species, *Saccharomyces boulardii; Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus* (Bio-K+CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve*, and *Streptococcus salivarius* subsp. *thermophilus* (VSL #3)).

In embodiments, the present disclosure provides for administering a probiotic prior to administering a therapeutic composition comprising a non-selected fecal microbiota. In embodiments, the disclosure provides for co-administering a probiotic and a therapeutic composition comprising a non-selected fecal microbiota. In embodiments, the probiotic is selected from the group consisting of one or more *Parabacteroides* species. In embodiments, the probiotic is selected from the group consisting of two or more *Parabacteroides* species. In embodiments, the probiotic is selected from the group consisting of three or more *Parabacteroides* species. In embodiments, the probiotic is selected from the group consisting of four or more *Parabacteroides* species. In embodiments, the probiotic is selected from the group consisting of five or more *Parabacteroides* species. In embodiments, the probiotic is selected from the group consisting of six or more *Parabacteroides* species. In embodiments, the probiotic is selected from the group consisting of 1 to 3, 3 to 5, 5 to 8, or 8 to 10 *Parabacteroides* species. A probiotic may be provided in a single dose or in multiple doses. When provided as a single composition, the single composition may comprise a single probiotic or a mixture of probiotics. When provided in multiple compositions, each composition may comprise a single probiotic or a mixture of probiotics.

In embodiments, an additional therapeutic agent is a prebiotic as described elsewhere herein. In embodiments, a prebiotic can be added (e.g., in dry or liquid forms) to a therapeutic composition described herein. The amount of prebiotic provided to a subject/patient and/or included in a composition depends on the specific prebiotic, the specific bacterial strain of beneficial bacteria, and/or the disease state of the subject/patient.

In embodiments, an additional therapeutic agent is an antidiarrheal or anti-constipation agent. Antidiarrheal agents suitable for use include, but are not limited to, DPP-IV inhibitors, natural opioids, such as tincture of opium, paregoric, and codeine, synthetic opioids, such as diphenoxylate, difenoxin and loperamide, bismuth subsalicylate, lanreotide, vapreotide and octreotide, motiln antagonists, COX2 inhibitors like celecoxib, glutamine, thalidomide and traditional antidiarrheal remedies, such as kaolin, pectin, berberine and muscarinic agents.

In embodiments, an additional therapeutic agent is an analgesic. Analgesics suitable for use include, but are not limited to, morphine, codeine, heroine, methadone and related compounds, thebaine, orpiavine, and their derivatives, buprenorphine, the piperidines, morphinans, benzomorphans, tetrahydroisoquinolines, thiambutanes, benzylamines, tilidine, viminol, nefopam, capsaicin(8-methyl-N-vanillyl-6E-nonenamide), "synthetic" capsaicin(N-vanillylnonamide), and related compounds.

In embodiments, an additional therapeutic agent is an antibacterial agent. Antibacterial agents suitable for use include, but are not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In embodiments, the anti-bacterial agent may be any of the penicillin, cephalosporin, monobactam, and carbapenem antibiotics.

In embodiments, an additional therapeutic agent includes, but is not limited to, short-chain fatty acids, butyrate, propionate, acetate, IL-2, IL-22, superoxide dismutase (SOD), GLP-2 and analogs, GLP-1, IL-10, IL-27, TGF-δ1, TGF-β2, N-acylphosphatidylethanolamines (NAPEs), elafin (also called peptidase inhibitor 3 and SKALP), trefoil factor, melatonin, tryptophan, PGD2, and kynurenic acid, indole metabolites, and other tryptophan metabolites.

In embodiments, the additional therapeutic agent is an anti-cancer therapeutic agent. The anti-cancer therapeutic agent may be a chemotherapeutic agent as described elsewhere herein.

In a therapeutic composition described herein, a chemotherapeutic agent that can be formulated for oral administration and the microbial composition may be combined and encapsulated together in a capsule. Alternately, the chemotherapeutic agent may be included in a layer coating a capsule which encapsulates the microbial composition. In embodiments, the chemotherapeutic agent and the therapeutic composition comprising the microbial composition are in separate dosage forms.

In embodiments, any chemotherapeutic agent that can be formulated for oral administration may be used. Examples of such chemotherapeutic agents include Afinitor (everolimus), Alecensa (alectinib), Alkeran (melphalan), Alunbrig (brigatinib), Arimidex (anastrozole), Aromasin (exemestane), Binimetinib (Mektovi), Bosulif (bosutinib), Cabometyx (cabozantinib), Caprelsa (vandetanib), Casodex (bicalutamide), Cometriq (cabozantinib), Cotellic (cobimetinib), Cyclophosphamide (cyclophosphamide caps), Cytoxan (Cyclophosphamide), Droxia (hydroxyurea), Emcyt (estramustine), Encorafenib (Braftovi), Erivedge (vismodegib), etoposide, Fareston (toremifene citrate), Farydak (panobinostat), Femara (letrozole), flutamide, Gilotrif (afatinib), Gleevec (imatinib), Gleostine (lomustine), Hexalen (altretamine), Hycamtin (topotecan), Hydrea (hydroxyurea), Ibrance (palbociclib), Iclusig (ponatinib), Idamycin (Idarubicin), Idhifa (enasidenib), Imbruvica (ibrutinib), Inlyta (axitinib), Iressa (gefitinib), Jakafi (ruxolitinib), Kisqali (ribociclib), Kisqali Femara Co-Pack (ribociclib and letrozole), Lenvima (lenvatinib), leucovorin, Leukeran (chlorambucil), Lonsurf (trifluridine/tipiracil), Lynparza (olaparib), Lysodren (mitotane), Matulane (procarbazine), Megace (megestrol acetate), Mekinist (trametinib), mercaptopurine, Mesnex (mesna), methotrexate, Myleran (busulfan), Navelbine (Vinorelbine), Nerlynx (neratinib), Nexavar (sorafenib), Nilandron (nilutamide), Ninlaro (ixazomib), Odomzo (sonidegib), Pomalyst (pomalidomide), Purixan (mercaptopurine susp), Revlimid (lenalidomide), Rubraca (rucaparib), Rydapt (midostaurin), Soltamox (tamoxifen citrate), Sprycel (dasatinib), Stivarga (regorafenib), Sutent (sunitinib), Tabloid (thioguanine), Tafinlar (dabrafenib), Tagrisso (osimertinib), tamoxifen, Tarceva (erlotinib), Targretin (bexarotene), Tasigna (nilotinib), Temodar (temozolomide), Thalomid (thalidomide), Toposar (Etoposide), tretinoin, Trexall (methotrexate), Tykerb (lapatinib), Venclexta (venetoclax), Votrient (pazopanib), Xalkori (crizotinib), Xatmep (methotrexate soln), Xeloda (capecitabinea), Xtandi (enzalutamide), Zejula (niraparib), Zelboraf (vemurafenib), Zolinza (vorinostat), Zydelig (idelalisib), Zykadia (ceritinib), or Zytiga (abiraterone), and a combination thereof.

In embodiments, the therapeutic composition lacks a chemotherapeutic agent, yet, the chemotherapeutic agent and the therapeutic composition are administered simultaneously. The term "simultaneously" as used herein, means that the chemotherapeutic agent and the therapeutic composition are administered with a time separation of no more than about 60 minutes, such as no more than about 30 minutes, no more than about 20 minutes, no more than about 10 minutes, no more than about 5 minutes, or no more than about 1 minute. Alternately, "simultaneously" can mean the therapeutic composition which lacks a chemotherapeutic agent and the chemotherapeutic agent have been administered at different times yet both have not been fully metabolized and/or excreted from the subject's body.

In embodiments, the chemotherapeutic agent and the therapeutic composition comprising a microbial composition are administered to a subject simultaneously but the release of the chemotherapeutic agent and the microbial composition from their respective dosage forms (or single unit dosage form if co-formulated) in the GI tract occurs sequentially.

Administering Therapeutic Compositions and an Anti-Cancer Therapy

In embodiments, a therapeutic composition is administered simultaneously (as described herein) with the anti-cancer therapy.

Alternately, the therapeutic composition and the anti-cancer therapy are administered sequentially. The term "sequentially" as used herein means that the anti-cancer therapy and the therapeutic composition are administered with a time separation of more than about 60 minutes. For example, the time between the sequential administration of the anti-cancer therapy and the therapeutic composition can be more than about 60 minutes, more than about 2 hours, more than about 5 hours, more than about 10 hours, more than about 1 day, more than about 2 days, more than about 3 days, more than about 1 week apart, more than 1 month apart, or longer. The optimal administration time will depend on the specific anti-cancer therapy and the therapeutic composition being administered. Either the anti-cancer therapy or the therapeutic composition may be administered first. In embodiments, the subject is administered therapeutic composition prior to the anti-cancer therapy, thereby helping ensure that the subject has a healthy gut biome prior to receiving the anti-cancer therapy. Alternately, the subject is administered therapeutic composition after the anti-cancer therapy, thereby helping the subject repair/repopulate his/her gut biome after receiving the anti-cancer therapy.

In embodiments, the anti-cancer therapy is a radiation therapy.

In embodiments, the anti-cancer therapy is a surgery, i.e., to excise a tumor or an organ/tissue comprising cancerous cells.

In embodiments, the anti-cancer therapy comprises administration of a chemotherapeutic agent. Examples of chemotherapeutic agents include 5-FU (Fluorouracil), Abemaciclib, Abiraterone Acetate, Abitrexate (Methotrexate), Abraxane (Paclitaxel Albumin-stabilized Nanoparticle Formulation), ABVD, ABVE, ABVE-PC, AC, Acalabrutinib, AC-T, ADE, Adriamycin (Doxorubicin), Afatinib Dimaleate, Afinitor (Everolimus), Afinitor Difsperz (Everolimus), Akynzeo (Netupitant and Palonosetron), Aldara (Imiquimod), Aldesleukin, Alecensa (Alectinib), Alectinib, Alimta (PEMETREXED), Aliqopa (Copanlisib Hydrochloride), Alkeran (Melphalan), Aloxi (Palonosetron Hydrochloride), Alunbrig (Brigatinib), Ambochlorin (Chlorambucil), Amboclorin (Chlorambucil), Amifostine, Aminolevulinic Acid, Anastrozole, Aprepitant, Aredia (Pamidronate), Arimidex (Anastrozole), Aromasin (Exemestane), Arranon (Nelarabine), Arsenic Trioxide, Asparaginase *Erwinia chrysanthemi*, Axicabtagene Ciloleucel, Axitinib, Azacitidine, BEACOPP, Becenum (Carmustine), Beleodaq (Belinostat), Belinostat, Bendamustine Hydrochloride, BEP, Bexarotene, Bicalutamide, BiCNU (Carmustine), Binimetinib (Mektovi), Blenoxane (Bleomycin), Bortezomib, Bosulif (Bosutinib), Bosutinib, Brigatinib, BuMel, Busulfan, Busulfex (Busulfan)C, Cabazitaxel, Cabometyx (Cabozantinib), Cabozantinib-S-Malate, CAF, Calquence (Acalabrutinib), Camptosar (Irinotecan Hydrochloride), Capecitabine, CAPDX, Caprelsa (Vandetanib), Carac (Fluorouracil-Topical), Carboplatin, CARBOPLATIN-TAXOL, Carfilzomib, Carmubris (Carmustine), Carmustine, Casodex (Bicalutamide), CeeNU (Lomustine), CEM, Ceritinib, Cerubidine (Daunorubicin), Cervarix (Recombinant HPV Bivalent Vaccine), CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cytarabine, Cytarabine Liposome, Cytosar-U (Cytarabine), Cytoxan (Cyclophosphamide), Cytoxan (Cytoxan), Dabrafenib, Dacarbazine, Dacogen (Decitabine), Dactinomycin, Dasatinib, Daunorubicin Hydrochloride, Daunorubicin Hydrochloride and Cytarabine Liposome, DaunoXome (Daunorubicin Lipid Complex), Decadron (Dexamethasone), Decitabine, Defibrotide Sodium, Defitelio (Defibrotide Sodium), Degarelix, Denileukin Diftitox, DepoCyt (Cytarabine Liposome), Dexamethasone, Dexamethasone Intensol (Dexamethasone), Dexpak Taperpak (Dexamethasone), Dexrazoxane Hydrochloride, Docefrez (Docetaxel), Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), Droxia (Hydroxyurea), DTIC (Decarbazine), DTIC-Dome (Dacarbazine), Encorafenib (Braftovi), Efudex (Fluorouracil-Topical), Eligard (Leuprolide), Elitek (Rasburicase), Ellence (Ellence (epirubicin)), Eloxatin (Oxaliplatin), Elspar (Asparaginase), Eltrombopag Olamine, Emcyt (Estramustine), Emend (Aprepitant), Enasidenib Mesylate, Enzalutamide, Epirubicin Hydrochloride, EPOCH, Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Eulexin (Flutamide), Evacet (Doxorubicin Hydrochloride Liposome), Everolimus, Evista (Raloxifene Hydrochloride), Evomela (Melphalan Hydrochloride), Exemestane, Fareston (Toremifene), Farydak (Panobinostat), Faslodex (Fulvestrant), FEC, Femara (Letrozole), Filgrastim, Firmagon (Degarelix), FloPred (Prednisolone), Fludara (Fludarabine), Fludarabine Phosphate, Fluoroplex (Fluorouracil), Fluorouracil, Flutamide, Folex (Methotrexate), Folex PFS (Methotrexate), FOLFIRI, FOLFIRINOX, FOLFOX, Folotyn (Pralatrexate), FUDR (FUDR (floxuridine)), FU-LV, Fulvestrant, Gardasil (Recombinant HPV Quadrivalent Vaccine), Gardasil 9 (Recombinant HPV Nonavalent Vaccine), Gefitinib, Gemcitabine Hydrochloride, GEMCITABINE-CISPLATIN, GEMCITABINE-OXALIPLATIN, Gemzar (Gemcitabine), Gilotrif (Afatinib Dimaleate), Gilotrif (Afatinib), Gleevec (Imatinib Mesylate), Gliadel (Carmustine), Glucarpidase, Goserelin Acetate, Halaven (Eribulin Mesylate), Hemangeol (Propranolol Hydrochloride), Hexalen (Altretamine), HPV Bivalent Vaccine, Recombinant, HPV Nonavalent Vaccine, Recombinant, HPV Quadrivalent Vaccine, Recombinant, Hycamtin (Topotecan Hydrochloride), Hycamtin (Topotecan), Hydrea (Hydroxyurea), Hydroxyurea, Hyper-CVAD, I brance (Palbociclib), Ibrutinib, ICE, Iclusig (Ponatinib), Idamycin PFS (Idarubicin), Idarubicin Hydrochloride, Idelalisib, Idhifa (Enasidenib), Ifex (Ifosfamide), Ifosfamide, Ifosfamidum (Ifosfamide), Imatinib Mesylate, Imbruvica (Ibrutinib), Imiquimod, Imlygic (Talimogene Laherparepvec), Inlyta (Axitinib), Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), Jakafi (Ruxolitinib), JEB, Jevtana (Cabazitaxel), Keoxifene (Raloxifene Hydrochloride), Kepivance (Palifermin), Kisqali (Ribociclib), Kyprolis (Carfilzomib), Lanreotide Acetate, Lanvima (Lenvatinib), Lapatinib Ditosylate, Lenalidomide, Lenvatinib Mesylate, Lenvima (Lenvatinib Mesylate), Letrozole, Leucovorin Calcium, Leukeran (Chlorambucil), Leukine (Sargramostim), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil), Lupron (Leuprolide), Lynparza (Olaparib), Lysodren (Mitotane), Marqibo (Vincristine Sulfate Liposome), Marqibo Kit (Vincristine Lipid Complex), Matulane (Procarbazine), Mechlorethamine Hydrochloride, Megace (Megestrol), Megestrol Acetate, Mekinist (Trametinib), Melphalan, Melphalan Hydrochloride, Mercaptopurine, Mesnex (Mesna), Metastron (Strontium-89 Chloride), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mostarina (Prednimustine), Mozobil (Plerixafor), Mustargen (Mechlorethamine), Mutamycin (Mitomycin), Myleran (Busulfan), Mylosar (Azacitidine), Nanoparticle Paclitaxel (Paclitaxel Albumin-stabilized Nanoparticle Formulation), Navelbine (Vinorelbine), Nelarabine, Neosar (Cyclophosphamide), Neratinib Maleate, Nerlynx (Neratinib), Netupitant and Palonosetron Hydrochloride, Neulasta (filgrastim), Neulasta (pegfilgrastim), Neupogen (filgrastim), Nexavar (Sorafenib), Nilandron (Nilutamide), Nilotinib, Nilutamide, Ninlaro (Ixazomib), Nipent (Pentostatin), Niraparib Tosylate Monohydrate, Nolvadex (Tamoxifen), Novantrone (Mitoxantrone), Nplate (Romiplostim), Odomzo (Sonidegib), OEPA, OFF, Olaparib, Omacetaxine Mepesuccinate, Oncaspar (Pegaspargase), Oncovin (Vincristine), Ondansetron Hydrochloride, Onivyde (Irinotecan Hydrochloride Liposome), Ontak (Denileukin Diftitox), Onxol (Paclitaxel), OPPA, Oprred (Prednisolone), Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panobinostat, Panretin (Alitretinoin), Paraplat (Carboplatin), Pazopanib Hydrochloride, PCV, PEB, Pediapred (Prednisolone), Pegaspargase, Pegfilgrastim, Pemetrexed Disodium, Platinol (Cisplatin), PlatinolAQ (Cisplatin), Plerixafor, Pomalyst (Pomalidomide), Ponatinib Hydrochloride, Pralatrexate, Prednisone, Procarbazine Hydrochloride, Proleukin (Aldesleukin), Promacta (Eltrombopag Olamine), Propranolol Hydrochloride, Purinethol (Mercaptopurine), Purixan (Mercaptopurine), Radium 223 Dichloride, Raloxifene Hydrochloride, Rasburicase, R-CHOP, R-CVP, Reclast (Zoledronic acid), Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Regorafenib, Relistor (Methylnaltrexone Bromide), R-EPOCH, Revlimid (Lenalidomide), Rheumatrex (Methotrexate), Ribociclib, R-ICE, Rolapitant Hydrochloride, Romidepsin, Romiplostim, Rubex (Doxorubicin), Rubidomycin (Daunorubicin Hydrochloride), Rubraca (Rucaparib), Rucaparib Camsylate, Ruxolitinib Phosphate, Rydapt (Midostaurin), Sandostatin (Octreotide), Sandostatin LAR Depot (Octreotide), Sclerosol Intrapleural Aerosol (Talc), Soltamox (Tamoxifen), Somatuline Depot (Lanreotide Acetate), Sonidegib, Sorafenib Tosylate, Sprycel (Dasatinib), STANFORD V, Sterapred (Prednisone), Sterapred DS (Prednisone), Sterile Talc Powder (Talc), Steritalc (Talc), Sterecyst (Prednimustine), Stivarga (Regorafenib), Sunitinib Malate, Supprelin LA (Histrelin), Sutent (Sunitinib Malate), Sutent (Sunitinib), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib), Targretin (Bexarotene), Tasigna (Decarbazine), Tasigna (Nilotinib), Taxol (Paclitaxel), Taxotere (Docetaxel), Temodar (Temozolomide), Temozolomide, Temsirolimus, Tepadina (Thiotepa), Thalidomide, Thalomid (Thalidomide), TheraCys BCG (BCG), Thioguanine, Thioplex (Thiotepa), Thiotepa, TICE BCG (BCG), Tisagenlecleucel, Tolak (Fluorouracil-Topical), Toposar (Etoposide), Topotecan Hydrochloride, Toremifene, Torisel (Temsirolimus), Totect (Dexrazoxane Hydrochloride), TPF, Trabectedin, Trametinib, Treanda (Bendamustine hydrochloride), Trelstar (Triptorelin), Trexall (Methotrexate), Trifluridine and Tipiracil Hydrochloride, Trisenox (Arsenic trioxide), Tykerb (lapatinib), Uridine Triacetate, VAC, Valrubicin, Valstar (Valrubicin I ntravesical), Valstar (Valrubicin), VAMP, Vandetanib, Vantas (Histrelin), Varubi (Rolapitant), VeIP, Velban (Vinblastine), Velcade (Bortezomib), Velsar (Vinblastine Sulfate), Vemurafenib, Venclexta (Venetoclax), Vepesid (Etoposide), Verzenio (Abemaciclib), Vesanoid (Tretinoin), Viadur (Leuprolide Acetate), Vidaza (Azacitidine), Vinblastine Sulfate, Vincasar PFS (Vincristine), Vincrex (Vincristine), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib), Vumon (Teniposide), Vyxeos (Daunorubicin Hydrochloride and Cytarabine Liposome), W, Wellcovorin (Leucovorin Calcium), Wellcovorin IV (Leucovorin), Xalkori (Crizotinib), XELIRI, Xeloda (Capecitabine), XELOX, Xofigo (Radium 223 Dichloride), Xtandi (Enzalutamide), Yescarta (Axicabtagene Ciloleucel), Yondelis (Trabectedin), Zaltrap (Ziv-Aflibercept), Zanosar (Streptozocin), Zarxio (Filgrastim), Zejula (Niraparib), Zelboraf (Vemurafenib), Zinecard (Dexrazoxane Hydrochloride), Ziv-Aflibercept, Zofran (Ondansetron Hydrochloride), Zoladex (Goserelin), Zoledronic Acid, Zolinza (Vorinostat), Zometa (Zoledronic acid), Zortress (Everolimus), Zydelig (Idelalisib), Zykadia (Ceritinib), Zytiga (Abiraterone Acetate), and Zytiga (Abiraterone).

In embodiments, the anti-cancer therapy is an immuno-oncology therapy. An immuno-oncology therapy comprises at least one molecule capable of binding and/or recognizing a tumor-cell antigen and/or a cancer-cell antigen. Examples, tumor-cell antigens and/or a cancer-cell antigens include but are not limited to, carbonic anhydrase IX (CAIX), 5T4, CD19, CD20, CD22, CD30, CD33, CD38, CD47, CS1, CD138, Lewis-Y, L1-CAM, MUC16, ROR-1, IL13R$\alpha$2, gp100, prostate stem cell antigen (PSCA), prostate-specific membrane antigen (PSMA), B-cell maturation antigen (BCMA), human papillomavirus type 16 E6 (HPV-16 E6), CD171, folate receptor alpha (FR-$\alpha$), GD2, human epidermal growth factor receptor 2 (HER2), mesothelin, EGFRvIII, fibroblast activation protein (FAP), carcinoembryonic antigen (CEA), and vascular endothelial growth factor receptor 2 (VEGF-R2), as well as other tumor antigens well known in the art. Additional illustrative tumor antigens include, but are not limited to MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, $\alpha$-fetoprotein, E-cadherin, $\alpha$-catenin, $\beta$-catenin and $\gamma$-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD37, CD56, CD70, CD74, CD138, AGS16, MUC1, GPNMB, Ep-CAM, PD-L1, and PD-L2.

In embodiments, the tumor-cell antigen and/or a cancer-cell antigen is a checkpoint molecule. The checkpoint molecule may be a stimulatory checkpoint molecule, e.g., CD27, CD28, CD40, CD122, CD137, OX40, GITR, and ICOS. The checkpoint molecule may be an inhibitory checkpoint molecule, e.g., 2B4, A2AR, B-7 family ligands (including, but are not limited to, B7-1, B7-2, B7-DC, B7-H1, B7-H2, B7-H3, B7-H4, B7-H5, B7-H6 and B7-H7), BTLA, CD115, CD160/By55, CD172a/SIRP$\alpha$, CD200, CD223, CD244, CEACAM, CHK 1 and CHK2 kinases, CTLA-4, GAL9, HVEM, IDO, KIR, LAG3, PD-1, PD-L1, PD-L2, TIGIT, TIM-3, TMIGD2, and VISTA/VSIG8.

In embodiments, the immuno-oncology therapy is protein-based, e.g., antibody, fusion protein, and/or cytokine.

In embodiments, the antibody is Adcetris (Brentuximab Vedotin), Ado-Trastuzumab Emtansine, Alemtuzumab, Arzerra (Ofatumumab), Atezolizumab, Avastin (Bevacizumab), Avelumab, Bavencio (Avelumab), Besponsa (Inotuzumab Ozogamicin), Bevacizumab, Bexxar (Tositumomab), Blinatumomab, Blincyto (Blinatumomab), BMS 936559, Brentuximab Vedotin, Campath (Alemtuzumab), Cetuximab, Cinqair (Reslizumab), Cyramza (Ramucirumab), Daratumumab, Darzalex (Daratumumab), Denosumab, Dinutuximab, Durvalumab, Elotuzumab, Empliciti (Elotuzumab), Erbitux (Cetuximab), Folfiri-Bevacizumab, Folfiri-Cetuximab, Gazyva (Obinutuzumab), Gemtuzumab Ozogamicin, Herceptin (Trastuzumab), Ibritumomab Tiuxetan, lmfinzi (Durvalumab), Inotuzumab Ozogamicin, Ipilimumab, Kadcyla (Ado-trastuzumab Emtansine), KEYTRUDA (Pembrolizumab), Lartruvo (Olaratumab), MK-3475, MPDL3280A, Mylotarg (Gemtuzumab Ozogamicin), Necitumumab, Nivolumab, Obinutuzumab, Ofatumumab, Olaratumab, OPDIVO (Nivolumab), Panitumumab, Perjeta (Pertuzumab), Pertuzumab, Pembrolizumab, Pidilizumab, Portrazza (Necitumumab), Prolia (Denosumab), Ramucirumab, Rituxan (Rituximab), Rituximab and Hyaluronidase Human, Siltuximab, Sylvant (Siltuximab), Tecentriq (Atezolizumab), Trastuzumab, Unituxin (Dinutuximab), Vectibix (Panitumumab), Xgeva (Denosumab), YERVOY (Ipilimumab), and Zevalin (Ibritumomab Tiuxetan).

In embodiments, the immuno-oncology therapy includes an engineered protein or a fusion protein. In embodiments, the engineered protein or fusion protein binds to one or more tumor-cell antigens and/or cancer-cell antigens. In embodiments, the fusion protein binds to one or more tumor-cell antigens and/or cancer-cell antigens and is conjugated to a chemotherapeutic agent (as described herein).

In embodiments, the immuno-oncology therapy includes a cytokine, e.g., which binds to one or more tumor-cell antigens and/or cancer-cell antigens. In embodiments, the cytokine is Interferon Alfa-2b, Interleukin-2 (Aldesleukin), Intron A alfab (Interferon alfa-2a), Peginterferon Alfa-2b, PEG-Intron (Peginterferon Alfa-2b), Recombinant Interferon Alfa-2b, RoferonA alfaa (Interferon alfa-2a), and Sylatron (Peginterferon Alfa-2b).

In embodiments, binding and/or recognizing a tumor-cell antigen and/or a cancer-cell antigen blocks and/or prevents downstream signaling of the tumor-cell antigen and/or cancer-cell antigen. Alternately, binding and/or recognizing a tumor-cell antigen and/or a cancer-cell antigen activates and/or stimulates downstream signaling of the tumor-cell antigen and/or cancer-cell antigen.

In embodiments, the immuno-oncology therapy is a cell-based immuno-oncology therapy, e.g., relating to adoptive cell transfer (ACT). The ACT may be autologous or allogenic.

In embodiments, the cell-based immuno-oncology therapy comprises use of Chimeric Antigen Receptor (CAR) T-cell. Illustrative CAR T-cell therapy include, but are not limited to, JCAR014 (Juno Therapeutics), JCAR015 (Juno Therapeutics), JCAR017 (Juno Therapeutics), JCAR018 (Juno Therapeutics), JCAR020 (Juno Therapeutics), JCAR023 (Juno Therapeutics), JCAR024 (Juno Therapeutics), CTL019 (Novartis), Kymriah (or tisagenlecleucel; Novartis), KTE-C19 (Kite Pharma), BPX-401 (Bellicum Pharmaceuticals), BPX-501 (Bellicum Pharmaceuticals), BPX-601 (Bellicum Pharmaceuticals), bb2121 (Bluebird Bio), CD-19 Sleeping Beauty cells (Ziopharm Oncology), UCART19 (Cellectis), UCART123 (Cellectis), UCART38 (Cellectis), UCARTCS1 (Cellectis), OXB-302 (Oxford Bio-Medica, MB-101 (Mustang Bio), and CAR T-cells developed by Innovative Cellular Therapeutics.

In embodiments, the cell-based immuno-oncology therapy comprises use of an antigen-presenting cell (APC). In embodiments, the APC-related therapy comprises use of dendritic cells or other APCs that express tumor-cell antigens or cancer-cell antigens (as described herein). In one example, the APC is Sipuleucel-T (APC8015, trade name Provenge; Dendreon Corporation).

In embodiments, the cell-based immuno-oncology therapy comprises use of engineered T Cell Receptors (TCR) which recognize tumor-cell antigens or cancer-cell antigens (as described herein).

In embodiments, the cell-based immuno-oncology therapy comprises use of tumor infiltrating lymphocytes (TIL), e.g., adoptive transfer of TILs, which recognize tumor-cell antigens or cancer-cell antigens (as described herein).

In embodiments, the targeted therapy comprises a STING agonist, e.g., 5,6-dimethylxanthenone-4-acetic acid (DMXAA), MIW815(ADU-S100), or MK-1454.

In embodiments, the targeted therapy comprises an interleukin, e.g., IL-21 or IL-15.

In embodiments, the anti-cancer therapy is a stem-cell transplant therapy comprising a peripheral blood transplant, a bone marrow transplant, a cord blood transplant, or a skin-derived stem cell transplant.

Cancer

Cancers refer to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also, included are cells having abnormal proliferation that is not impeded by the immune system (e.g., virus infected cells). The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

The cancer may have an origin from any tissue. The cancer may originate from melanoma, colon, breast, or prostate, and thus may be made up of cells that were originally skin, colon, breast, or prostate, respectively. The cancer may also be a hematological malignancy, which may be leukemia or lymphoma. The cancer may invade a tissue such as liver, lung, bladder, or intestinal.

Representative cancers and/or tumors include or are related to a basal cell carcinoma, biliary tract cancer; bladder cancer; bone cancer; brain and central nervous system cancer; breast cancer (including triple-negative breast cancer); cancer of the peritoneum; cervical cancer; choriocarcinoma; colon and rectum cancer; connective tissue cancer; cancer of the digestive system; endometrial cancer; esophageal cancer; eye cancer; cancer of the head and neck (including carcinoma of head and neck); gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; urothelial cancer; uterine or endometrial cancer; cancer of the urinary system; vulval cancer; lymphoma including Hodgkin's and non-Hodgkin's lymphoma, B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; other carcinomas and sarcomas; and post-transplant lymphoproliferative disorder (PTLD), abnormal vascular proliferation associated with phakomatoses, edema (such as that associated with brain tumors), and Meigs' syndrome. In embodiments, the cancer is bladder cancer, carcinoma of head and neck, colon and rectum cancer, kidney or renal cancer, melanoma, non-small cell lung cancer, triple-negative breast cancer, or urothelial cancer.

In embodiments, the cancer is classified as PDL-1+ and/or CTLA4+.

Capsules

The capsule of a therapeutic composition described herein may comprise any suitable material. Those skilled in the art would understand based upon the teachings of this specification that the term capsule is not intended to be limited to the types of capsules described in, for example, the United States Pharmacopeia (USP), although they may comprise such capsules, but refers to any container or layer which encloses and/or encapsulates a material and/or liquid such as the microbial compositions described herein.

In embodiments, the capsule is designed and selected to provide mechanical stability to the therapeutic composition. For example, in embodiments, the capsule maintains a particular shape (e.g., a cylinder with hemispherical ends) such that it encapsulates a microbial composition without leaking from the capsule.

In embodiments, the capsule comprises a polymeric material. Non-limiting examples of suitable polymeric materials include gelatin, polymethylmethacrylate, poly(N,N-dimethylacrylamide), polyoxamer, polyethylene glycol, polypropylene glycol, polysaccharides (e.g., sucrose, trehalose, glucose, starches such as tapioca and arrowroot, chitosan, alginate, guar gum), polyacrylate, polymethacrylate, polyvinyl alcohol, polyalkylene glycols, polyacrylamide, polyvinylpyrrolidone, polyurethane, polylactide, lactide/glycolide copolymer, polycaprolactone, polydioxanones, polyanhydride, polyhydroxybutyrate, polysiloxane, polytrimethylene carbonate, polyalkylene glycol, and combinations and/or copolymers thereof. In embodiments, the capsule comprises gelatin.

In embodiments, the capsule may comprise a bioadherent polymer such as mucin.

In embodiments, the capsule has a particular shape or size. For example, in some cases, the capsule has a shape or size as described in the USP including, but not limited to, #000 capsule, #00 capsule, #0 capsule, #1 capsule, #2 capsule, #3 capsule, #4 capsule, or #5 capsule. Other capsule shapes and/or sizes are also possible.

A capsule includes a reversibly attachable capsule body and a capsule cap. The capsule has an inner surface and an outer surface. In embodiments, the outer surface of the capsule is coated with an exterior coating comprising an enteric polymer. In embodiments, outside the exterior coating comprising the enteric polymer is one or more additional coatings that create at least one compartment for containing a chemotherapeutic agent and/or one or more additional therapeutic agents.

Coatings

In embodiments, the capsule comprises a coating. In certain embodiments, the coating separates the external environment from the capsule, thereby inhibiting dissolution of a capsule and/or promoting stability of the capsule. In embodiments, the capsule comprises two or more coatings which are sequentially applied, e.g., after a first coating has been applied and air dried, a second coating is applied. Unless the context clearly dictates otherwise, as used herein, the term "coating" includes at least one coating, e.g., one, two, three, four, or more coatings. Moreover, a first coating may comprise identical components as an at least second coating or a first coating may comprise different components from an at least second coating. In embodiments, the coating coats the outside of a capsule, i.e., an exterior coating.

In embodiments, the coated capsule does not immediately release the microbial composition upon ingestion; rather, postponement of the release of the microbial composition until the coated capsule is lower in the GI tract; for example, for release in the colon (i.e., large intestine) which includes the cecum, ascending, transverse, descending or sigmoid portions of the colon, and rectum. For example, a coated capsule can be enteric coated to delay substantial release of the microbial composition until it reaches the large intestine.

In embodiments, the capsule is coated with an exterior enteric coating designed such that the microbial composition is not released from the capsule until reaching the subject's ileum or the subject's colon.

In embodiments, the microbial composition is released from a coated capsule by one or both of enzymes secreted by colonic microflora and/or with elevated pH, e.g., at or above about pH 7 or at or above about pH 7.4. In the former, the microbial composition is released by disruption of the coating via an attack on the material susceptible to colonic enzymes; in the latter, the microbial composition is released by disruption of the coating via attack on the pH-sensitive (enteric) polymer.

In embodiments, the coated capsule releases at least 60% of the coated capsule's microbial composition in the large intestine. For example, the coated capsule releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the microbial composition in the large intestine (e.g., one or more of cecum, ascending, transverse, descending or sigmoid portions of the colon, and rectum).

In embodiments, the coated capsule provides substantially complete release of the microbial composition prior to the rectum.

In embodiments, the coated capsule releases the microbial composition at a specific pH. For example, in embodiments, the coated capsule is substantially stable in an acidic environment and substantially unstable (e.g., dissolves rapidly or is physically unstable) in a near neutral to alkaline environment. In embodiments, stability is indicative of not substantially releasing the microbial composition; whereas instability is indicative of substantially releasing the microbial composition. For example, in embodiments, the coated capsule is substantially stable at a pH of about 7.0 or less, or about 6.5 or less, or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. Since this coated capsule is substantially stable at a pH of about 4 to about 5 or lower, the microbial composition is not substantially released in the stomach and/or small intestine (e.g., one or more of the duodenum, jejunum, and ileum). In these embodiments, the coated capsule substantially releases the microbial composition in the large intestine (e.g., one or more of the cecum, ascending colon, transverse colon, descending colon, and sigmoid colon). In embodiments, the pH values recited herein may be adjusted as known in the art to account for the state of the subject, e.g., whether in a fasting or postprandial state.

In embodiments, the coated capsule is unstable in fluid of the colon or in a simulated colonic fluid. These coated capsules release about 70% or more by weight of its microbial composition in fluid of the colon or in a simulated colonic fluid in about 15, or about 30, or about 45, or about 60, or about 90 minutes. In embodiments, the coated capsule is unstable in near neutral to alkaline environments. These coated capsules release about 70% or more by weight of their microbial composition in intestinal fluid with a pH of about 7 or greater (i.e., about pH 7.4), or simulated intestinal fluid with a pH of about 7 or greater (i.e., about pH 7.4), in about 15, or about 30, or about 45, or about 60, or about 90 minutes. A coated capsule that is unstable in near neutral or alkaline environments may release 70% or more by weight of their microbial composition in a fluid having a pH greater than about 7.0 (e.g., a fluid having a pH of from about 7 to about 14, a fluid having a pH of about 7.4, a fluid having a pH of from about 8 to about 14, a fluid having a pH of from about 9 to about 14, a fluid having a pH of from about 10 to about 14, or a fluid having a pH of from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

In embodiments, the coated capsule is stable in gastric fluid or stable in acidic environments. These coated capsules release about 30% or less by weight of their microbial composition in gastric fluid with a pH of about 4 to about 5 or less, or simulated gastric fluid with a pH of about 4 to about 5 or less, in about 15, or about 30, or about 45, or about 60, or about 90 minutes. The coated capsules may release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of its microbial composition in gastric fluid with a pH of 4 to 5, or less or in simulated gastric fluid with a pH of 4 to 5 or less, in about 15, or about 30, or about 45, or about 60, or about 90 minutes. The coated capsules may release about 1%, about 2%, about 3%, about 4%, about 5%, about 6%, about 7%, about 8%, about 9%, or about 10% by weight of its microbial composition in gastric fluid with a pH of 5 or less, or in simulated gastric fluid with a pH of 5 or less, in about 15, or about 30, or about 45, or about 60, or about 90 minutes.

When quantifying or analyzing release of the microbial composition from a capsule (e.g., a coated capsule), simulated gastric fluid, simulated small intestinal fluid, and/or simulated colonic fluid, as disclosed in the 2005 Pharmacopeia 23NF/28USP in Test Solutions at page 2858, may be used. Other simulated fluids known to those of skill in the art, for example, simulated gastric fluid and/or simulated colonic fluid prepared with or without enzymes.

In embodiments, the coating includes an enteric agent (e.g., an enteric polymer) that is substantially stable in acidic environments and substantially unstable in about neutral environments to alkaline environments. In embodiments, the coating contains an enteric agent that is substantially stable in gastric fluid or in a simulation thereof. The enteric agent can be selected from, for example, solutions or dispersions of methacrylic acid copolymers, cellulose acetate phthalate (CAP), hydroxypropylmethyl cellulose phthalate, polyvinyl acetate phthalate, carboxymethylethylcellulose, and EUDRAGIT®-type polymer (poly(methacrylic acid, methylmethacrylate), hydroxypropyl methylcellulose acetate succinate, cellulose acetate trimellitate, hypromellose (INN) hydroxypropyl methylcellulose (HPMC), shellac or other suitable enteric coating polymers. Similar polymers include Kollicoat® MAE 30 DP and Kollicoat® MAE 100 P. In embodiments, the enteric agent may be a combination of the foregoing solutions or dispersions.

In embodiments, the enteric polymer is a co-polymer of a (meth)acrylic acid and a (meth)acrylic acid $C_{1-4}$ alkyl ester, for instance, a copolymer of methacrylic acid and methacrylic acid methyl ester. Such a polymer is known as a poly(methacrylic acid/methyl methacrylate) co-polymer. Examples of such co-polymers are usually anionic. Examples of anionic poly(methacrylic acid/methyl methacrylate) co-polymers include Eudragit® L, Eudragit® S, and Eudragit® FS.

In embodiments, the enteric agent comprises a copolymer of methacrylic acid and ethyl acrylate.

In embodiments, the enteric agent comprises any EUDRAGIT®-type polymer, derivatives thereof, and copolymers thereof. EUDRAGIT® polymers are available from Evonik Industries AG (Essen, Germany).

In embodiments, the coating comprises a material that dissolves and/or degrades at a particular pH after a given amount of time (e.g., after at least an hour of exposure to the particular pH). In embodiments, the coating is designed to at least partially degrade and/or at least partially dissolve in the colon of the subject; thus, the coating comprises an enteric polymer that at least partially dissolves and/or at least partially degrades at a pH of greater than or equal to 7.0, i.e., pH 7.4 (e.g., EUDRAGIT® S 100, EUDRAGIT® S 12, 5, EUDRAGIT® FS 30D, Phloral®); see, e.g., U.S. Pat. No. 9,023,368, US 20150150837, and US 20150202162.

In embodiments, the enteric polymer is selected such that it exhibits time controlled degradation and/or dissolution, independent of pH. Non-limiting examples of such enteric polymers include EUDRAGIT® RL 30D, EUDRAGIT® RL P0, EUDRAGIT® RL 100, EUDRAGIT® RL 12, 5, EUDRAGIT® RS 30D, EUDRAGIT® RS P0, EUDRAGIT® RS 100, EUDRAGIT® RS 12, 5, EUDRAGIT® NE 30D, EUDRAGIT® NE 40D, and EUDRAGIT® NM 30D.

In certain embodiments, the coating comprises a copolymer of two or more enteric polymers, as described herein.

In embodiments, the coating comprises an enteric elastomer. In embodiments, the enteric elastomer comprises a mixture of two or more polymers with carboxyl functionality such that the two or more polymers form hydrogen bonds with one another and has both enteric and elastic properties. In certain embodiments, the enteric elastomer comprises a first polymer comprising a structure as in Formula (I):

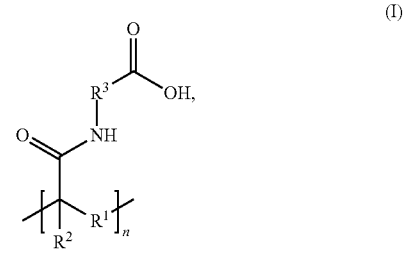

or a pharmaceutically acceptable salt thereof, wherein each $R^1$ is the same or different and is selected from optionally substituted alkylene, optionally substituted heteroalkylene, optionally substituted arylene, and optionally substituted heteroarylene, each $R^2$ is the same or different and is selected from hydrogen, optionally substituted alkyl, and optionally substituted heteroalkyl, each $R^3$ is the same or different and is selected from optionally substituted alkylene and optionally substituted heteroalkylene, n is an integer between 25 and 250,000, and a second polymer comprising a structure as in Formula (II) hydrogen bonded to the first polymer:

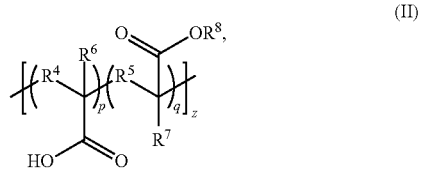

(II)

or a pharmaceutically acceptable salt thereof, wherein each $R^4$ is the same or different and is selected from optionally substituted alkylene and optionally substituted heteroalkylene, each $R^5$ is the same or different and is selected from optionally substituted alkylene and optionally substituted heteroalkylene, each $R^6$ is the same or different and is selected from hydrogen, optionally substituted alkyl, and optionally substituted heteroalkyl, each $R^7$ is the same or different and is selected from hydrogen, optionally substituted alkyl, and optionally substituted heteroalkyl, each R8 is the same or different and is optionally substituted alkyl, p is an integer between 1 and 10, q is an integer between 1 and 10, and z is an integer between 1 and 150,000, provided that (p+q)*z is greater than or equal to 20. Suitable enteric elastomers and methods for making such enteric elastomers are described in more detail in International Patent Publication No. WO 2015191922, which is incorporated herein by reference in its entirety.

In embodiments, the coating comprises a polymer formed by the reaction of one or more monomers in the presence of a food grade catalyst (e.g., caffeine). Suitable polymers formed in the presence of food grade catalysts are described in more detail in International Patent Publication No. WO 2015/168297, which is incorporated herein by reference in its entirety.

In embodiments, the coating may degrade as a function of time when in aqueous solution without regard to the pH and/or the presence of enzymes in the solution. Such a coating may comprise a water insoluble polymer. Its solubility in aqueous solution is therefore independent of the pH. The term "pH independent" as used herein means that the water permeability of the polymer and its ability to release microbial compositions is not a function of pH and/or is only very slightly dependent on pH. Suitable water insoluble polymers include pharmaceutically acceptable non-toxic polymers that are substantially insoluble in aqueous media, e.g., water, independent of the pH of the medium. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose. Other examples of insoluble polymers include, but are not limited to, lacquer, and acrylic and/or methacrylic ester polymers, polymers or copolymers of acrylate or methacrylate having a low quaternary ammonium content, or mixture thereof. Other examples of insoluble polymers include EUDRAGIT RS®, EUDRAGIT RL®, and EUDRAGIT NE®. Insoluble polymers that may be useful include polyvinyl esters, polyvinyl acetals, polyacrylic acid esters, butadiene styrene copolymers. In embodiments, colonic release is achieved by use of a slowly-eroding wax plug (e.g., various PEGS, including for example, PEG6000).

In embodiments, the coating may comprise a material susceptible to colonic enzymes. Here, the material is degraded by gut flora via an enzyme that is secreted by colonic bacteria. In embodiments, the coating may be degraded by bacteria present in the large intestine. Such a coating may comprise a mixture of a material susceptible to colonic enzymes (i.e., which is susceptible to attack by colonic bacteria) and an enteric polymer which has a solubility threshold at about pH 7 or greater (illustrative enteric polymers are discussed above).

The material susceptible to colonic enzyme may comprise a polymeric carbohydrate selected from amylopectin, amylose, carrageenan, chitin, chitosan, chondroitin sulphate, curdlan, cyclodextrin, dextran, levan, pullulan, scleroglucan, and starch, or a combination thereof.

In embodiments, the polymeric carbohydrate is starch, amylose, and/or amylopectin.

In embodiments, the starch may have from about 20 wt % to about 30 wt % amylose with the remainder being at least substantially made up of amylopectin. In embodiments, the starch may have at least 0.1 wt %, e.g., at least 10% or 16% and at least 35 wt %, amylose. In embodiments, the starch may have at least 50 wt % amylose. Particularly suitable starches have from about 65 wt % to about 75 wt %, e.g., about 70 wt % amylose.

In embodiments, the starch may have up to 100% amylopectin, e.g., from about 0.1 wt % to about 99.9 wt % amylopectin. In embodiments, the starch may have no more than 50 wt % amylose and at least 50 wt % amylopectin, e.g., up to 75 wt % amylopectin and even as much as up to 99 wt % amylopectin, are suitable. The starch may be, for instance, unmodified waxy corn starch. This and other similar starches comprise about 100% amylopectin. In embodiments, the starch may have no more than 50 wt % amylopectin. Particularly suitable starches have from about 25 wt % to about 35 wt % amylopectin, e.g., about 30 wt % amylopectin.

In embodiments, in a coating, a ratio of the material susceptible to colonic enzymes to the enteric polymer is from about 15:85 to about 99:1.

In embodiments, other colon-specific delivery approaches may be used. For example, a coated capsule may be formulated using a colon-specific drug delivery system (CODES) as described for example, in Li et al., AAPS PharmSciTech (2002), 3(4): 1-9, the entire contents of which are incorporated herein by reference.

In embodiments, the coating of the pharmaceutical may further comprise a plasticizer. In embodiments, the plasticizer is triethyl citrate. The coating may comprise between about 1 and 20% triethyl citrate, e.g., between about 5 and 15% triethyl citrate. Particularly suitable coatings comprise about 12% triethyl citrate.

In embodiments, the coating of the pharmaceutical may further comprise a coating additive. The coating additive may be talc. The coating additive may be an "additive composition", for example, comprising mono and/or diglycerides of glycerol monostearate and triethyl citrate. An example of the additive composition is PlasACRYL™. For example, one or more PlasACRYL™ additives may be used as an anti-tacking agent coating additive. Illustrative PlasACRYL™ additives include, but are not limited, to PlasACRYL™ HTP20 and PlasACRYL™ T20. The coating may comprise between about 1 and 15% the additive composition, e.g., between about 5 and 10% the additive composition. Particularly suitable coatings comprise about 8% the additive composition.

In certain embodiments, the coating may comprise a bioadherent polymer such as mucin.

In embodiments, the coating may comprise about 56% EUDRAGIT® S100 (poly(methacrylic acid, methylmethacrylate), about 24% starch, about 12% triethyl citrate, and about 8% an additive composition comprising mono and/or di-glycerides of glycerol monostearate and triethyl citrate, e.g., PlasACRYL™ T20.

In embodiments, a capsule has an interior coating which comprises components as described above. Thus, the coating may both an interior and exterior enteric coating. A capsule may have only an exterior enteric coating. Alternately, a capsule may have only an interior enteric coating.

In embodiments, a capsule comprises an interior coating which has hydrophobic properties which prevents or retards the contact of an aqueous phase (e.g., a microbial composition of the present disclosure) with the capsule (or capsule material).

In embodiments, the interior coating comprises a hydrophobic coating. The hydrophobic coating may comprise a material selected from shellac, zein, polysaccharides, silk, polycaprolactone, oil, pectin, wax, polymers, shellac, and derivatives thereof, and combinations thereof. Non-limiting examples of suitable polysaccharides include alginate, hyaluronic acid, and chitosan. Non-limiting examples of suitable oils include avocado oil, vegetable oil, castor oil, olive oil, jojoba oil, cocoa butter, coconut oil. Non-limiting examples of suitable waxes include beeswax, carnauba wax, and paraffin wax. In embodiments, the hydrophobic coating is shellac. Thus, a capsule may have an exterior enteric coating and an internal hydrophobic coating.

In embodiments, coated capsules include features as described in one or more of U.S. Pat. Nos. 4,196,564; 4,196,565; 4,247,006; 4,250,997; 4,268,265; 5,317,849; 6,572,892; 7,712,634; 8,074,835; 8,398,912; 8,440,224; 8,535,713; 8,557,294; 8,646,591; 8,739,812; 8,810,259; 8,852,631; 8,911,777; and 8,911,788; US Patent Publication Nos. 2006/001896; 2007/0292523; 2008/0020018; 2008/0113031; 2010/0203120; 2010/0255087; 2010/0297221; 2011/0052645; 2012/0141531; 2012/0141585; 2013/0184290; 2013/0243873; 2013/0287842; 2013/0295188; 2013/0307962; 2013/0330411; 2014/0017313; 2014/0088202; 2014/0227357; 2014/0234418; and 2014/0302132; and International Patent Publication No. WO 2008/135090. The contents of the aforementioned patents and patent applications are hereby incorporated by reference in their entirety.

In embodiments, a chemotherapeutic agent that can be formulated for oral administration and/or one or more additional therapeutic agents may be combined with a microbial composition and encapsulated by the capsule.

In embodiments, the capsule (which encapsulates a microbial composition) is coated with a first exterior coating comprising an enteric polymer and outside the first exterior coating are one or more additional coatings that comprise a chemotherapeutic agent that can be formulated for oral administration and/or one or more additional therapeutic agents. Here, the chemotherapeutic agent and/or one or more additional therapeutic agents were combined with a binder and spray coated onto the first enteric-coated capsule which encapsulates a microbial composition. Such a coated capsule may have received a second enteric coating (exterior to the chemotherapeutic agent and/or additional therapeutic agent(s)) which allows release of the chemotherapeutic agent and/or additional therapeutic agent(s) in a region of the digestive system before the colon. Alternately, the chemotherapeutic agent and/or one or more additional therapeutic agents were combined with a second enteric polymer and a binder and spray coated onto the first enteric-coated capsule which encapsulates a microbial composition; here, the second enteric polymer allows release of the chemotherapeutic agent and/or additional therapeutic agent(s) in a region of the digestive system before the colon.

In embodiments, a therapeutic composition can be in the form of a capsule, tablet, or pill. In embodiments, the capsule, tablet, or pill can be coated or otherwise compounded to provide a dosage form affording the advantage of prolonged action. For example, the capsule, tablet, or pill can comprise an inner dosage (e.g., a microbial composition) and an outer dosage component (e.g., a chemotherapeutic agent and/or additional therapeutic agent), the latter being in the form of an envelope over the former. The two components can be separated by an enteric layer which serves to resist disintegration in the stomach and permits the inner component to pass into the duodenum or colon and/or to be delayed in release. A variety of materials can be used for such enteric layers or coatings (as described herein). Illustrative materials include a number of polymeric acids and mixtures of polymeric acids with such materials as shellac, cetyl alcohol, and cellulose acetate.

Methods of Manufacturing

The therapeutic compositions described herein may be manufactured using any suitable method. Generally, a capsule is filled with a microbial composition and then closed/sealed such that the microbial composition is encapsulated by the capsule.

In embodiments, manufacturing a therapeutic composition may comprise steps of: (1) coating the exterior of a dissociated capsule (i.e., comprising separate capsule body and capsule cap) with the exterior enteric coating, (2) filling the capsule body with a microbial composition, and (3) closing the capsule cap over the capsule body, thereby encapsulating the microbial composition in the exterior, enteric-coated capsule.

Optionally, manufacturing a therapeutic composition may comprise steps of: (1) coating the exterior of a dissociated capsule (i.e., comprising separate capsule body and capsule cap) with the exterior enteric coating, (2) coating the interior of the dissociated capsule with an interior coating, (3) filling the capsule body with a microbial composition, and (4) closing the capsule cap over the capsule body, thereby encapsulating the microbial composition in the dual-coated capsule.

Alternately, manufacturing a therapeutic composition may comprise steps of: (1) coating the interior of the dissociated capsule (i.e., comprising separate capsule body and capsule cap) with an interior coating, (2) coating the exterior of a dissociated capsule with the exterior enteric coating, (3) filling the capsule body with a microbial composition, and (4) closing the capsule cap over the capsule body, thereby encapsulating the microbial composition in the dual-coated capsule.

In embodiments, a chemotherapeutic agent that can be formulated for oral administration and/or one or more additional therapeutic agents may be combined with a microbial composition and encapsulated by the capsule.

In embodiments, the bodies and caps of gelatin capsules (e.g., size #00) are separated. An exterior enteric coating suspension is prepared by dispersing one or more enteric coating polymers along with other components in a solution. The exterior enteric coating suspension is applied to the exterior of separated capsule bodies and caps, e.g., using a fluid bed Wurster column coater, Fluid Bed Coater, or an equivalent). The capsules are fluidized in the product bowl and the exterior enteric coating suspension is sprayed to produce the outer coating to a target of between about 2 mg/cm$^2$ and 6 mg/cm$^2$, e.g., 3 mg/cm$^2$. After completion of this step, the capsules are set to dry, e.g., between about 8 hours and 24 hours. After drying, illustrative capsules are weighed to calculate weight gain from the exterior enteric coating. Capsules may be inspected for irregularities.

In an embodiment, EUDRAGIT® S100 (poly(methacrylic acid, methylmethacrylate)), starch, triethyl citrate, and PlasACRYL™ T20 are dissolved in a solution of water, ethanol, and n-butanol, mixed, and then charged to a suitable spraying device. The solution is then spray coated on the outer surface of the capsule bodies and capsule caps to a target weight gain. The capsule bodies and capsule caps are allowed to dry for about 8 hours to about 24 hours, or longer, e.g., for a week, a month, or more, before further procession, e.g., filling with a microbial composition.

In embodiments, it may be desirable to provide an amount of the microbial composition to a capsule's cap in addition to providing the microbial composition to the capsule's body. In this embodiment, more microbial composition will be included in a capsule and/or less air will be contained in a closed capsule.

In embodiments, the interior surface of a capsule is provided an internal coating.

In embodiments, the capsule is coated with a first exterior coating comprising an enteric polymer and outside the first exterior coating is applied one or more additional coatings that comprise a chemotherapeutic agent that can be formulated for oral administration and/or one or more additional therapeutic agents. Here, the chemotherapeutic agent and/or one or more additional therapeutic agents are combined with a binder and spray coated onto the first enteric-coated capsule encapsulating a microbial composition. Such a therapeutic composition may receive a second enteric coating (exterior to the chemotherapeutic agent and/or additional therapeutic agent(s)) which allows release of the chemotherapeutic agent and/or additional therapeutic agent(s) in a region of the digestive system before the colon. Alternately, the chemotherapeutic agent and/or one or more additional therapeutic agents are combined with a second enteric polymer and a binder and spray coated onto the first enteric-coated capsule encapsulating a microbial composition; here, the second enteric polymer allows release of the chemotherapeutic agent and/or additional therapeutic agent(s) in a region of the digestive system before the colon.

In embodiments, a therapeutic composition can be prepared in capsule, tablet, or pill form. In embodiments, the capsule, tablet, or pill is coated or otherwise compounded to provide a dosage form affording the advantage of prolonged action. For example, the capsule, tablet, or pill is prepared with an inner dosage (e.g., a microbial composition) and with an outer dosage component (e.g., a chemotherapeutic agent and/or additional therapeutic agent), the latter being in the form of an envelope over the former. The two components can be prepared by adding an enteric layer which separates the components; the enteric layer serves to resist disintegration in the stomach and permits the inner component to pass into the duodenum or colon and/or to be delayed in release. A variety of materials can be used for such enteric layers or coatings (as described herein). Illustrative materials include a number of polymeric acids and mixtures of polymeric acids with such materials as shellac, cetyl alcohol, and cellulose acetate.

In embodiments, a therapeutic composition can be incorporated into tablets, drenches, boluses, capsules or premixes. Formulation of these active ingredients into such dosage forms can be accomplished by means of methods well known in the pharmaceutical formulation arts. See, e.g., U.S. Pat. No. 4,394,377. Filling gelatin capsules with any desired form of the active ingredients readily produces capsules. If desired, these materials can be diluted with an inert powdered diluent, such as sugar, starch, powdered milk, purified crystalline cellulose, or the like to increase the volume for convenience of filling capsules.

In embodiments, conventional formulation processes can be used to prepare tablets containing a therapeutic composition. In addition to the active ingredients, tablets may contain a base, a disintegrator, an absorbent, a binder, and a lubricant. Typical bases include lactose, sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents include starch and lactose. Magnesium carbonate is also useful for oily substances. As a binder there can be used, for example, gelatin, gums, starch, dextrin, polyvinyl pyrrolidone and various cellulose derivatives. Among the commonly used lubricants are magnesium stearate, talc, paraffin wax, various metallic soaps, and polyethylene glycol.

In embodiments, for preparing solid compositions such as tablets, an active ingredient is mixed with a pharmaceutical carrier, e.g., conventional tableting ingredients such as corn starch, lactose, sucrose, sorbitol, talc, stearic acid, magnesium stearate, dicalcium phosphate or gums, or other pharmaceutical diluents, e.g. water, to form a solid preformulation composition containing a homogeneous mixture of a composition described herein. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing a desired amount of an active ingredient (e.g., at least about $10^5$, $10^6$, $10^7$, $10^8$, $10^9$, $10^{10}$, $10^{11}$, $10^{12}$, or $10^{13}$ cfu). A therapeutic composition used herein can be flavored.

In embodiments, a therapeutic composition can be a tablet or a pill. In embodiments, a tablet or a pill can be coated or otherwise compounded to provide a dosage form affording the advantage of prolonged action. For example, a tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Any of the above-described inner coatings; capsules, tablets, or pills; and outer coatings may be combined into a therapeutic composition described herein. A skilled artisan would know how to select an inner coating; a capsule tablet, or pill format; and an outer coating according to his/her present need, which would be based on the specific microbial composition and/or the location in a subject (i.e., in the colon) where the microbial composition should be released.

Additional teachings relevant to the present disclosure are disclosed in WO 2007122374, which is incorporated herein by reference in its entirety.

In embodiments, a therapeutic composition can be a drench. In embodiments, a drench is prepared by choosing a saline-suspended form of a therapeutic composition. A water-soluble form of one ingredient can be used in conjunction with a water-insoluble form of the other by preparing a suspension of one with an aqueous solution of the other. Water-insoluble forms of either active ingredient may be prepared as a suspension or in some physiologically acceptable solvent such as polyethylene glycol. Suspensions of water-insoluble forms of either active ingredient can be prepared in oils such as peanut, corn, sesame oil or the like; in a glycol such as propylene glycol or a polyethylene glycol; or in water depending on the solubility of a particular active ingredient. Suitable physiologically acceptable adjuvants may be necessary in order to keep the active ingredients suspended. Adjuvants can include and be chosen from among the thickeners, such as carboxymethylcellulose, polyvinyl pyrrolidone, gelatin and the alginates. Surfactants generally will serve to suspend the active ingredients, particularly the fat-soluble propionate-enhancing compounds. Most useful for making suspensions in liquid nonsolvents are alkylphenol polyethylene oxide adducts, naphthalene-sulfonates, alkylbenzene-sulfonates, and the polyoxyethylene sorbitan esters. In addition, many substances, which affect the hydrophilicity, density and surface tension of the liquid, can assist in making suspensions in individual cases. For example, silicone anti-foams, glycols, sorbitol, and sugars can be useful suspending agents.

In embodiments, during the manufacture of a therapeutic composition, a pharmaceutically-acceptable aqueous solution, binder, disintegrant, filler, and/or preservative may be mixed into the microbial composition to promoted desirable properties in the therapeutic composition. In embodiments, during the manufacture of a therapeutic composition comprising a chemotherapeutic agent (with or without the microbial composition), a pharmaceutically-acceptable aqueous solution, binder, disintegrant, filler, and/or preservative may be mixed with the chemotherapeutic agent (with or without the microbial composition) to promoted desirable properties in the therapeutic composition.

Illustrative binders include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Illustrative fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be added to a microbial composition to promote its disintegration when exposed to an aqueous environment. Illustrative disintegrants include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Definitions

As used herein, "isolated" or "purified" refers to a bacterium or other entity or substance that has been (1) separated from at least some of the components with which it was associated when initially produced (whether in nature or in an experimental setting), and/or (2) produced, prepared, purified, and/or manufactured by the hand of man. Isolated or purified bacteria can be separated from at least about 10%, about 20%, about 30%, about 40%, about 50%, about 60%, about 70%, about 80%, about 90%, or more of the other components with which they were initially associated.

As used herein, "eukaryotic" refers to belonging to a cell that contains a nucleus and membrane-bound organelles.

As used herein, "bacteria," "bacterium," and "archaea" refer to single-celled prokaryotes that lack membrane bound nuclei and lack organelles.

As used herein, "colony forming units" (cfu) refers to an estimate of the number of viable microorganism cells in a given sample.

As used herein, "viable" means possessing the ability to multiply.

As used herein, "fecal bacteria" refers to bacteria that can be found in fecal matter.

As used herein, "cytotoxic" activity or bacterium includes the ability to kill a bacterial cell, such as a pathogenic bacterial cell. A "cytostatic" activity or bacterium includes the ability to inhibit, partially or fully, growth, metabolism, and/or proliferation of a bacterial cell, such as a pathogenic bacterial cell.

As used herein, the terms "pathogen" and "pathogenic" in reference to a bacterium or any other organism or entity includes any such organism or entity that is capable of causing or affecting a disease, disorder or condition of a host organism containing the organism or entity.

As used herein, "spore" or a population of "spores" includes bacteria (or other single-celled organisms) that are generally viable, more resistant to environmental influences such as heat and bacteriocidal agents than vegetative forms of the same bacteria, and typically capable of germination and out-growth. "Spore-formers" or bacteria "capable of forming spores" are those bacteria containing the genes and other necessary abilities to produce spores under suitable environmental conditions.

As used herein, a "combination" of two or more bacteria includes the physical co-existence of the two bacteria, either in the same material or product or in physically connected products, as well as the temporal co-administration or co-localization of the two bacteria.

As used herein, "microbiota," and "flora" refer to a community of microbes that live in or on a subject's body, both sustainably and transiently, including eukaryotes, archaea, bacteria, and viruses (including bacterial viruses (i.e., phage)). A "fecal microbiota" refers to a microbiota that lives in or is derived from a stool or fecal material of a subject. A "non-selected" or "substantially complete" fecal microbiota refers to a community or mixture of fecal microbes derived from a donor's fecal sample without selection and substantially resembling microbial constituents (e.g., bacterial constituents) and population structure found in such fecal sample.

As used herein, "Shannon Diversity Index" refers to a diversity index that accounts for abundance and evenness of species present in a given community using the formula $$H = -\sum_{i=1}^{R} p_i \ln p_i$$

where H is Shannon Diversity Index, R is the total number of species in the community, and $p_i$ is the proportion of R made up of the ith species. Higher values indicate diverse and equally distributed communities, and a value of 0 indicates only one species is present in a given community. For further reference, see Shannon and Weaver, (1949) *The mathematical theory of communication*. The University of Illinois Press, Urbana. 117 pp.

As used herein, "gut dysbiosis" refers to an imbalance, maladaptation, and/or reduced diversity in the microbiota in a subject's digestive system. For example, a part of the gut flora is unbalanced, with normally dominating species, i.e., beneficial bacteria, becoming underrepresented (and/or less metabolically active) and outcompeted by contained species, e.g., pathogenic and/or antibiotic-resistant bacteria, which proliferate to fill the void.

As used herein, a "sterile fecal filtrate" or a "non-cellular fecal filtrate" refers to a liquid component of a fecal material, where the liquid component is free or substantially free of cell-based living organisms (e.g., bacteria, fungi, or their spores), but retains bacteriophages and non-cellular biological materials. Preferably, a non-cellular or sterile fecal filtrate is also free of viruses for eukaryotic host cells.

As used herein, "antibiotic" refers to a substance that is used to treat and/or prevent bacterial infection by killing bacteria, inhibiting the growth of bacteria, or reducing the viability of bacteria.

As used herein, an "intermittent dosing schedule" means that that a therapeutic composition is administered for a period of time followed by a period of time (a treatment period) where treatment with such therapeutic composition is withheld (a rest period). Intermittent dosing regimens can be expressed as treatment period in days or weeks/rest period in days or weeks. For example, a 4/1 intermittent dosing schedule refers to an intermittent dosing schedule where the treatment period is four weeks/days and the rest period is one week/day.

As used herein, a "continuous dosing schedule" refers to a dosing schedule where a therapeutic composition is administered during a treatment period without a rest period. Throughout the treatment period of a continuous dosing schedule, a therapeutic composition can be administered, for example, daily, or every other day, or every third day. On a day when a therapeutic composition is administered, it can be administered in a single dose, or in multiple doses throughout the day.

As used herein, "dosing frequency" refers to the frequency of administering doses of a therapeutic composition in a given time. Dosing frequency can be indicated as the number of doses per a given time, for example, once per day, once a week, or once in two weeks.

As used herein, "dosing interval" refers to the amount of time that elapses between multiple doses being administered to a subject.

As used herein, examples of an OTIC induced by an anti-cancer therapy include abdominal pain, anemia and low blood counts, appetite loss, autoimmune effects, bleeding and bruising (thrombocytopenia), cancer, changes in mood or thinking, constipation, cough, dehydration, delirium, diabetes-related symptoms, diarrhea, dry mouth or xerostomia, eating problems, edema, falling, fatigue, fertility issues, fever, flu-like symptoms, fluid in the abdomen or ascites, gastrointestinal (GI) mucositis, hair loss (alopecia), hand-foot syndrome or palmar-plantar erythrodysesthesia, headache, hearing problems, high or low blood pressure, hormone changes, hiccups, hypercalcemia, infection and neutropenia, inflammatory bowel disease (IBD), irritable bowel syndrome (IBS), leg cramps, lymphedema, memory or concentration problems, mouth and throat problems, nausea and vomiting, nerve problems (peripheral neuropathy), obesity, osteoporosis, ostomies, pain, seizures, sexual health issues, shortness of breath, sinus congestion, skin and nail changes, sleep problems, stool or urine changes, sweating, swelling, ulcerative colitis, urinary and bladder problems, weight gain from retaining fluid, and/or weakness. In embodiments, an OTIC of the anti-cancer therapeutic agent and/or anti-cancer therapy is caused by gut dysbiosis; it has been reported that chemotherapy, for example, is associated with reduced diversity in the gut microbiome. Thus, "treating, preventing, or reducing an OTIC" refers to decreasing the severity of an OTIC and up to eliminating the OTIC, e.g., in part, by repairing/repopulating his/her gut microbiome after receiving the anti-cancer therapeutic agent and/or anti-cancer therapy.

As used herein, "therapeutically effective amount/dose" refers to an amount of a composition which is effective in treating the named disease, disorder or condition, or preventing, or reducing an OTIC induced by an anti-cancer therapy, as the case may be.

As used herein, "increase[ing] efficacy of an anti-cancer therapy" refers to the ability of a microbial composition or method using same to promote the beneficial and desired effects of an anti-cancer therapeutic agent and/or anti-cancer therapy, i.e., killing cancer cells, reducing tumor size, and/or simulating an immune response against a cancer cell or tumor.

As used herein, the term "subject," refers to an individual organism such as a human or an animal. In embodiments, the subject is a mammal (e.g., a human, a non-human primate, or a non-human mammal), a vertebrate, a laboratory animal, a domesticated animal, an agricultural animal, or a companion animal. In embodiments, the subject is a human (e.g., a human patient). In embodiments, the subject is a rodent, a mouse, a rat, a hamster, a rabbit, a dog, a cat, a cow, a goat, a sheep, a turkey, a chicken, or a pig.

In embodiments, the subject, e.g., a human, is refractory and/or non-responsive to a treatment directed to a checkpoint molecule. In embodiments, the treatment directed to a checkpoint molecule comprises administration of KEYTRUDA (Pembrolizumab), OPDIVO (Nivolumab), or YERVOY (Ipilimumab).

As used herein, the term "treating" refers to (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment" refers to both therapeutic treatment and prophylactic or preventative measures.

As used herein, the term "substantially", when used to modify a quality, generally allows certain degree of variation without that quality being lost. For example, in certain aspects such degree of variation can be less than 0.1%, about 0.1%, about 0.2%, about 0.3%, about 0.4%, about 0.5%, about 0.6%, about 0.7%, about 0.8%, about 0.9%, about 1%, between 1-2%, between 2-3%, between 3-4%, between 4-5%, or greater than 5%.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The terms "about" and "approximately" as used herein when referring to a measurable value such as a percentage, density, volume and the like, is meant to encompass variations of 20%, 10%, 5%, 1%, 0.5%, or even 0.1% of the specified amount.

A stated range is understood to be any value between and at the limits of the stated range. As examples, a range between 1 and 5 includes 1, 2, 3, 4, and 5; a range between 1 and 10 includes 1, 2, 3, 4, 5, 6, 7, 8, 9, and 10; and a range between 1 and 100 includes 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100.

Unless defined otherwise, all technical and scientific terms used herein have the same meaning as commonly understood by one of ordinary skill in the art to which the present disclosure pertains. Although other probes, compositions, methods, and kits similar, or equivalent, to those described herein can be used in the practice of the present subject matter, the preferred materials and methods are described herein. It is to be understood that the terminology used herein is for the purpose of describing particular embodiments only, and is not intended to be limiting.

Any aspect or embodiment described herein can be combined with any other aspect or embodiment as disclosed herein.

EXAMPLES

Example 1: Use of Fecal Microbiota Transplantation (FMT) to Treat a 25-Year Old Male with Metastatic Melanoma Who was not Responsive to Immunotherapy In this example, a human patient with metastatic melanoma was administered fecal microbiota transplantation (FMT) as an adjunct to pembrolizumab.

The patient was a 25-year-old male who was initially diagnosed with malignant melanoma on an excisional biopsy of an anal lesion. At that time the lesion was 3.75 mm with ulcerations suggestive of melanoma with evidence of superficial spread and suspicion of lymphovascular invasion. Biopsy slides were analyzed and malignant melanoma was confirmed (mucosal lentiginous/pagetoid pattern, BRAF mutant, tumorigenic and mitogenic, Breslow thickness 3.7 mm, Clark's Level IV) with probable lymphatic invasion and possible vascular invasion.

Since the patient had Stage 4 melanoma, it was understood at the outset that his cancer had spread to other parts of the body, including his inguinal lymph nodes, liver, and brain. As such, the patient's long-term prognosis was poor and his likelihood of remission was extremely low.

The patient was treated with Pembrolizumab, a PD-1 checkpoint inhibitor immunotherapy, for 3 cycles. This was stopped early due to progressive disease, pneumonitis, and possible colitis (which resolved on PD-1 immunotherapy discontinuation). Subsequently, he was treated with dabrafenib/trametinib. By this time, the patient had progressive disease with metastatic spread to inguinal lymph nodes, liver, and brain based on advanced imaging. Specifically, he had several liver lesions concerning for malignancy on CT scans, with the largest being 1.8 cm as well as a 1.8 cm right middle cranial fossa lesion and a 3 mm right parietal lobe lesion seen on a brain MRI. He underwent gamma knife treatment.

The patient was administered pembrolizumab along with FMT as an adjunct to potentially improve the patient's prognosis, and inhibit the emergence of OTICs such as colitis.

One day prior to administration of the initial FMT procedure, the patient completed a bowel prep with standard of care PEG-based preparation. The patient was given nil by mouth (NPO) on the morning of the initial FMT administration and on the mornings of all subsequent FMT administrations (minimum of 2 hours before FMT). To ensure that antibiotics do not impact the newly transferred microbiota, all antibacterial drugs, including TMP-SMZ used for Pneumocystis jiroveci Pneumonia (PJP) prophylaxis, was discontinued no later than 48 hours prior to FMT. Post-FMT antibiotic use was considered allowable, if necessary, however, avoiding the use of antibacterial drugs for at least the following 72 hours (ideally for 7 days) post-FMT was expected to increase the likelihood of successful engraftment. Antivirals, were discontinued for 24 hours prior to the FMT procedure and for 7 days post-FMT. Antifungal prophylaxis was permitted, if clinically required.

Three FMT formulations (obtained from OpenBiome, Somerville, Mass.) were used to treat the patient: (1) 250 ml of a liquid fecal microbiota preparation derived from stool of a healthy donor, delivered to the patient via colonoscopy; (2) 30 ml of a liquid fecal microbiota preparation derived from stool of a healthy donor, delivered to the patient via endoscopy (post-pylorus); and (3) double encapsulated (DE) capsules containing a lyophilized fecal microbiota preparation derived from stool of a healthy donor.

A single dose of the 250 ml liquid fecal microbiota preparation was administered to the patient by colonoscopy, and two doses of the 30 ml liquid fecal microbiota preparation were administered by upper endoscopy (post-pylorus) during the same endoscopic session. Over the next 7 weeks, maintenance doses of DE capsules were administered to the patient at a dose of 30 capsules per week. The maintenance doses were administered concurrently with pembrolizumab immunotherapy.

It was not clear whether the mechanism underlying CI immunotherapy enhancement originates from microbial-host-immune interactions within the small intestine or large bowel. Accordingly, in this patient, administration of FMT via upper gastrointestinal delivery (endoscopy) and lower gastrointestinal delivery (colonoscopy) was expected to offer the greatest opportunity for success. This dual method of delivery was expected to maximize donor microbe engraftment into the recipient. For other patients, e.g., whose disease has not progressed as severely as the preset patient, it is expected that administration with capsules alone may be sufficient to increase efficacy of an anti-cancer therapy and/or reduce or treat an OTIC.

For the initial colonoscopic administration, the aim was to infuse the material into the terminal ileum or, if not possible for technical or anatomical reasons, the material was to be delivered to the most proximal aspect of the colon. Similarly, for the administration of the two doses delivered via endoscopy (60 mL, slowly infused by the endoscopist), the aim was to instill the material in the most distal aspect of the duodenum (post-pylorus) by upper endoscope to minimize aspiration risk. A standard normal saline flush was used to ensure the material passed through the endoscopes.

Without wishing to be bound by theory, it is believed that the Peyer's patches in the ileum may be important for achieving a therapeutic benefit of the FMT, since the Peyer's patches are a key driver of the immune system and intestinal bacteria-immunomodulatory complex. Accordingly, it was an aim to target the terminal ileum during the colonoscopy. It was also an aim to infuse two (as opposed to a single) doses to ensure maximum viable bacteria to act distally at the ileum (last part of small bowel). Prior FMT data suggests that up to 500 mL of post-pylorus delivery is safe; thus, it was expected that infusing two doses of 30 ml post-pylorus was feasible.

Subsequent to the endoscopic and colonoscopic FMT administrations, the patient was administered a dose of 30 DE capsules weekly for a total of 12 weeks starting 7 days (+/−2 days) after the initial endoscopic/colonoscopic FMT. Other patients, who would be treated with DE capsules alone, may be administered an equal or a greater dose of DE capsules. Alternately, a patient may be provided a 12-week course to align with standard CI immunotherapy dosing of every 3 weeks for 4 doses. As mentioned above, the ileum may be the most important site for FMT treatment; thus, capsules, which result in upper GI delivery, may be more effective than frequent nasogastric FMT administrations and without the discomfort and challenges associated with endoscopic administrations.

The patient was doing reasonably well at the time of his seventh oral DE capsule treatment. Three weeks prior, due to headaches, the patient's anti-cancer therapy was switched from pembrolizumab to encorafenib and binimetinib. The headaches may have been due to pembrolizumab or may have been due to seeding of CSF.

Stool sample was collected prior to bowel prep for induction FMT (Day −2 or Day −3) and on the day of initial FMT, following which stool samples were collected weekly. Stool was collected and stored by standard methods for future characterization. Molecular characterization including but not limited to microbiome sequencing (16S and/or shotgun metagenomics) was conducted.

Due to the advanced progression of his cancer, and likely caused by his metastatic spread to, at least, his inguinal lymph nodes, liver, and brain, 2 months after beginning the FMT, the patient died.

Example 2: Use of Fecal Microbiota
Transplantation (FMT) to Treat Chronic Diarrhea in
a 65-Year Old Male with Refractory Multiple
Myeloma In this example, a human patient with refractory multiple myeloma was treated with fecal microbiota transplantation (FMT) to help reduce his chemotherapy-induced chronic diarrhea.

The patient is a 65-year-old male with multiple myeloma. To treat the myeloma, the patient had been previously administered the chemotherapeutic agents fludarabine and Cytoxan, followed by an infusion of CAR-T cells. The patient's multiple myeloma status is considered highly refractory.

The patient had chronic diarrhea for over a year due to a viral infection, which led to weight loss and muscle wasting. His diarrhea substantially and markedly worsened following the chemotherapy, to the extent that typically seven to eight liters of diarrhea was released each day over two weeks. Consequently, the patient developed hypotension, electrolyte disturbances, and severe fatigue.

Immediately prior to FMT treatment, the patient was severely symptomatic and physically uncomfortable, and remained hospitalized due to the severity of the diarrhea and associated symptoms.

The patient was administered two FMTs via colonoscopy (each consisting of 250 ml of a liquid fecal microbiota composition prepared from stool of a healthy human donor). Prior to administration, the fecal microbiota was screened for a wide panel of infectious pathogens (including viral pathogens).

Following administration of the microbiota composition, the patient was monitored for fever, changes in diarrhea frequency, volume, and severity, and his stool was assayed for the presence of bacterial pathogens and viral pathogens.

The patient's condition markedly improved following the FMT treatments. In particular, the patient was able to leave the hospital and reported being more comfortable. Stool assays showed a reduction in the viral infection.

Example 3: Use of Fecal Microbiota
Transplantation (FMT) to Treat
Pembrolizumab-Induced Colitis in a 71-Year Old
Male Cancer Patient In this example, a human patient with a history of follicular lymphoma and gastric adenocarcinoma is administered fecal microbiota transplantation (FMT) to help treat his pembrolizumab-induced colitis.

The patient is a 71-year-old male with a history of follicular lymphoma (diagnosed six-years previously) and gastric adenocarcinoma (diagnosed three-years previously). These cancers were treated with surgery and subsequent pembrolizumab treatments. Following treatment with pembrolizumab, two sigmoidoscopies showed severe colitis.

To treat the colitis, the patient was administered via colonoscopy 250 ml of a liquid fecal microbiota composition prepared from the stool of a healthy, disease-screened human donor. Following administration, the patient's colitis was improved.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present disclosure is not entitled to antedate such publication by virtue of prior invention.

As used herein, all headings are simply for organization and are not intended to limit the disclosure in any manner. The content of any individual section may be equally applicable to all sections.

EQUIVALENTS

While the invention has been disclosed in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments disclosed specifically herein. Such equivalents are intended to be encompassed in the scope of the following claims.

What is claimed is:

1. A method of treating melanoma in a human subject in need thereof, the method comprising administering to the subject an immunotherapy, and orally administering to the subject a microbial composition comprising a non-selected community of fecal bacteria derived from a stool of a healthy human donor, wherein the microbial composition is administered at least one week prior to the immunotherapy.

2. The method of claim 1, wherein the immunotherapy comprises a compound directed to a checkpoint molecule.

3. The method of claim 2, wherein the compound is selected from pembrolizumab, nivolumab, ipilimumab and a combination thereof.

4. The method of claim 1, wherein the subject is non-responsive or refractory to administration of the immunotherapy.

5. The method of claim 1, wherein the community of fecal bacteria comprises a substantially entire fecal microbiota of the stool or a portion thereof.

6. The method of claim 1, wherein the community of fecal bacteria is extracted from the stool using at least one of filtration and centrifugation.

7. The method of claim 1, wherein the microbial composition comprises a cryoprotectant selected from polyethylene glycol, skim milk, erythritol, arabitol, sorbitol, glucose, fructose, alanine, glycine, proline, sucrose, lactose, ribose, trehalose, dimethyl sulfoxide (DMSO), glycerol and a combination thereof.

8. The method of claim 7, wherein the cryoprotectant is glycerol.

9. The method of claim 1, wherein the microbial composition is encapsulated.

10. The method of claim 9, wherein the community of fecal bacteria is lyophilized.

11. The method of claim 9, wherein the microbial composition is formulated as a liquid or suspension.

12. The method of claim 1, wherein the microbial composition is administered only once.

13. A method of treating melanoma in a human subject in need thereof, the method comprising administering to the subject a checkpoint inhibitor, and orally administering to the subject a mixture of non-selected fecal bacteria extracted from a stool of a healthy human donor, wherein the mixture of fecal bacteria is administered at least one week prior to the checkpoint inhibitor.

14. The method of claim 13, wherein the checkpoint inhibitor is selected from pembrolizumab, nivolumab, ipilimumab and a combination thereof.

15. The method of claim 1, wherein about 50 mg to about 150 mg of the microbial composition is administered.

16. The method of claim 15, wherein unit dosage forms comprising the microbial composition are administered, wherein each unit dosage form comprises from about 0.1 mg to about 5 mg of the microbial composition.

17. The method of claim 13, wherein about 50 mg to about 150 mg of the mixture of non-selected fecal bacteria is administered.

18. The method of claim 17, wherein unit dosage forms comprising the mixture of non-selected fecal bacteria is administered, wherein each unit dosage form comprises from about 0.1 mg to about 5 mg of the microbial composition.

19. The method of claim 13, wherein the mixture of non-selected fecal bacteria is encapsulated.

20. The method of claim 13, wherein the mixture of non-selected fecal bacteria is formulated as a liquid or suspension.

* * * * *